(12) United States Patent
Wender et al.

(10) Patent No.: US 8,816,122 B2
(45) Date of Patent: Aug. 26, 2014

(54) PROSTRATIN ANALOGS, BRYOSTATIN ANALOGS, PRODRUGS, SYNTHETIC METHODS, AND METHODS OF USE

(75) Inventors: Paul A. Wender, Menlo Park, CA (US); Lars V. Heumann, Redwood City, CA (US); Rainer Kramer, Freiburg im Bresigau (DE); Carolyn Gauntlett, Singapore (SG); Elizabeth Mieuli, Redwood City, CA (US); Dennis Fournogerakis, Stanford, CA (US); Pierre-Luc Boudreault, Sherbrooke, CA (US); Adam Schrier, Redwood City, CA (US); Brian DeChristopher, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 259 days.

(21) Appl. No.: 12/839,808

(22) Filed: Jul. 20, 2010

(65) Prior Publication Data

US 2011/0014699 A1 Jan. 20, 2011

Related U.S. Application Data

(60) Provisional application No. 61/226,802, filed on Jul. 20, 2009.

(51) Int. Cl.
*C07C 69/76* (2006.01)
(52) U.S. Cl.
USPC .......................................................... 560/105
(58) Field of Classification Search
None
See application file for complete search history.

(56) References Cited

PUBLICATIONS

Brooks et al. (Toxicon, 1987, 25(11), 1229).*
Zayed et al. (Planta Medica, 1984, 50(1), 65).*
Kinzel et al. (Cancer Research, 1979, 39, 2743).*
Sorg et al. (Carcinogenesis, 1988, 9, 1829).*
Hergenhahn et al. (J. Cancer Res. Clin. Oncol., 1984, 108, 98).*
Wender, et al.; The Practical Synthesis of a Novel and Highly Potent Analogue of Bryostatin; J. Am. Chem. Soc. 2002, 124, 13648-13649.
Wender, et al.; Efficient Synthetic Access to a New Family of Highly Potent Bryostatin Analogues Via a Prins-Driven Macrocyclizatio Strategy; J. Am. Chem. Soc. 2008, 130, 6658-6659.
Boto, et al.; Distinct Modulatory Effects of Bryostatin 1 and Staurosporine on the Biosynthesis and Expression of the HIV Receptor Protein (CD4) by T Cells; Cell Regulation, vol. 2, 95-103, Feb. 1991.
Esa, et al.; Activation of T-Cells by Bryostatins: Induction of the IL-2 Receptor Gene Transcription and Down-Modulation of Surface Receptors; Int. J. Immunopharmac., vol. 12, No. 5, pp. 481-490, 1990.
Qatsha, et al.; Go6976, a Selective Inhibitor of Protein Kinase C, is a potent Antagonist of Human Immunodeficiency Virus 1 Induction From Latent/Low-Level-Producing Reservoir Cells In Vitro; Proc. Natl. Acad. Sci. USA; vol. 90, pp. 4674-4678, May 1993.

(Continued)

*Primary Examiner* — Rosalynd Keys
*Assistant Examiner* — Jennifer C Sawyer
(74) *Attorney, Agent, or Firm* — Thomas | Horstemeyer, LLP.

(57) ABSTRACT

Embodiments of the present disclosure provide for prostratin analogs, bryostatin analogs, prodrugs of prostratin and prostratin analogs, methods of making prostratin analogs, and methods of making prodrugs of prostratin and prostratin analogs, methods of use of prostratin analogs, bryostatin analogs, and prodrugs thereof, and the like.

7 Claims, 28 Drawing Sheets

(56) References Cited

PUBLICATIONS

Wender; et al.; Modeling of the Bryostatins to the Phorbol Ester Pharmacophore on Portein Kinase C; Proc. Natl. Acad. Sci., USA; vol. 85, pp. 7197-7201, Oct. 1988.

Pettit, et al.; Isolation and Structure of Bryostatin 1; J. Am. Chem. Soc.; 1982, 104, 6846-6848.

Kinter, et al.; Direct and Cytokine-Mediated Activation of Protein Kinase C Induces Human Immunodeficiency Virus Expression in Chronically Infected Promonocytic Cells; Journal of Virology, Sep. 1990, p. 4306-4312.

Hale, et al.; New Approaches to the Total Synthesis of the Bryostatin Antitumor Macrolides; Chem. Asian J., 2010, 5, 704-754.

* cited by examiner

24

22

20

23

5

12

21

9 
(DPP)

18

4

29

10

26

40

3

6

11

2

8

13

14

30

7

40

Prostratin a) 0.01 M H₂SO₄, 90 °C, 1h, 40% b) triphenylmethyl chloride, pyridine, 23 °C, 12h quantitative

31 c) N₂H₄·H₂O, AcOH, MeOH, 23 °C, 2h d) toluene, iPr₂NEt, 150 °C e) Pb(OAc)₄, CH₂Cl₂, 0 °C, 45%

32 h) R₂COOH, 1-ethyl-3-(3-dimethylaminopropyl) carbodiimide hydrochloride, DMAP, THF, 23 °C, 12 h 80-99% i) HClO₄, MeOH, 23 °C, 40 min, 89-99%

35

36

PROSTRATIN ANALOGS, BRYOSTATIN ANALOGS, PRODRUGS, SYNTHETIC METHODS, AND METHODS OF USE

CROSS-REFERENCE TO RELATED APPLICATIONS

This application claims priority to U.S. provisional application entitled, "PROSTRATIN ANALOGS, PRODRUGS, AND SYNTHETIC METHODS," having Ser. No. 61/226,802, filed on Jul. 20, 2009, which is entirely incorporated herein by reference.

STATEMENT OF GOVERNMENTAL SUPPORT

This invention was made with government support under grant number CA31841, awarded by the U.S. National Institutes of Health of the United States government. The government has certain rights in the invention.

BACKGROUND

Prostratin is a nontumor-promoting 12-deoxyphorbol ester that has been shown to inhibit HIV-induced cell death and viral replication in vitro. The antiviral activity of this compound was discovered as a result of ethnobotanical studies on the island of Savai'i, Samoa, where traditional healers use the bark of *Homalanthus nutans* (G. Forst.) Guill. (Euphorbiaceae), a small rain-forest tree called "mamala", to treat hepatitis. Low concentrations of prostratin, from 0.1 to >25 M, have been found to protect T-lymphoblastoid CEM-SS and C-8166 cells from the lethal effects of HIV-1 and inhibit viral replication in these cell lines. The compound also demonstrated cytoprotective activity in the human monocytic cell line U937 and in freshly isolated human monocyte/macrophage cultures. Prostratin was found to bind to and activate protein kinase C in vitro in CEM-SS cells. Unlike other known phorbol esters, however, the compound has proved not to be a tumor promoter and has actually been shown to be a potent antitumor promoter.

In latently infected CD4+ T cells, prostratin induces HIV gene expression. NF-κB and PKC (α and θ) activation are the key events triggered by prostratin. Although other phorbol esters such as PMA (phorbol 12-myristate-13-acetate) are also shown to activate latent HIV, prostratin differs markedly from these and offers distinct therapeutic value because it does not exhibit the tumor-promoting activity of these other agents. Therefore, prostratin is a promising therapeutic lead as an adjuvant to be used in HAART (highly active antiretroviral therapy).

In an in vitro study, prostratin was shown to protect T-lymphoblastoid CEM-SS and C-8166 cell lines. At a prostratin concentration of approximately 1 μM, cell viability was restored to the level of uninfected controls, and no sign of cytotoxicity was observed up to about 25 μM. The mode of action is unclear, but the Ki of prostratin for PKC is 12 nM, suggesting the involvement of PKC in the process. (Gulakowski, R. J.; McMahon, J. B.; Buckheit, R. W., Jr.; Gustafson, K. R.; Boyd, M. R. Antireplicative and anti cytopathic activities of prostratin, a non-tumor-promoting phorbol ester, against human immunodeficiency virus (HIV). *Antiviral Res* 1997, 33, 87-97.)

Prostratin inhibits HIV invasion into healthy cells by downregulating the expression of HIV receptors on cell surfaces In CEM-SS and MT-4 cell lines, CD4 receptors were significantly reduced on cell surfaces, and mRNA array assay confirmed that CD4 gene expression along with other HIV-1 receptors (CXCR4 and CCR5) were downregulated in THP-1 cells. Staurosporine, a PKC inhibitor, was shown to reverse the CD4 downregulation by prostratin, implying the involvement of PKC activation in the process. In addition, prostratin stimulates the internalization and subsequent degradation of CD4 and CXCR4 receptors in CEM cells. PKC translocation studies on this cell line showed PKCβ and PKCδ remained in the cytosol, whereas PKC and c were effectively translocated to the plasma membrane (Gustafson, K. R; Cardellina, J. H., 2nd; McMahon, J. B.; Gulakowski, R. J.; Ishitoya, J.; Szallasi, Z.; Lewin, N. E.; Blumberg, P. M.; Weislow, O, S.; Beutler, J. A.; et al., A non promoting phorbol from the Samoan medicinal plant *Homalanthus nutans* inhibits cell killing by HIV-1. J. Med. Chem. 1992, 35, 1978-1986. (b) Wang, Y. B.; Huang, R.; Wang, H. B.; Jin, H. Z.; Lou, L. G.; Qin, G. W. Diterpenoids from the roots of Euphorbia fischeriana. J. Nat. Prod. 2006, 69, 967-970.)

In a more recent study, DPP (12-deoxyphorbol 13-phenylacetate), another non-tumor promoting phorbol ester, was reported to be 20-30 fold more potent than prostratin in activating latent HIV-1. DPP also downregulates CD4 and CXCR4 receptors at nanomolar concentrations. (Bocklandt, S.; Blumberg, P. M.; Hamer, D. H. Activation of latent HIV-1 expression by the potent anti-tumor promoter 12-deoxyphorbol 13-phenylacetate. Antiviral Res. 2003, 59, 89-98.)

SUMMARY

Embodiments of the present disclosure provide for prostratin analogs, bryostatin analogs, prodrugs of prostratin and prostratin analogs, methods of making prostratin analogs, and methods of making prodrugs of prostratin and prostratin analogs, methods of use of prostratin analogs, bryostatin analogs, and prodrugs thereof, and the like.

An illustrative embodiment of the compound, among others, includes a compound described by Formula I:

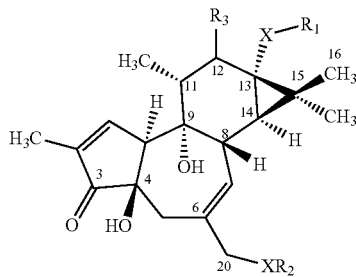

wherein in X in each instance is independently selected from: O, S, and N; wherein $R_1$ is a mono- or di-substituent, depending on X, selected from: H, substituted or unsubstituted alkyl, substituted or unsubstituted aryl, substituted or unsubstituted cycloalkyl, substituted or unsubstituted cycloalkenyl, substituted or unsubstituted aryl, substituted or unsubstituted biaryl, substituted or unsubstituted fused aryl, substituted or unsubstituted alkenyl, and substituted or unsubstituted alkynyl; wherein R2 is a mono- or di-substituent selected from H or a prodrug linkage which is selected from: an acyl, disulfide, amido, ester, primary or secondary amine, hydroxyl, sulfhydryl, carboxyl, aldehyde, ketone, bromide, fluoride, and chloride; and wherein R3 is a mono- or di-substituent selected from: H, substituted or unsubstituted alkyl, substituted or unsubstituted aryl, substituted or unsubstituted cycloalkyl, substituted or unsubstituted cycloalkenyl, substituted or unsubstituted aryl, substituted or unsubstituted biaryl, substituted or unsubstituted fused aryl, substituted or unsubstituted alkenyl, and substituted or unsubstituted alkynyl.

An illustrative embodiment, among others, includes a compound according to any one of Formula II, Formula III', Formula III", Formula IV', Formula IV", Formula V, Formula VI' and VI" and Formula VII' and VII", described below:

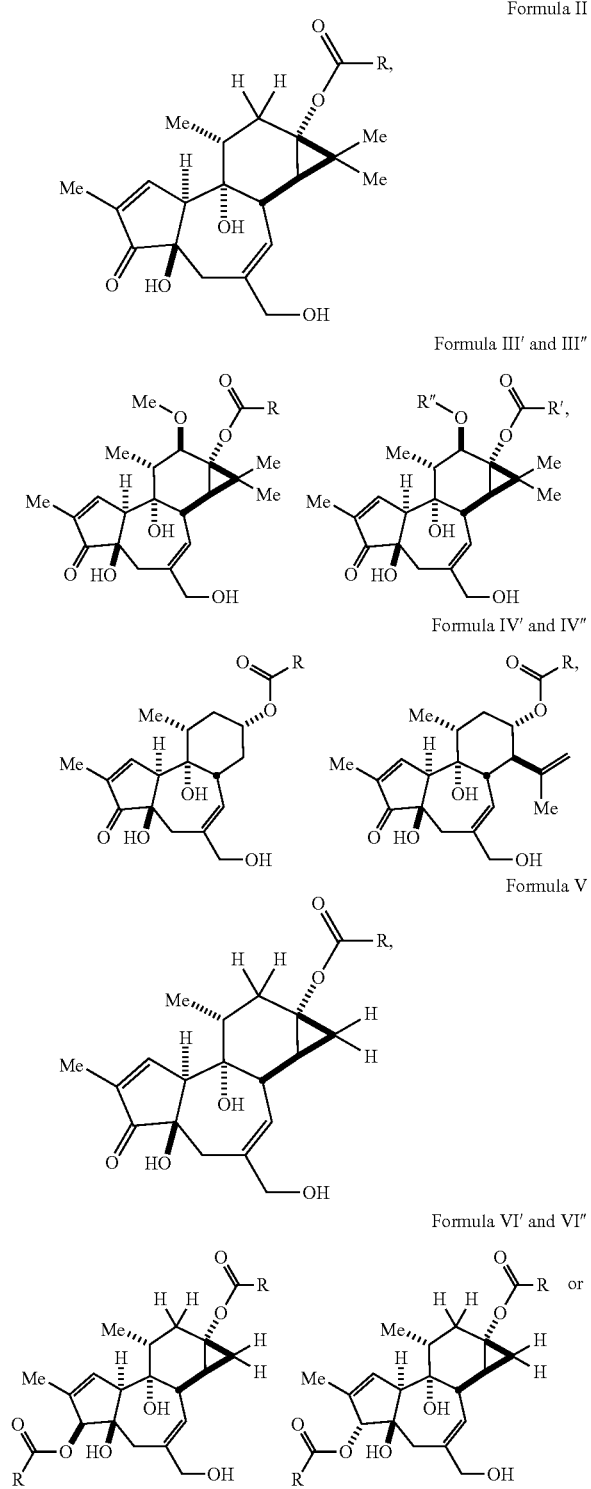

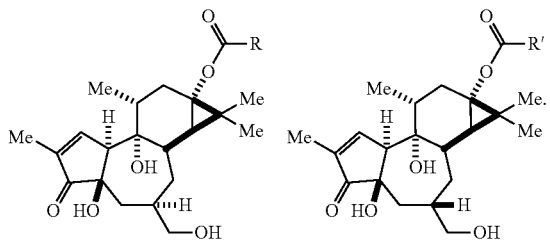

wherein R is selected from: H, substituted or unsubstituted alkyl, substituted or unsubstituted aryl, substituted or unsubstituted cycloalkyl, substituted or unsubstituted cycloalkenyl, substituted or unsubstituted aryl, substituted or unsubstituted biaryl, substituted or unsubstituted fused aryl, substituted or unsubstituted alkenyl, and substituted or unsubstituted alkynyl; and wherein R' is selected from: H, substituted or unsubstituted alkyl, substituted or unsubstituted aryl, substituted or unsubstituted cycloalkyl, substituted or unsubstituted cycloalkenyl, substituted or unsubstituted aryl, substituted or unsubstituted biaryl, substituted or unsubstituted fused aryl, substituted or unsubstituted alkenyl, and substituted or unsubstituted alkynyl.

An illustrative embodiment, among others, includes a prodrug of a compound of described by Formula I, Formula II, Formula III', Formula III", Formula IV', Formula IV", Formula V, Formula VI', Formula VI", Formula VII', and Formula VII" as well as bryostatin analogs described herein, wherein the prodrug linkage is selected from an ester, an acid anhydride, a disulfide, and an acid anhydride.

An illustrative embodiment, among others, includes a method of exposing a cell to one or more of the prostatin analogs or bryostatin analogs described herein and activating protein kinase C.

An illustrative embodiment, among others, includes a method of inhibiting cell growth in K562 cells by contacting the K562 cells with one or more of the prostatin analogs or bryostatin analogs described herein.

An illustrative embodiment, among others, includes a method of activating latent HIV, latent HIV or HIV in latently infected cells by contacting the cell with one or more of the prostatin analogs or bryostatin analogs described herein.

An illustrative embodiment of a method of making a compound, among others, includes: (a) obtaining crotophorbolone; (b) attaching a protective group to said crotophorbolone at C20; (c) forming a cyclopropane compound among C13, C14 and C15, and a hydroxyl group at C13; (d) esterifying the hydroxyl group; and (e) removing the protective group at C20, wherein the compound formed is a compound represented by Formula I.

An illustrative embodiment of a method of making a compound, among others, includes: (a) protecting phorbol at C20; (b) esterifying C13 hydroxy to form an X—R1 compound of choice; (c) alkylating C12 hydroxyl; and (d) deprotecting the compound, wherein the compound formed is one of the compounds represented by Formula I.

BRIEF DESCRIPTION OF THE DRAWINGS

Further aspects of the present disclosure will be more readily appreciated upon review of the detailed description of its various embodiments, described below, when taken in conjunction with the accompanying drawings.

DETAILED DESCRIPTION

Figure 1:
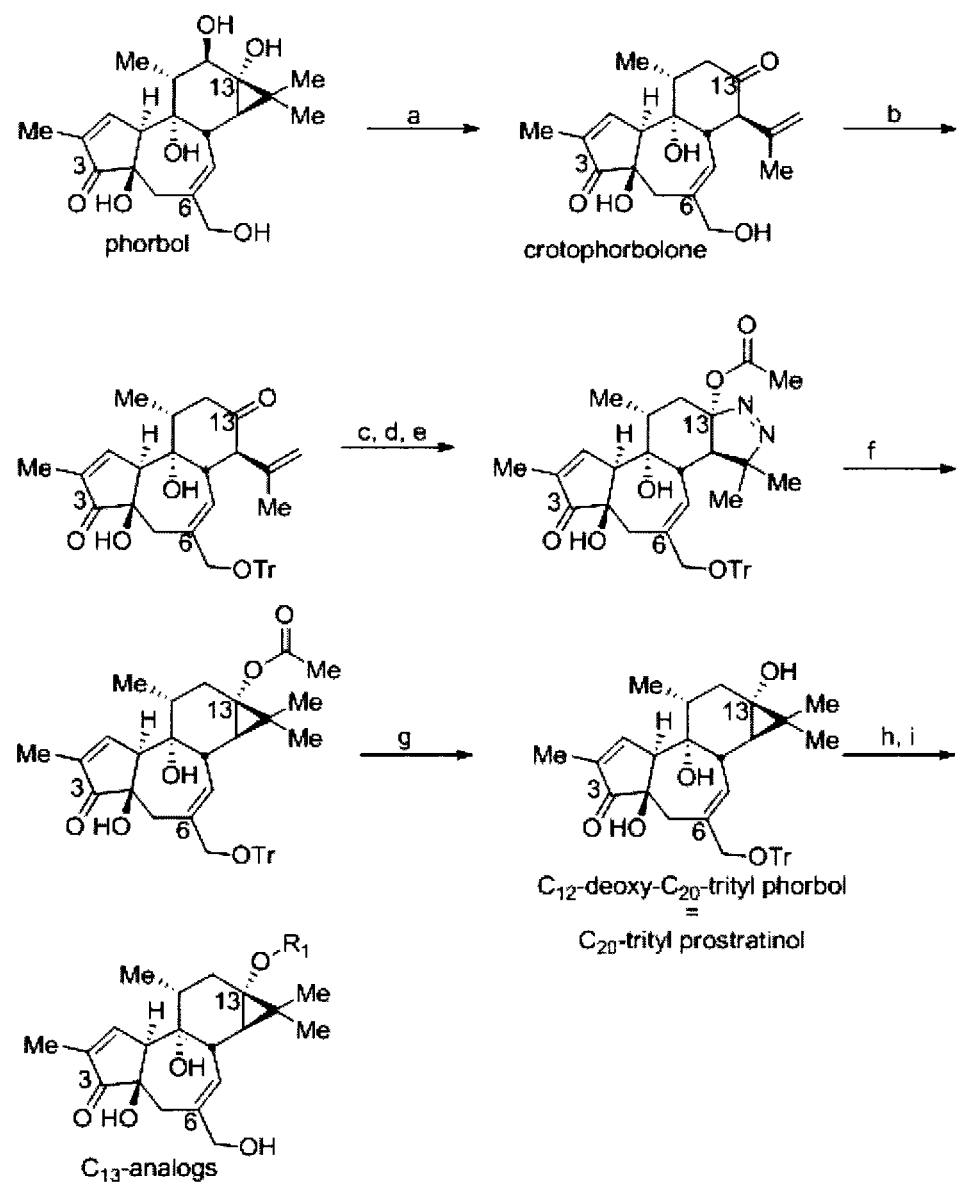
FIG. 1 is a reaction scheme as set forth in Example 1, illustrating variations possible at position C13, wherein R1 is as indicated in Formula I.
Figure 2A:
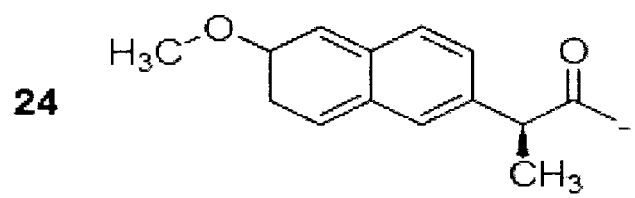
FIGS. 2A through 2F are schematic representations of certain R1 substituents in Formula I, where X=O, R2=H, and R3=H. In these Figures, preferred embodiments of present compounds are listed in order as compounds 24, 22, 20, 23, 5, 12, 21, 9, 18, 4, 29, 10, 26, 40, 3, 6, 11, 2, 8, 13, 14, 30, 7 and 41.
Figure 2A:
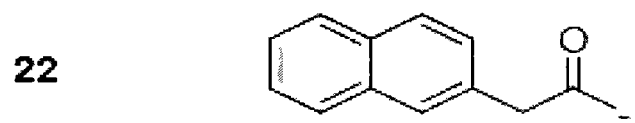
Figure 2A:
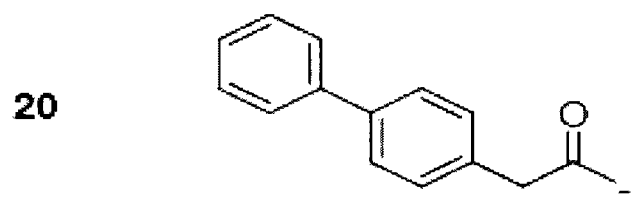
Figure 2A:
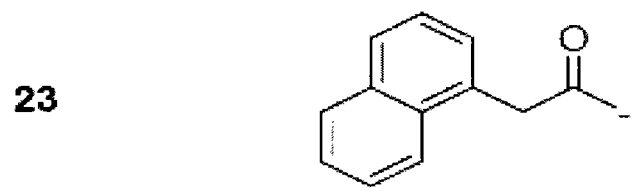
Figure 2B:
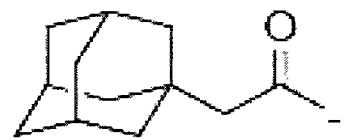
Figure 2B:
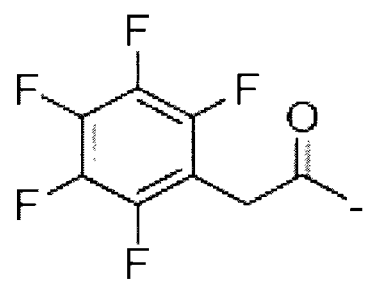
Figure 2B:
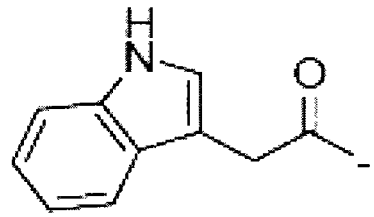
Figure 2B:
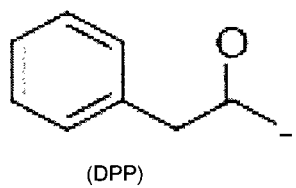
Figure 2C:
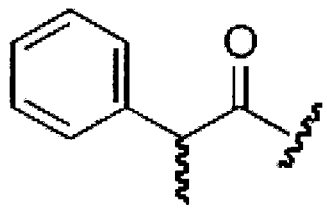
Figure 2C:
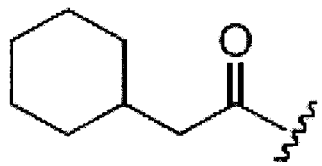
Figure 2C:
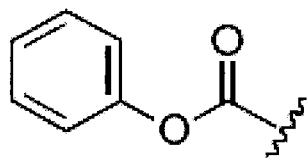
Figure 2C:
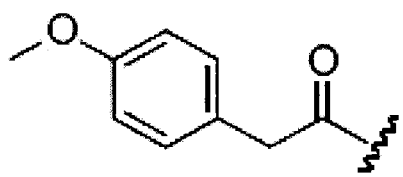
Figure 2C:
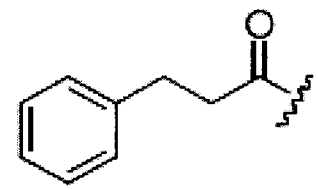
Figure 2D:
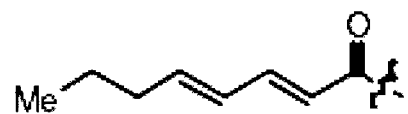
Figure 2D:
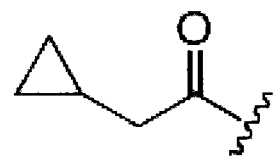
Figure 2D:
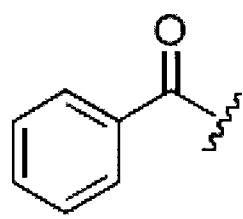
Figure 2D:
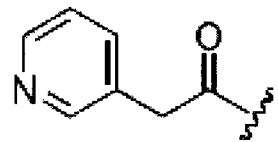
Figure 2D:
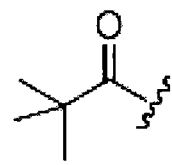
Figure 2E:
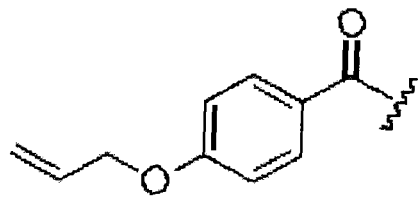
Figure 2E:
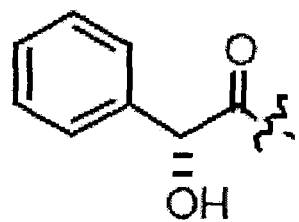
Figure 2E:
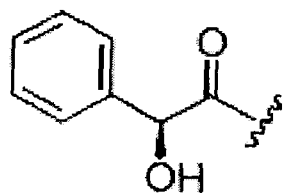
Figure 2E:
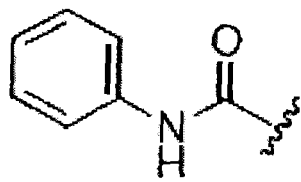
Figure 2E:
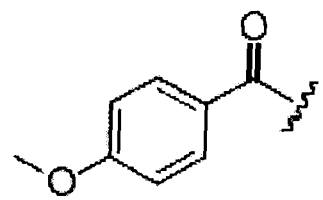
Figure 2F:
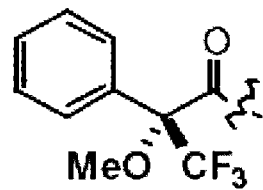
Figure 2F:
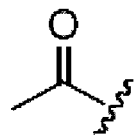

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

DEFINITIONS

The term "direct bond" refers to a chemical bond such as a covalent bond or an ionic bond.

The term "substituted" refers to any one or more hydrogens on the designated atom that can be replaced with a selection from the indicated group, provided that the designated atom's normal valence is not exceeded, and that the substitution results in a stable compound. When a substituent is keto (i.e., C—C(═O)—C), then 2 hydrogens on the atom can be replaced. Keto substituents are not present on aromatic moieties. When a ring system (e.g., carbocyclic or heterocyclic) is said to be substituted with a double bond, it is intended that the carbonyl group or double bond be part of the ring.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

As used herein, "alkenyl" or "alkenyl group" refers to an aliphatic hydrocarbon radical which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "arylalkyl" refers to an arylalkyl group wherein the aryl and alkyl are as herein described. Examples of arylalkyl include, but are not limited to, -phenylmethyl, -phenylethyl, -phenylpropyl, -phenylbutyl, and -phenylpentyl.

The term "substituted," as in "substituted alkyl", "substituted cycloalkyl," "substituted cycloalkenyl," substituted aryl," substituted biaryl," "substituted fused aryl" and the like means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. The term "lower alkoxy" means an alkoxy group having less than 10 carbon atoms.

The term "cycloalkyl" refers to a non-aromatic mono- or multicyclic ring system of about 3 to about 10 carbon atoms, preferably of about 5 to about 10 carbon atoms. Preferred ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

The term "cycloalkenyl" refers to a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. Exemplary monocyclic cycloalkenyl include cyclopentenyl, cyclohexenyl, cycloheptenyl, and the like. An exemplary multicyclic cycloalkenyl is norbornylenyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

The term "biaryl" refers to an aryl, as defined above, where two aryl groups are joined by a direct bond or through an intervening alkyl group, preferably a lower alkyl group.

The term "fused aryl" refers to a multicyclic ring system as included in the term "aryl," and includes aryl groups and heteroaryl groups that are condensed. Examples are naphthyl, anthryl and phenanthryl. The bonds can be attached to any of the rings.

"Aralkyl" and "heteroaralkyl" refer to aryl and heteroaryl moieties, respectively, that are linked to a main structure by an intervening alkyl group, e.g., containing one or more methylene groups.

The term "fluorobenzyl" refers to a benzyl group wherein the phenyl moiety is substituted with one or more fluorine atoms, including 2, 3, 4 and 5 fluorine atom substituents.

Similarly, "halobenzyl" refers to benzyl substituted with one or more different halogens, including fluorine, chlorine, bromine, and iodine (not astatine).

The terms "sulfide" and "thioether" as used herein, alone or in combination, refer to a sulfur atom covalently linked to two atoms; the formal oxidation state of said sulfur is (II). These terms may be used interchangeably.

The term "sulfanyl" as used herein, alone or in combination, refers to the —S—R group, wherein R may be a group such as: alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. Non-limiting examples of sulfanyl groups include methylsulfanyl (—SCH$_3$) and iso-propylsulfanyl (—SCH(CH$_3$)$_2$) and the like.

The term "sulfoxide" as used herein, alone or in combination, refers to a sulfur atom covalently linked to three atoms, at least one of which is an oxygen atom; the formal oxidation state of said sulfur atom is (IV).

The term "sulfinyl" as used herein, alone or in combination, refers to the groups —S(O)—R, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfinyl group includes methylsulfinyl (—S(O)CH$_3$) and the like.

The term "sulfone" as used herein, alone or in combination, refers to a sulfur atom covalently linked to four atoms, at least two of which are oxygen atoms; the formal oxidation state of said sulfur atom is (VI).

The term "sulfonyl" as used herein, alone or in combination, refers to the groups —$S(O_2)$—R, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfonyl group includes methylsulfonyl (—$S(O_2)CH_3$) and the like.

The term "phosphate" as used herein, alone or in combination, refers to a phosphorus atom covalently linked to three carbon atoms, wherein the formal oxidation state of said phosphorus is (III).

The term "phosphinyl" as used herein, alone or in combination, refers to the monoradical derived from a phosphite group, as defined above.

The term "phosphonate" as used herein, alone or in combination, refers to a phosphorus atom covalently linked to four atoms, three of which are oxygen and one of which is carbon wherein the formal oxidation state of said phosphorus is (V).

The term "phosphonyl" as used herein, alone or in combination, refers to the monoradical derived from a phosphonate group, as defined above.

The term "phosphate" as used herein, alone or in combination, refers to a phosphorus atom covalently linked to four oxygen atoms, wherein the formal oxidation state of said phosphorus is (V).

The term "phosphatidyl" as used herein, alone or in combination, refers to the monoradical derived from a phosphate group, as defined above.

The terms ketone, ester, ether, and acyl have their art recognized meanings.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salts" refers to a compound of the present disclosure that can be modified by making acid or base salts thereof. Pharmaceutically acceptable salt refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Examples of pharmaceutically acceptable salts include, but are not limited to, mineral or organic acid salts of basic residues such as amines; and alkali or organic salts of acidic residues such as carboxylic acids.

In the event that embodiments of the present disclosure form salts, these salts are within the scope of the present disclosure. Reference to an agent of any of the formulas herein is understood to include reference to salts thereof, unless otherwise indicated. The term "salt(s)", as employed herein, denotes acidic and/or basic salts formed with inorganic and/or organic acids and bases. In addition, when an agent contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an agent may be formed, for example, by reacting the agent with an amount of acid or base, such as an equivalent amount, in a medium such as one in which the salt precipitates or in an aqueous medium followed by lyophilization.

Embodiments of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the agents that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

As used herein, "agent", "active agent", "inhibitor" or the like, can include a compound of the present disclosure. The agent or inhibitor can be disposed in a composition or a pharmaceutical composition.

As used herein, "treat", "treatment", "treating", and the like refer to acting upon a disease or disorder with an agent to affect the disease or disorder by improving or altering it. The improvement or alteration may include an improvement in symptoms or an alteration in the physiologic pathways associated with the disease or disorder. "Treatment," as used herein, covers one or more treatments of a disease in a host (e.g., a mammal, typically a human or non-human animal of veterinary interest), and includes: (a) reducing the risk of occurrence of the disease in a subject determined to be predisposed to the disease but not yet diagnosed as infected with the disease (HIV/AIDS) (b) impeding the development of the disease, and/or (c) relieving the disease, e.g., causing regression of the disease and/or relieving one or more disease symptoms.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a disease or symptom thereof and/or may be therapeutic in terms of a partial or complete cure for a disease and/or adverse effect attributable to the disease.

The terms "activate" and "activation" can refer to a response (e.g., immune response) from acting upon a biological target with a compound of the present disclosure.

As used herein, "agent", "active agent", or the like, can include a compound of the present disclosure. The agent or inhibitor can be disposed in a composition or a pharmaceutical composition.

As used herein, "pharmaceutical composition" refers to the combination of an active agent with a pharmaceutically acceptable carrier. As used herein, a "pharmaceutical composition" refers to a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "isolated compound" refers to a compound which has been substantially separated from, or enriched relative to, other compounds with which it occurs in nature. Isolated compounds are usually at least about 80%, at least 90% pure, at least 98% pure, or at least about 99% pure, by weight. The present disclosure is meant to include diastereomers as well as their racemic and resolved, enantiomerically pure forms and pharmaceutically acceptable salts thereof.

The term "unit dosage form," as used herein, refers to physically discrete units suitable as unitary dosages for human and/or animal subjects, each unit containing a predetermined quantity of a compound calculated in an amount sufficient (e.g., weight of host, disease, severity of the disease, etc) to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

The term "therapeutically effective amount" as used herein refers to that amount of an embodiment of the agent (which may be referred to as a compound) being administered that will relieve to some extent one or more of the symptoms of the disease being treated, and/or that amount that will prevent, to some extent, one or more of the symptoms of the disease that the host being treated has or is at risk of developing.

The term "prodrug" refers to a compound whose efficacy may be enhanced after a conversion step that occurs in vivo after administering the compound to a subject or patient. Typical examples of prodrugs include organic phosphates or esters of alcohols or thioalcohols. See Remington's Pharmaceutical Sciences, 16th Ed., A. Osol, Ed. (1980), the disclosure of which is incorporated by reference herein.

The term "pharmaceutically acceptable prodrugs" refers to those prodrugs of the compounds useful according to the present disclosure which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the disclosure. Exemplar prodrugs are described below in reference to prostratin and bryostatin and their analogs. Functional groups that may be rapidly transformed, by metabolic cleavage, in vivo form a class of groups reactive with the carboxyl group of the compounds of this disclosure. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this disclosure are cleaved in vivo, the compounds bearing such groups act as pro-drugs. The compounds bearing the metabolically cleavable groups have the advantage that they may exhibit improved bioavailability and or better ease of administration as a result of enhanced solubility and/or rate of absorption conferred upon the parent compound by virtue of the presence of the metabolically cleavable group. Prodrugs can include compounds of the present disclosure wherein a hydroxy, amino, or sulfhydryl group is bonded to any group that, when the prodrug of the present disclosure is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present disclosure. Additional examples are described in detail with relation to the prostratin and bryostatin and their analogs.

To the extent that the disclosed compounds, and salts thereof, may exist in their tautomeric form, all such tautomeric forms are contemplated herein as part of the present disclosure.

All stereoisomers of the compounds of the present disclosure, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "administration" refers to introducing a compound of the present disclosure into a host. One preferred route of administration of the compound is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, the term "host," "subject," "patient," or "organism" includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

DISCUSSION

Embodiments of the present disclosure provide for prostratin analogs, bryostatin analogs, prodrugs of prostratin and prostratin analogs, methods of making prostratin analogs, and methods of making prodrugs of prostratin and prostratin analogs, methods of use of prostratin analogs, bryostatin analogs, and prodrugs thereof, and the like.

In particular, embodiments of the present disclosure provide for compounds that are polycyclic and bear certain similarities to phorbol esters and can be referred to as phorbol ester analogs having substitutions at C12 and/or C13 positions of Formula I shown below. Embodiments of the compounds also include compounds represented by the following formula: Formula II, Formula III' and III", Formula IV' and IV", Formula V, Formula VI' and VI", and Formula VII' and VII".

Embodiments of the compounds (e.g., prostratin analogs, bryostatin analogs, and pharmaceutically acceptable prodrugs of prostratin and prostratin analogs) can exhibit activity against human immunodeficiency virus (HIV), stimulate transcription of proviral HIV DNA, and/or bind to protein kinase C. It has been discovered that prostratin analogs and bryostatin analogs have a common pharmacophore (i.e., same or similar subset of groups responsible for biological activity), and consequently have similar activities (See the Examples for additional details).

Embodiments of the present disclosure can be used as protective adjuvants in anticancer radiotherapy. Activators of NF-kappaB pathway can protect healthy cells from the radiation during anticancer radiotherapy. In studies with mice and rhesus monkeys, the survival rate of the animals after radiation therapy was significantly improved when the NF-kappaB activators were injected to the animals (*Science,* 2008, 320, 226-230, which is incorporated herein by reference). Therefore, embodiments of the present disclosure, being NF-kappaB activators without the tumor-promotion effect, could be used as adjuvants in anticancer radiotherapy.

Figure 5:
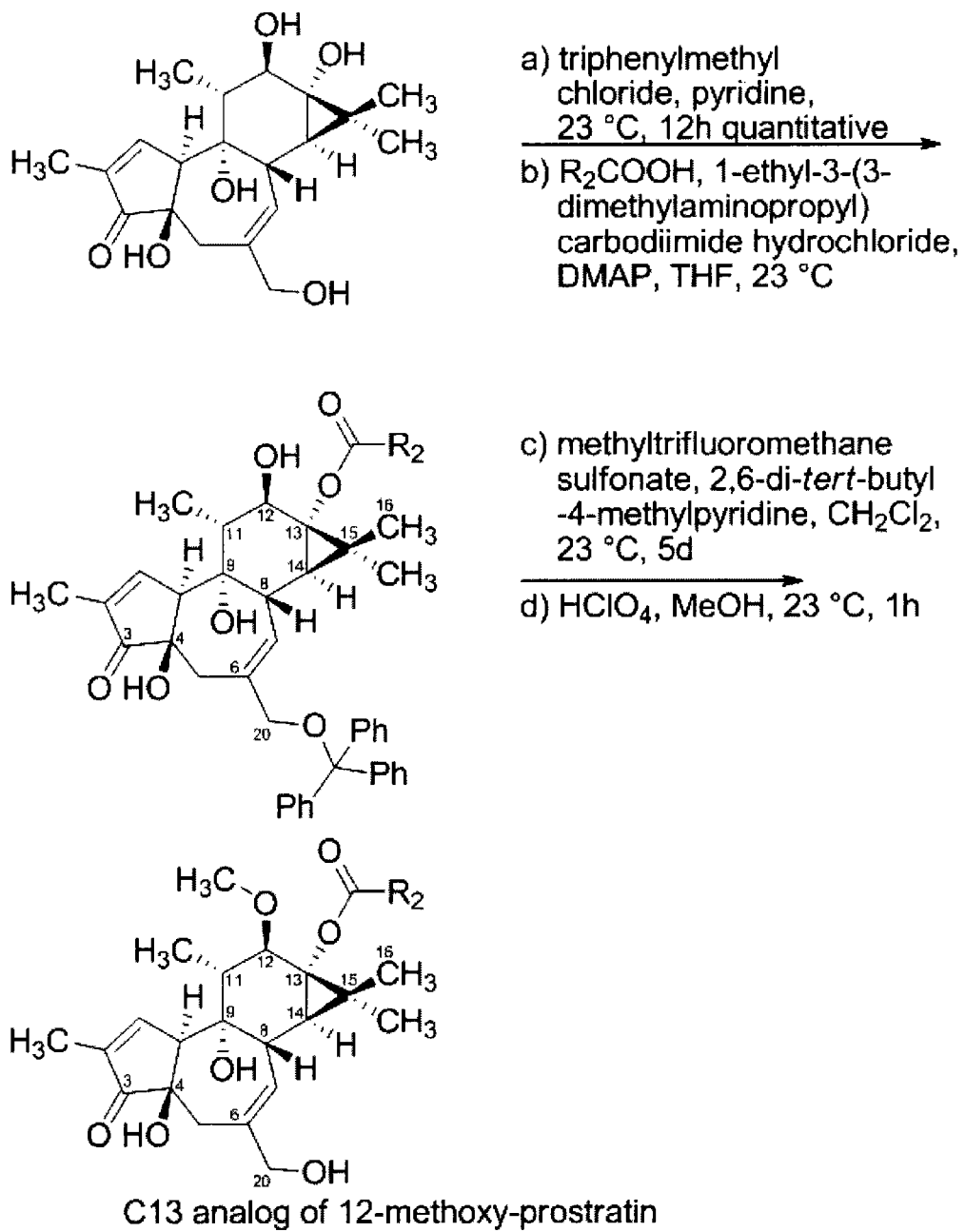
FIG. 5 is a schematic representation of another method of making C13 analogs.
Figure 6A:
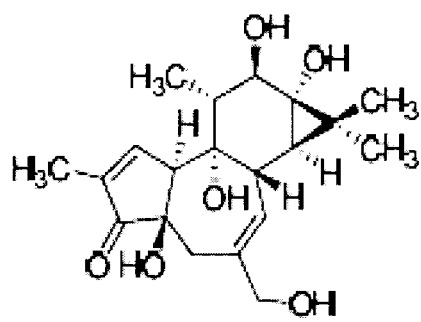
FIGS. 6A-6B are schematic representations of a method of making prostratin and related compounds having, e.g., methoxy at C12 and substituents R2 at C13.
Figure 6A:
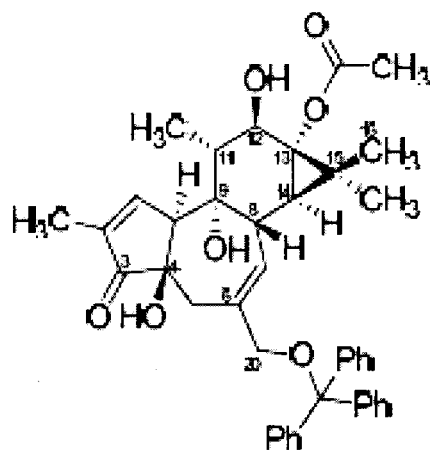
Figure 6B:
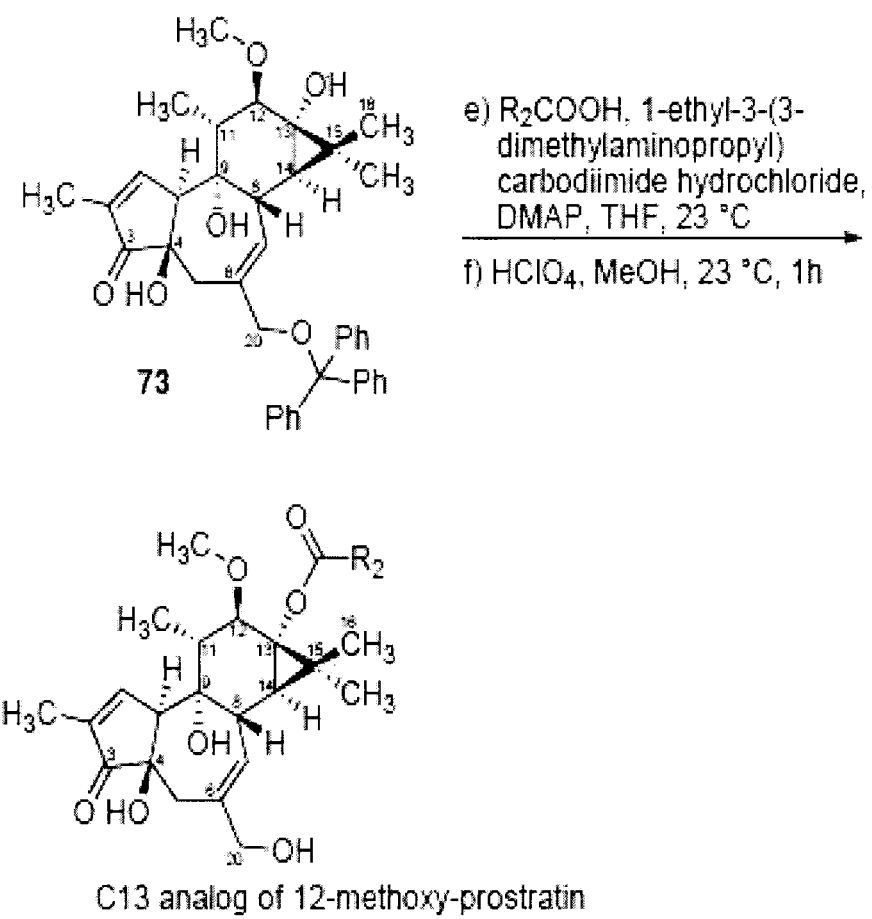

Embodiments of the present disclosure include a variety of synthetic routes that open up the synthesis of a wide variety of possible prostratin analogs and prodrugs. For example, FIGS. 1 and 3 describe a pyrazoline route involving a phorbol conversion to crotophorbolone, thus opening the cyclopropane ring and then reforming it. FIGS. 5 and 6A and 6B describe alkylation strategies.

Formula I, Formula II, Formula III' and III", Formula IV' and IV", Formula V, Formula VI' and VI", and Formula VII' and VII", correspond to compounds describing prostratin analogs. Formulae A-H corresponds to compounds describing bryostatin analogs.

The ring numbering in Formula I is provided for convenience and is also as found in U.S. Pat. No. 5,599,839. It is also understood that the compound of Formula I comprises four rings denominated from left to right A, (including position 3), B (including position 6), C (including position 12), and D (including position 15). The stereochemistry indicated below represents a preferred embodiment.

Embodiments of the present disclosure relate to compounds that differ from prostratin and DPP. Embodiments of the present disclosure can be defined by Formula I below.

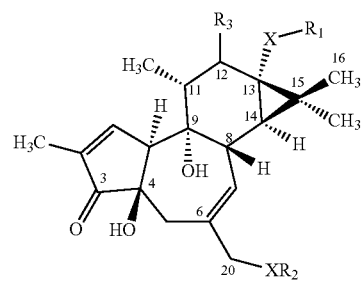

By way of illustration in prostratin, R3 is H, X is O, R1 is —C(═O)CH$_3$, and R2 is H. Another known compound, DPP, is similar except that R1 is C(═O)CH$_2$Phenyl. Another known compound, TPP (See U.S. Patent Application 2008/0226589) is similar except that R1 is C(═O)C$_{13}$H$_{27}$.

Compounds having novel substituents at positions C12 (R3 in the formula above) and C13 (X—R1 in the formula above) are described and are termed herein C12 or C13 analogs. Also described in connection with the present disclosure are prodrugs of prostratin, DPP, or novel compounds (Formula I) having different chemical groups at the C20 position (XR2 in the formula above).

In an embodiment, the present disclosure involves modifications in the prostratin/DPP structure at C13 that can provide improved binding to protein kinase C (PKC), and certain PKC isozymes. Examples of the present analogs have been shown to be significantly more potent than prostratin or DPP. Preferably, C13 in the present compounds can contain a carbonyl group and a fused, modified aromatic structure, FMA, as represented where, in Formula I, R1 is —C(═O)-FMA, or —C(═O)CH$_2$-FMA, or —C(═O)CH(CH$_3$)-FMA, where FMA may be, for example, a group derived from benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole or their substituted or benzo derivatives. Various substitutions in the fused modified aromatic structure are possible and are described herein. Also described herein are compounds where R1 is a cycloalkyl or other alkyl. Other linear, branched or cyclic alkanes may also be used as attached groups, such as bridged or Spiro hydrocarbons, e.g., tricyclo(3.3.1.1)decane (adamantane).

In another embodiment, the present disclosure comprises C12 analogs. The term "C12 analog" refers to a compound that is not H in its C12 position as shown in Formula I. C12 analog synthetic methods are shown in FIGS. 5 and 6A and 6B. These methods begin with phorbol. The C13 hydroxyl is esterified after the C20 hydroxy is protected. This permits reactions with the C12 hydroxyl group, such as alkylation. Alkylation reactions with cycloalcohol may be used to produce alkyl ethers. Additional details are provided below.

In embodiments pertaining to C13 analogs, R3 is H, otherwise R3 is as defined below.

X in each instance is independently selected from O, S, C, and N.

R1, relating to C13 analogs, can be selected from a mono- or di-substituent, depending on X, selected from: H, substituted or unsubstituted alkyl, substituted or unsubstituted aryl, substituted or unsubstituted cycloalkyl, substituted or unsubstituted cycloalkenyl, substituted or unsubstituted aryl, substituted or unsubstituted biaryl, substituted or unsubstituted fused aryl, substituted or unsubstituted alkenyl, and substituted or unsubstituted alkynyl. In particular, R1 may be selected from: aryl, biaryl, fused aryl, branched alkyl, or cyclo alkyl groups, as well as phosphates, sulfates, and the like, as well as esters and related or similar groups that can be linked to X and have substituents selected from: aryl, biaryl, fused aryl, branched alkyl, or cyclo alkyl groups. Representative and exemplary R1 groups are shown in FIGS. 2A-2F.

R2, at the C20 position, may be varied independently of R1 or R3, or may be H. In an embodiment, R2 can be selected from: a mono- or di-substituent selected from H or a prodrug linkage which is selected from: an acyl, disulfide, amido, ester, primary or secondary amine, hydroxyl, sulfhydryl, carboxyl, aldehyde, ketone, bromide, fluoride, and chloride. In the compounds in FIG. 1, R2 is H in Formula I when X=O. R2 may be H or a prodrug linkage such as an acyl, disulfide, amido, or ester. In an embodiment, the reactive functional groups include primary or secondary amines, hydroxyls, sulfhydryls, carboxyls, aldehydes, and ketones, bromides, fluorides, and chlorides. In an embodiment, the reactive functional groups include disulfide and esters.

R3, at the C12 position, may be varied independently of R1 and R2. In an embodiment, R3 can be a mono- or a di-substituent selected from: H, substituted or unsubstituted alkyl, substituted or unsubstituted aralkyl, substituted or unsubstituted cycloalkyl, substituted or unsubstituted cycloalkenyl, substituted or unsubstituted aryl, substituted or unsubstituted biaryl, substituted or unsubstituted fused aryl, substituted or unsubstituted alkenyl, and substituted or unsubstituted alkynyl. In an embodiment, R3 can be selected from: methoxy, ethoxy, acetoxy, acyloxy, phenyloxy, methylthio, ethylthio, phenylthio, fluoro, chloro, bromo, diethylamino, diphenylamino, dimethylamino, keto, methyl, ethyl, methylene, but not limited to, exocyclic olefin similar to C12=CH$_2$ or ethylene C12=CH—CH$_3$.

Analogs of phorbol esters, such as 12-deoxy phorbol esters, are disclosed where the C13 substituent has been modified from the C13 structure found in prostratin. The analogs differ significantly from the structure of prostratin, e.g., where C13 is —O—C(=O)—CH$_3$ and also differ significantly from 12-deoxyphorbol 13-phenylacetate (DPP), i.e., —O—C(=O)—C-Ph, where Ph is phenyl. As represented above in Formula I, R1 may be a variety of aryl, biaryl, fused aryl, branched alkyl or cyclo alkyl groups. Preferred R1 compounds are hydrogen bond donors or acceptors (e.g., compound II in FIG. 2). Aromatic rings act as hydrogen bond acceptors. The present analogs were shown to have high affinity for PKC in assays using K562 cells.

In other embodiments, the present disclosure can includes classes of compounds described by the Formula II, Formula III' and III", Formula IV' and IV", Formula V, Formula VI' and VI" and Formula VII' and VII", shown below. These classes are part of the Formula I family.

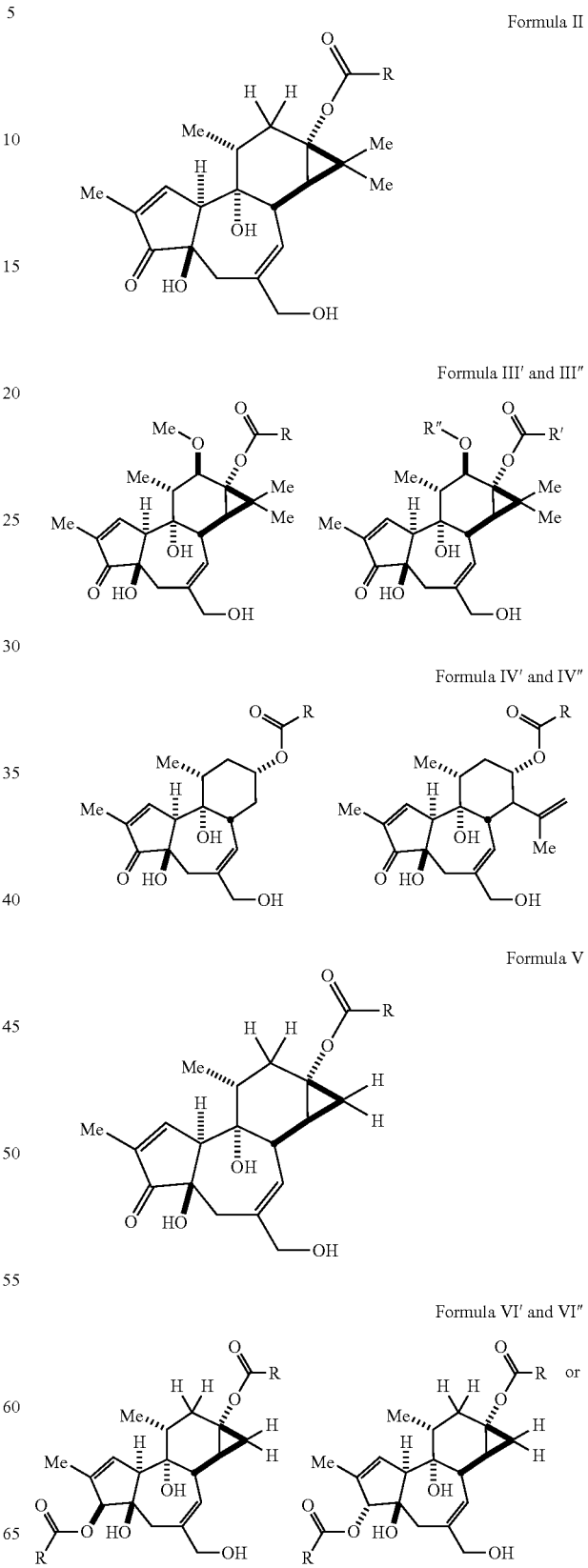

17

-continued

Formula VII' and VII"

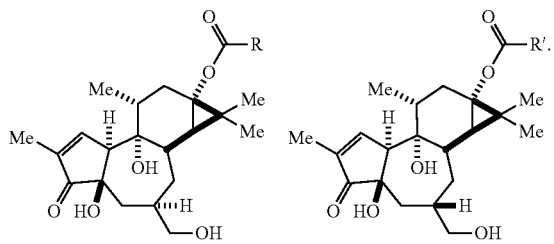

In an embodiment, R for each Formula (II to VII") and where R is used more than once in a single structure, R can be independently a mono- or di-substituent selected from: H, substituted or unsubstituted alkyl, substituted or unsubstituted aralkyl, substituted or unsubstituted cycloalkyl, substituted or unsubstituted cycloalkenyl, substituted or unsubstituted aryl, substituted or unsubstituted biaryl, substituted or unsubstituted fused aryl, substituted or unsubstituted alkenyl, and substituted or unsubstituted alkynyl.

In an embodiment including R', R', and/or R" for each Formula (II to VII") can be independently a mono- or a di-substituent selected from: H, substituted or unsubstituted alkyl, substituted or unsubstituted aralkyl, substituted or unsubstituted cycloalkyl, substituted or unsubstituted cycloalkenyl, substituted or unsubstituted aryl, substituted or unsubstituted biaryl, substituted or unsubstituted fused aryl, substituted or unsubstituted alkenyl, and substituted or unsubstituted alkynyl.

Exemplar compounds represented by Formula IV' and IV'" are shown below.

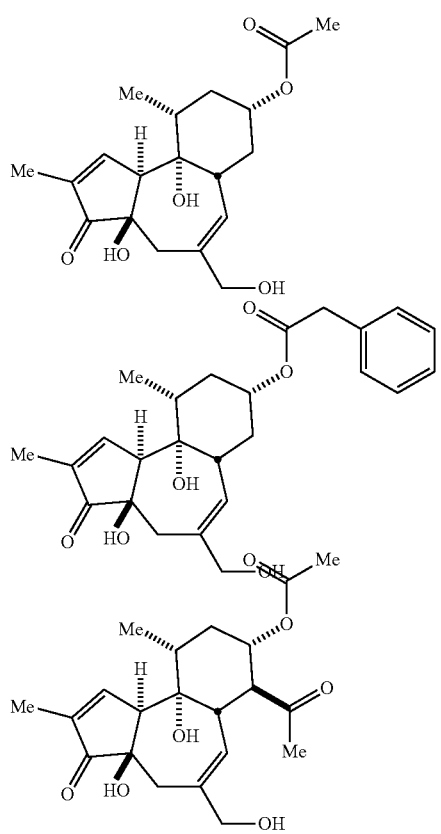

18

Exemplar compounds represented by Formula VI' and VI" are shown below.

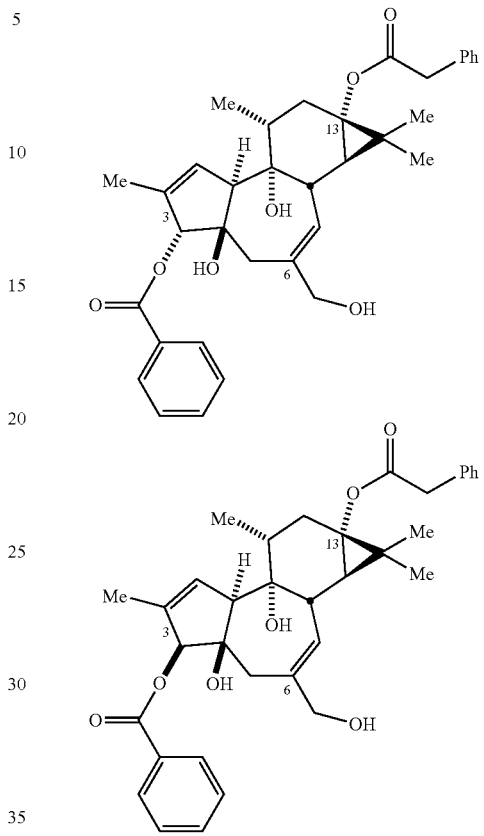

FIGS. 12A to 12E illustrate various specific compounds of the present disclosure.

In another embodiment, the present disclosure relates to prodrugs of phorbol ester compounds. The prodrugs employ a modification at the C20 position, in combination with possible modifications at C12 and C13 as described herein, whereby a cleavable linkage is used to create a labile bond at the C20 position that will yield a hydroxyl group upon activation. The linkage is from the C20 carbon to another group such as, for example, an ester, which is metabolized in vivo to produce a C20 hydroxyl group. The inactive group may be selected to enhance cellular uptake, such as an oligopeptide having a positive charge, which facilitates penetration of the drug into the cellular membrane. Embodiments of the present disclosure include prodrugs of Formula I, Formula II, Formula III' and III", Formula IV' and IV'", Formula V, Formula VI' and VI", and Formula VII' and VII".

The prodrug has the general formula PA-C20-linkage-CU, where PA is prostratin or a prostratin analog (Formula I) (bryostatin can replace PA for byrostatin prodrugs), C20 is the C20 carbon in that structure, linkage is a cleavable linkage, and CU is an organic group or other group (e.g., phosphate-based) that may be inert or confer stability, but preferably enhances uptake or activation of the PA or provides a method for slow release of the active drug in vivo. For example, the C20 position of prostratin (or any other analog described herein) can be acylated rendering it inactive. Under treatment conditions this acyl group would be cleaved either chemically or biologically (e.g., esterases) to release free prostratin. The ability to do this allows any of the active compounds (Formula I, Formula II, Formula III' and III", Formula IV' and IV", Formula V, Formula VI' and VI", and Formula VII' and VII") to be selected and modified to improve their ADME, PK and other properties, while still preserving the activity of the agent as it is eventually released as the free drug. The prodrug can be converted to the free drug while in transit to its target, for instance, after entering cells containing the target, etc. It could also be used to target cells after which the added acyl group falls off and the free drug acts upon the target cells.

As examples, the cleavable linkage may include a group that is hydrolyzable, enzymatically or otherwise cleavable in vivo, such as disulfide (which may be cleaved by the tripeptide glutathione), ester, thioester, amide, acid anhydride, or the like. The cleavable linkage may also be formed by oligonucleotides with a restriction site, peptides with a protease cleavage site, and the like. A cell uptake facilitating moiety that can be used is a cationic peptide, such as nonarginine (see Biochemistry. 01/04/200404/2004; 43(9):2438-44), or other oligoarginine peptides, as well as TAT peptides such as KKRRQRRR or subsequences thereof.

In regard to bryostatin analogs, the following compounds represented by Formulae A-H describe bryostatin analogs. Additional details regarding the bryostatin analogs can be found in U.S. Pat. No. 6,624,189, which is incorporated herein by reference. Embodiments of the bryostatin analogs can be represented by the following compounds represented by Formula A:

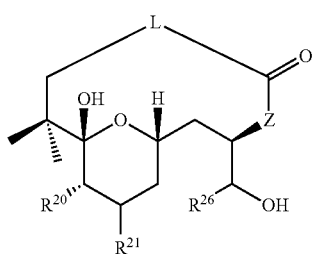

wherein:
$R^{20}$ is H, OH, or $O_2CR'$;
$R^{21}$ is $=CR^aR^b$ or $R^{21}$ represents independent moieties $R^c$ and $R^d$ where:
$R^a$ and $R^b$ are independently H, $CO_2R'$, $CONR^cR^d$ or R';
$R^c$ and $R^d$ are independently H, alkyl, alkenyl or alkynyl, or $(CH_2)_nCO_2R'$ where n is 1, 2 or 3;
$R^{26}$ is H, OH or R';
each R' being independently selected from the group: alkyl, alkenyl or alkynyl, or aryl, heteroaryl, aralkyl or heteroaralkyl;
L is a straight or branched linear, cyclic or polycyclic moiety, containing a continuous chain of preferably from 6 to 14 chain atoms, which substantially maintains the relative distance between the C1 and C17 atoms and the directionality of the C1C2 and C16C17 bonds of naturally-occurring bryostatin; and
Z is —O— or —N(H)—.

In an embodiment $R^{26}$ is H or methyl, particularly when $R^{21}$ is $=C(H)CO_2R'$. In another embodiment, $R^{26}$ is H. In an embodiment, an upper limit on carbon atoms in any of $R^d$, $R^e$ and R' is about 20, more preferably about 10 (except as otherwise specifically noted, for example, with reference to the embodiment where a preferred $R^{20}$ substituent has about 9 to 20 carbon atoms). In an embodiment, the spacer domain L contains a terminal carbon atom that, together with the carbon atom corresponding to C17 in the native bryostatin structure, forms a trans olefin.

Another embodiment of the bryostatin analogues can be represented by Formulae B-E:

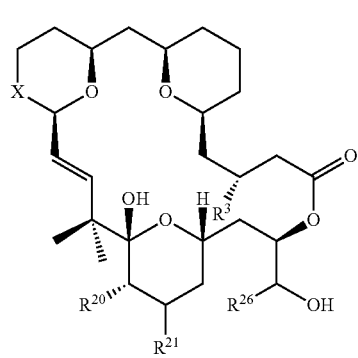

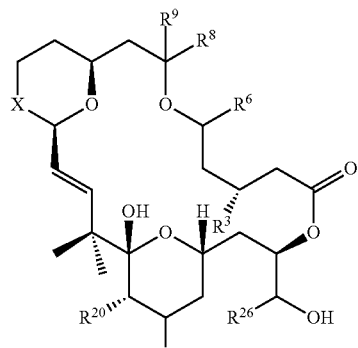

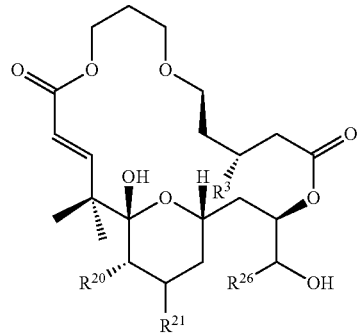

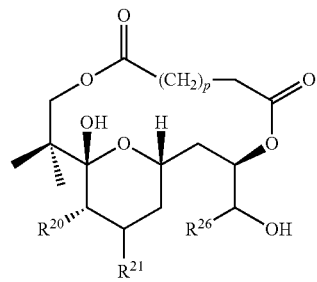

wherein:
$R^3$ is H, OH or a protecting group;
$R^6$ is H, H or $=O$;
$R^8$ is selected from the group: H, OH, R', $—(CH_2)_nO(O)CR'$ or $(CH_2)_nCO_2$-haloalkyl where n is 0, 1, 2, 3, 4 or 5;
$R^9$ is H or OH;

$R^{20}$, $R^{21}$, $R^{26}$ and R' are as defined above with respect to Formula A for bryostatin analogs;

p is 1, 2, 3 or 4; and

X is C, O, S or N—$R^e$ where $R^e$ is COH, $CO_2$R' or $SO_2$R'.

In an embodiment, the compound relates to the C26 desmethyl analogue of Formula B1:

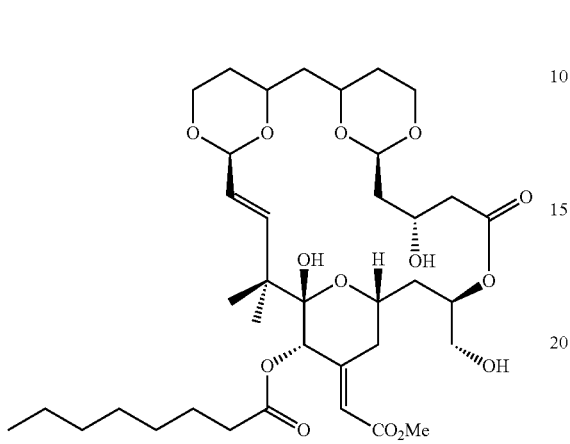

In an embodiment, the compound relates to the C26 desmethyl homologues of the native bryostatins, as illustrated in Formula F:

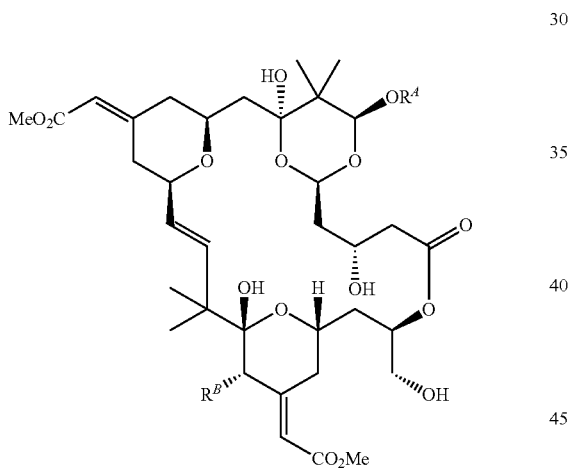

where $OR^A$ and $R^B$ correspond to the naturally occurring bryostatin substituents, including:

such as, but not limited to, C26 des-methyl Bryostatin 1, the compound of Formula F1:

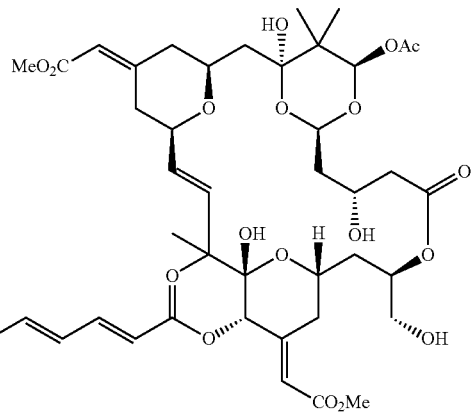

the C26 des-methyl homologues of the native bryostatins, as illustrated in Formula G:

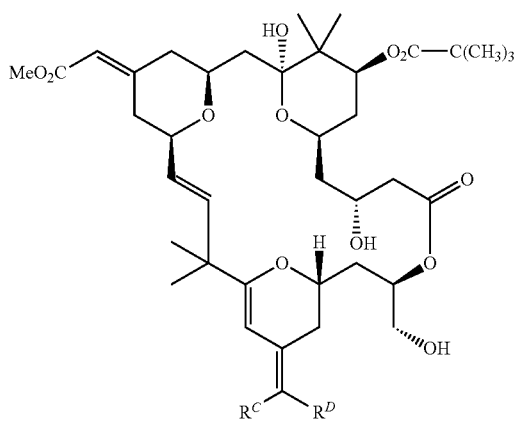

where $R^C$ and $R^D$ correspond to the naturally occurring bryostatin substituents, including:

| Bryostatin | $OR^A$ | $R^B$ |
|---|---|---|
| 1 | —$O_2$C—$CH_3$ | —$O_2$C—CH=CH—CH=CH—$CH_2$—$CH_2$—$CH_3$ |
| 2 | —OH | —$O_2$C—CH=CH—CH=CH—$CH_2$—$CH_2$—$CH_3$ |
| 4 | —$O_2$C—$CH_2$—CH($CH_3$)$_2$ | —$O_2$C—$CH_2$—$CH_2$—$CH_3$ |
| 5 | —$O_2$C—$CH_2$—CH($CH_3$)$_2$ | —$O_2$C—$CH_3$ |
| 6 | —$O_2$C—$CH_2$—$CH_2$—$CH_3$ | —$O_2$C—$CH_3$ |
| 7 | —$O_2$C—$CH_3$ | —$O_2$C—$CH_3$ |
| 8 | —$O_2$C—$CH_2$—$CH_2$—$CH_3$ | —$O_2$C—$CH_2$—$CH_2$—$CH_3$ |
| 9 | —$O_2$C—$CH_3$ | —$O_2$C—$CH_2$—$CH_2$—$CH_3$ |
| 10 | —$O_2$C—C($CH_3$)$_3$ | —H |
| 11 | —$O_2$C—$CH_3$ | —H |
| 12 | —$O_2$C—$CH_2$—$CH_2$—$CH_3$ | —$O_2$C—CH=CH—CH=CH—$CH_2$—$CH_2$—$CH_3$ |
| 13 | —$O_2$C—$CH_2$—$CH_2$—$CH_3$ | —H |
| 14 | —$O_2$C—C($CH_3$)$_3$ | —OH |
| 15 | —$O_2$C—$CH_3$ | —$O_2$C—CH=CH—CH=CH-C(OH)H—$CH_2$—$CH_3$ |
| 18 | —$O_2$C—C($CH_3$C)$_3$ | —H |

| Bryostatin | $R^C$ | $R^D$ |
|---|---|---|
| 16 | —H | —CO$_2$Me |
| 17 | —CO$_2$Me | —H | and to the C26 des-methyl homologues of the native Bryostatin 3, as illustrated in the following Formula H:

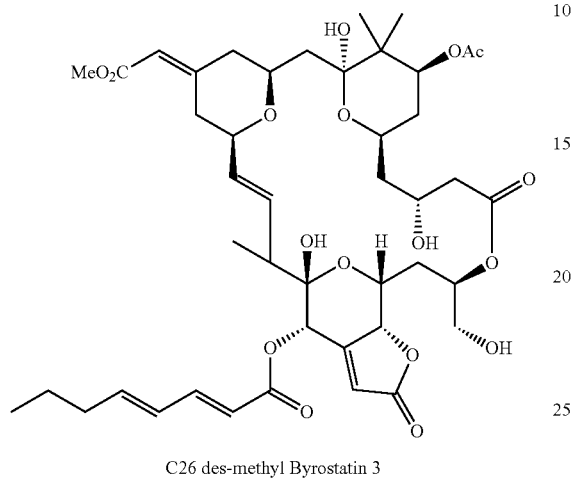

C26 des-methyl Byrostatin 3

Excluded from the scope of the bryostatin analogues is of Formula i (where $R^3$ is H or OH) and the analogue of Formula J:

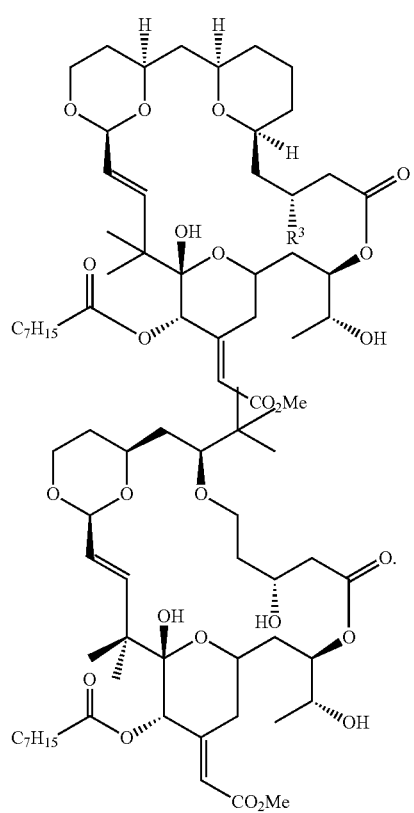

Additional embodiments of bryostatin analogs include compound described by the following formula:

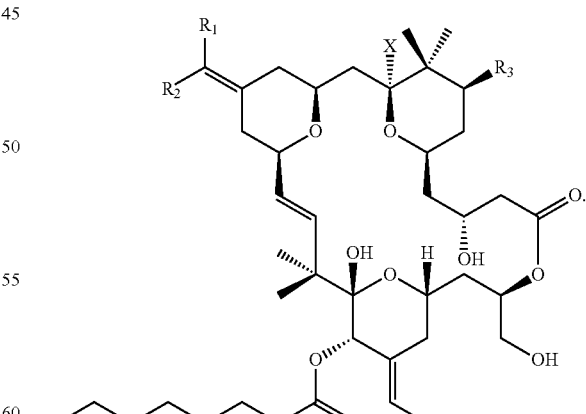

Each R, R1, and R2 can each be independently selected from alkyl, aryl, acyl, sulfonyl, and phosphonyl and in particular hydrogen, methyl, and ethyl. W can be selected from CH$_2$, O, NH, and NR. Y can be selected from alkyl, alkenyl, alkynyl, aryl, NH-alkyl, NH-alkenyl, and Nh-aryl. X can be selected from OH, F, and O-alkyl. R3 can be selected from OAc, O-ester, OH, Oalkyl, O-aryl, OCONH-alkyl, OCONH-aryl, and OCONH-alkenyl. Z can be selected from hydrogen, methyl, ethyl, iPr, and aryl.

In an embodiment the bryostatin analogs can include compound described by the following formula:

$R_1$ = H, CO$_2$Me
$R_2$ = H, CO$_2$Me
$R_3$ = H, OH, OAc
X = H, OH

In an embodiment the bryostatin analogs can include the following compounds:

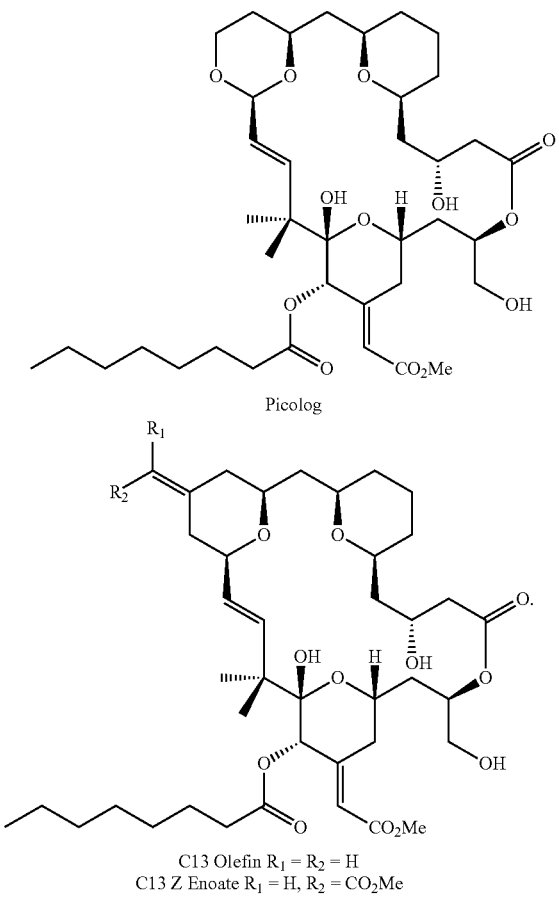

Picolog

C13 Olefin R$_1$ = R$_2$ = H
C13 Z Enoate R$_1$ = H, R$_2$ = CO$_2$Me

As noted above, prodrugs of bryostatin are similar to those described in reference to prostratin.

Synthesis

In an embodiment, the present disclosure describes synthetic methods for preparing the above-mentioned C13 analogs. A method for synthesizing some C13 analogs is disclosed in Wender et al., Ser. No. 12/178,860, filed: Jul. 24, 2008, which is specifically incorporated herein by reference, as setting forth synthetic methods yielding C13 analogs of prostratin. The present C13 synthetic method employs an alcohol intermediate compound termed "prostratinol," or 13-prostratinol or 12-deoxy-20-triphenylmethyloxy phorbol, which has the structure of prostratin (or the desired analog final compound) except for a hydroxyl at C13.

Reactions were run at 20° C. unless otherwise stated. The pH was controlled by the reaction conditions and not checked or adjusted unless otherwise.

Figure 3A:
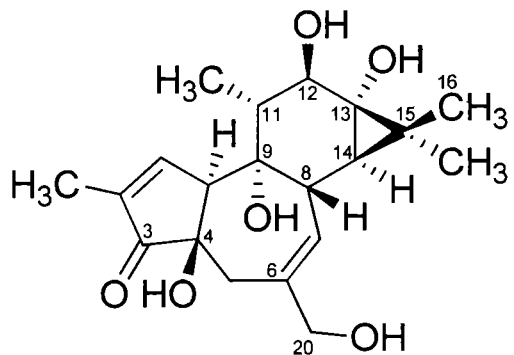
FIGS. 3A-3C are schematic representations illustrating a synthetic method for producing prostratinol and C13 analogs from C13 prostratinol (compound 31).
Figure 3A:
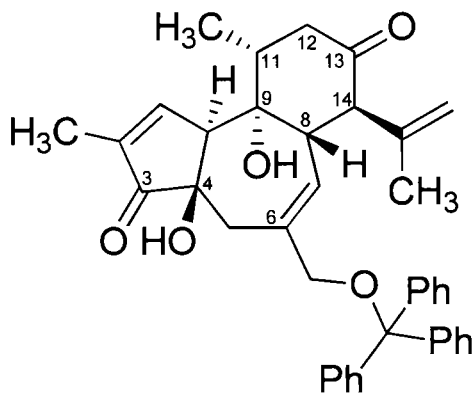
Figure 3B:
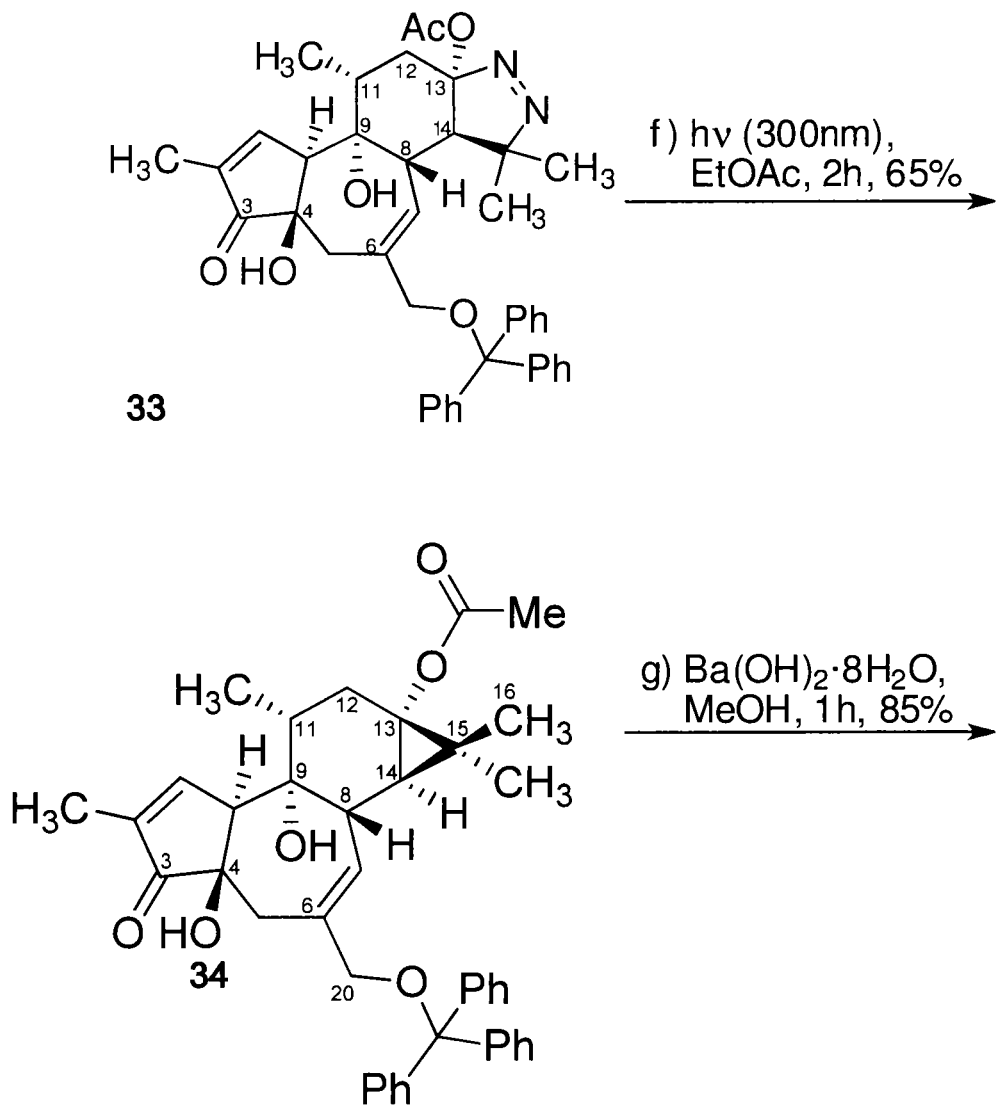
Figure 3C:
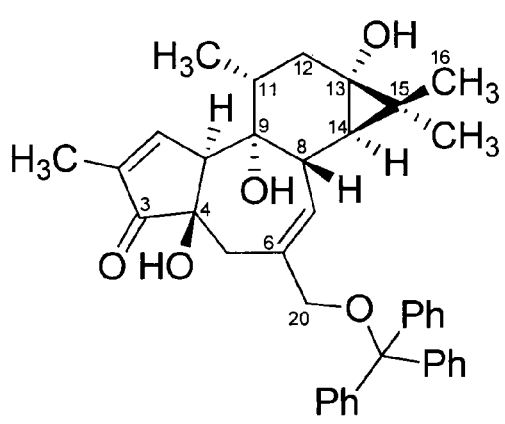
Figure 3C:
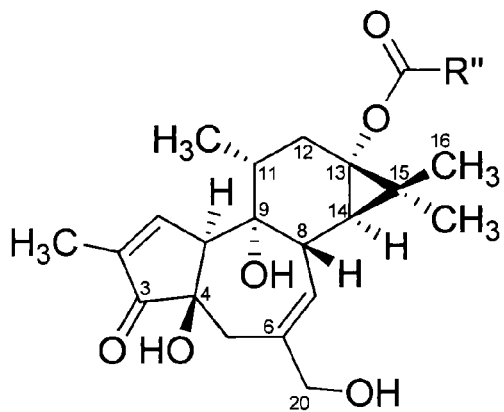
Figure 4:
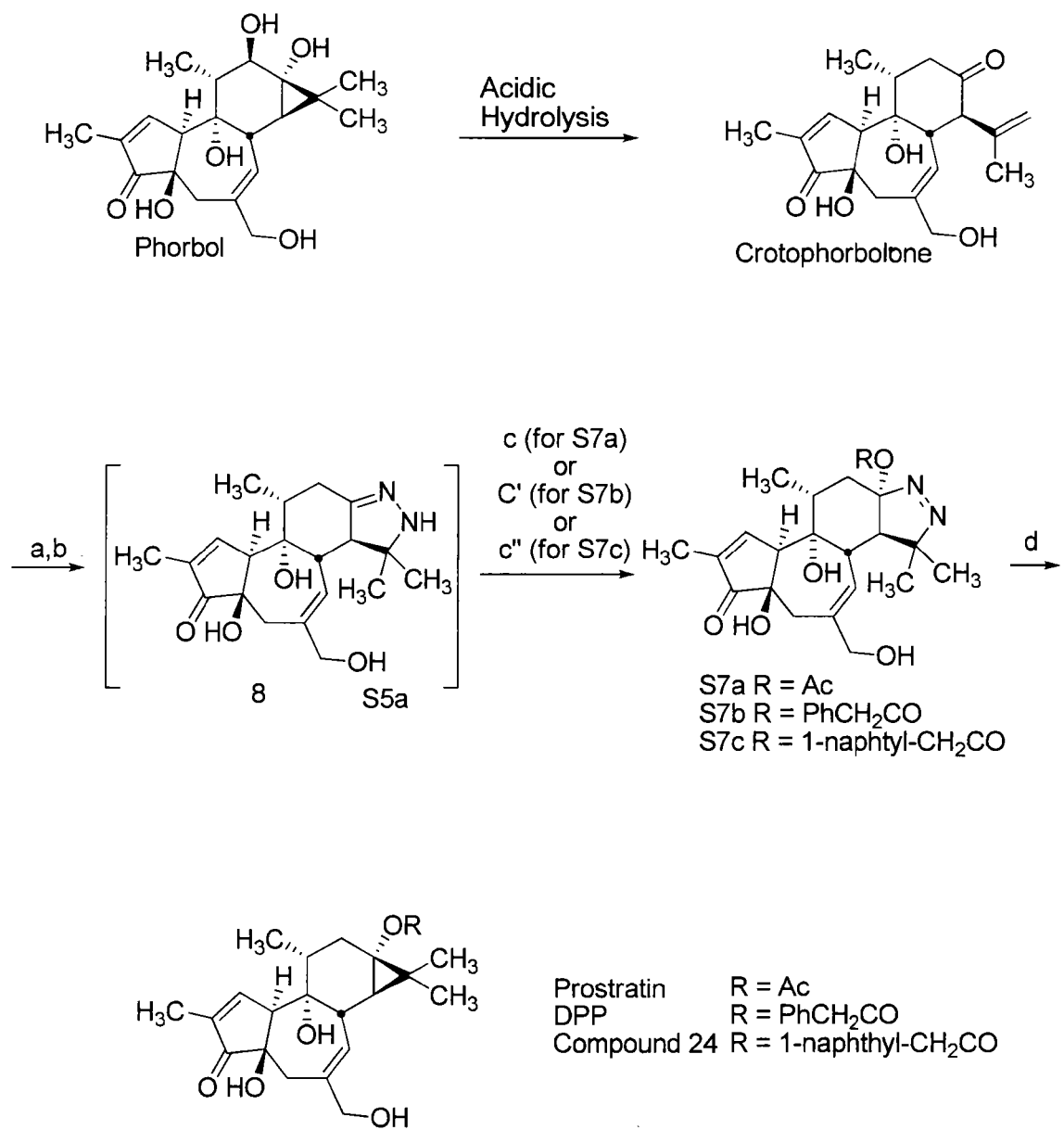
FIG. 4 is a schematic representation for another method for producing C13 analogs. It is taken from copending U.S. application Ser. No. 12/178,860 filed Jul. 24, 2008 by Wender et al., which illustrates a preparative method for crotophorbolone and also for prostratin, DPP and C13-prostratinol, where the C13 functional group is indicated generally as "RO." R is Ac when $Pb(OAc)_4$ is used without additional acid added (prostratin) as illustrated in step c or, R is $PhCH_2CO$ when phenylacetic acid is used in combination with $Pb(OAc)_4$ (DPP) as illustrated in step c', and as taught in the prior application.

In an embodiment, phorbol is first converted to crotophorbolone, the reactive C20 hydroxyl group in crotophorbolone is then protected, and the compound converted into C20 triphenylmethyloxy prostratinol and the C13 OH can then be coupled with a variety of acids (e.g., cyclohexylacetic acid, biphenylacetic acid, or benzoic acid) to produce C13 analogs. Methods for producing different C13 analogs are shown in FIGS. 3A-3C (proceeding through compounds shown at 31-36). Methods for producing different C13 analogs are also shown in FIG. 4, which is a published method. Methods for producing different C12 and C13 analogs are also shown at FIG. 5, which further illustrates use of a derivatized protected prostratinol intermediate.

In another embodiment, the present disclosure relates to methods for synthesizing novel C12 analogs. These methods employ a prostratin-like compound that has a hydroxyl group at the 12 position. As before, the C20 hydroxyl is protected, and various acids (e.g., cyclohexylacetic acid, biphenylacetic acid, or benzoic acid) and coupling partners (e.g., chlorobenzo[d]thiazole, benzoyl chloride, or phenylcarbamic chloride) may be used to esterify and modify the hydroxyl at the C13-position, enabling a variety of novel compounds having PKC activation activity. The C12-hydroxyl group is then converted into an ether, e.g., a methyl ether by treatment with methyl trifluoromethanesulfonate. The resultant C12 ethers are potent PKC binders.

The following sections describe phorbol ester synthetic methods for accessing C13 analogs and C12 analogs in greater detail.

The following describes the synthesis of C13 analogs. In particular, the following describes the synthesis using a C20 protected crotophorbolone (FIG. 1 and FIGS. 3A-3C). FIG. 1 illustrates a summary of the method of Example 1. Briefly, the steps show the following: a. 0.01 M H$_2$SO$_4$, 90° C., 1 h, 40%; b. triphenylmethyl chloride, pyridine, 23° C., 12 h quantitative; c. N$_2$H$_4$XH$_2$O, AcOH, MeOH, 23° C., 2 h; d. toluene, iPr$_2$NEt, 150° C.; e. Pb(OAc)$_4$, CH$_2$Cl$_2$, 0° C., 45%; f. hv (300 nm), EtOAc, 2 h, 65%; g. Ba(OH)$_2$.8H$_2$O, MeOH, 1 h, 85%; h. R1=R1COOH, 1-ethyl-3-(3-dimethylaminopropyl) carbodiimide hydrochloride, DMAP, THF, 23° C., 12 h 80-99%; and i. HClO$_4$, MeOH, 23° C., 40 min, 89-99%.

The present methods involve the preparation of an intermediate, C12-deoxy-C13-(phenylacetyl)-C20-trityl phorbol ("C20-Trityl Prostratinol") 35, having a C13 alcohol and protection of the hydroxyl group at C20, e.g., as a triphenylmethyl ('trityl') ether. C13 OH may then be reacted with a variety of reactive groups, such as carboxylic acids to produce C13 analogs. The protective group is removed to produce, e.g., C20-OH as in prostratin. These methods are illustrated in FIG. 3A through 3C.

The method begins with a known starting material, phorbol, compound 31. Phorbol is heated in the presence of sulfuric acid (other acids such as, but not limited to, hydrochloric acid, triflic acid, phosphoric acid could be used) to generate crotophorbolone. Crotophorbolone is protected at C20 according to a standard reaction with TritylCl ('TrCl') and pyridine, at 55° C. to give rise to compound 32. In step c, compound 32 is treated with hydrazine to produce the corresponding C13-hydrazone. In step d the product is subjected to cyclization. In step e the pyrazoline is subjected to oxidation; and in step f to cyclopropane ring formation, to yield compound 34. In step g, compound 34 is subjected to hydrolysis. In step h, the product of step g, C20-Trityl Prostratinol 35, is subjected to esterification. In step i, the C20 position is deprotected to yield compound 36. As can be seen, compound 36 is a C13 prostratin analog. R" may be selected by the acid component of esterfication reaction of step h.

Another method for preparing a prostratinol compound starts with crotophorbolone, the synthesis of which is shown in FIG. 4, taken from FIG. 8 of the above referenced Ser. No. 12/178,860 and further described in Science 320(5876):649-652 (2 May 2008).

An exemplar phorbol oxidation route is described in FIG. 4. Phorbol can be converted to prostratin in a variety of ways. In one embodiment, the synthesis occurs as shown in FIG. 4. In this method, described more fully in copending U.S. application Ser. No. 12/178,860, and in Science 320(5876):649-

652 (May 2008), which are both incorporated herein by reference, phorbol is converted to crotophorbolone. An intermediate diamino ring structure (pryazoline) is formed as shown at compound 8. This is reacted with various R groups to provide a C13 substitution with various acids in the presence of Pb(OAc)$_4$ to provide a C13 substitution. Then, the diamino ring structure is rearranged to produce the cyclopropyl ring as present in prostratin type compounds.

FIG. 5 describes a synthetic method beginning with crotophorbolone and using hydrobromination. As can be seen, C12 methoxy is prepared and a C13 ester may have a substituted R2. R2 corresponds to Formula I where X═O and R1═—C (═O)-aryl, biaryl, fused aryl, branched alkyl or cycloalkyl.

The method of FIG. 5 begins with phorbol. Phorbol is protected at the C20 position as a triphenylmethyl ether that can be accessed as also described in step a and also in FIG. 4. In step b, esterification with acetic acid or another acid, e.g. cyclohexylacetic acid, biphenylacetic acid, benzoic acid, in the presence, e.g., of a carbodiimide coupling reagent or treatment with acid chloride in the presence of a non-nucleophilic amine base leads to the formation of a C13-actetate. In step c, treatment of the compound with methyl trifluoromethansulfonate or under other methylating or alkylating conditions in the presence of a non-nucleophilic base such as of 2,6 di-tert-butyl-4-methylpyridine or of 2,6 di-tert-butyl-pyridine gives 12-methoxy-13-acetoxy-20-triphenylmethyl phorbol. In step d, this is then de-protected to yield the C20 hydroxyl compound 76 that is the C12-methylether-analog of prostratin or 12-methoxyprostratin. The selection of the alkylating agent (e.g., methyl triluoromethanesulfonate, triethyloxonium tetrafluoroborate, or benzyl chloride) will determine the identity of the resulting C12 substituent.

In an analogous fashion, other C12-methoxy-C13-esters as analogs of C12-methoxy prostratin and prostratin can be accessed. The synthesis begins with phorbol as shown in FIG. 5. Phorbol is protected at the C20 position as a triphenylmethyl ether which can be accessed as also described in step a and also in FIG. 4. In step b, esterification with an acid R2COOH in the presence of for example, but not limited to, a carbodiimide coupling reagent or treatment with acid chloride or similar reagent in the presence of a non-nucleophilic amine base leads to the formation of a C13-ester. In step c, treatment of the compound with methyl trifluoromethansulfonate or under other methylating or alkylating conditions in the presence of a non-nucleophilic base such as, but not limited to, 2,6 di-tert-butyl-4-methylpyridine or 2,6 di-tert-butyl-pyridine gives 12-methoxy-13-acetoxy-20-triphenylmethyl phorbol. In step d, this is then de-protected to yield the C20 hydroxyl compound 76 which is the C12-methylether-analog of C13-ester prostratin or 12-methoxy-C13-ester-prostratin derivatives.

Referring now to FIGS. 6A-6B, other C12-methoxy-C13-esters as analogs of C12-methoxy prostratin and prostratin can be accessed similarly to the synthesis of C13-prostratin analogs as described in FIG. 1. This exemplary synthesis of C13 analogs of C12-methoxy prostratin begins with phorbol as shown in FIG. 6A. Phorbol is protected at the C20 position as a triphenylmethyl ether that can be accessed as also described in step a and also in FIG. 4. In step b, esterification with acetic acid in the presence of, for example, but not limited to, a carbodiimide coupling reagent (e.g., dicyclohexylcarbodiimide, or 3-ethyl-1(N,N-dimethyl)aminopropylcarbodiimide) or treatment with acetyl chloride or similar reagent in the presence of a for example, but not limited to, non-nucleophilic amine base (e.g., triethylamine, diisopropylethylamine, or pyridine) leads to the formation of the C13-acetate. In step c, treatment of compound 72 with methyl trifluoromethansulfonate or under other methylating or alkylating conditions in the presence of, but not limited to, a non-nucleophilic base such as a base of 2,6 di-tert-butyl-4-methylpyridine or of 2,6 di-tert-butyl-pyridine gives 12-methoxy-13-acetoxy-20-triphenylmethyl phorbol. The use of different alkylating agents other than methyl trifluoromethansulfonate or different methods leading to C12-O-alkylated species may be used to prepare other C12 analogs. In step d, the C13 acetate is removed through ester hydrolysis to give 12-methoxy-20-triphenylmethyl-phorbol. In step e, esterification with an acid R2COOH in the presence of for example, but not limited to, a carbodiimide coupling reagent or treatment with acid chloride or similar reagent in the presence of a non-nucleophilic amine base leads to the formation of a C13-ester as in the method of FIG. 5. In step f, this is then de-protected to yield the C20 hydroxyl compound 76 that is the C12-methoxyr-analog of C13ester prostratin or 12-methoxy-C13-ester-prostratin derivatives.

Given the methodology described here, alternatives to the examples given may be employed.

Figure 7:
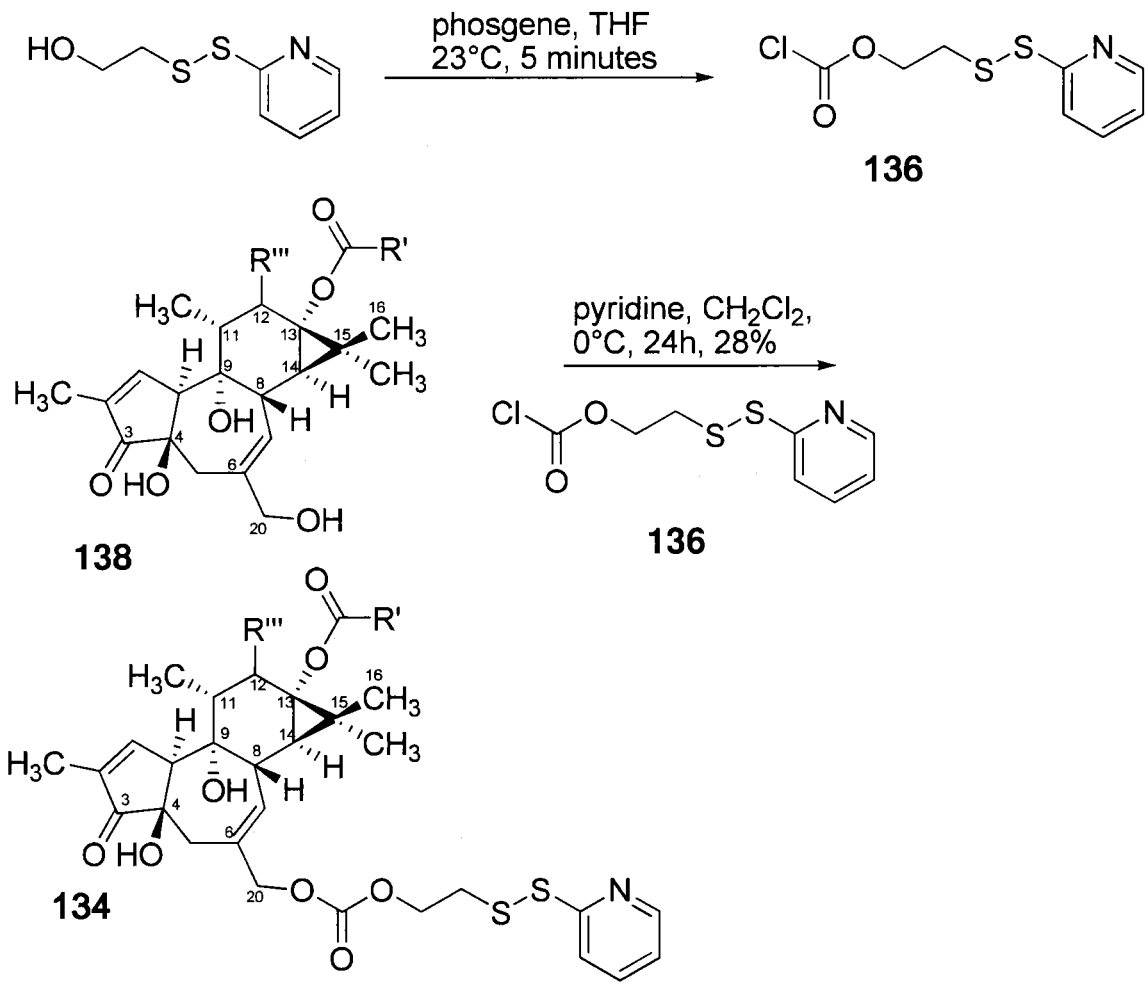
FIGS. 7A-7C are schematic representations of methods for making an exemplary phorbol ester prodrug including an ester, an ester and disulfide linkages, and further including an oligopeptide (eight arginine residues).
Figure 7:
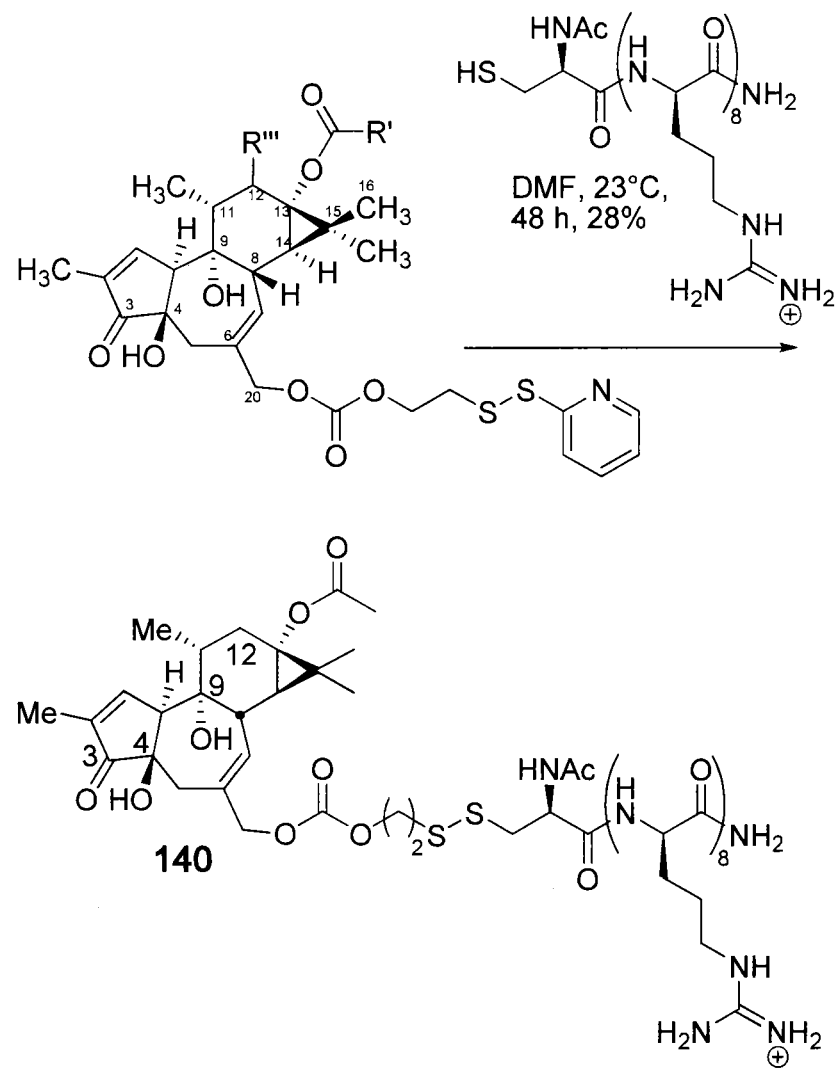
Figure 7:
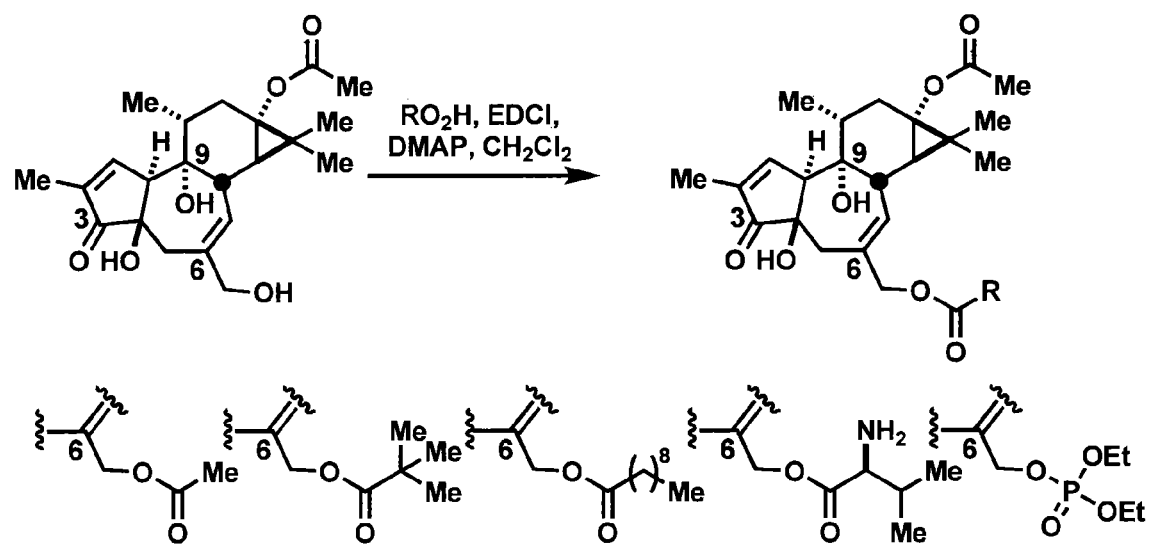
Figure 8A:
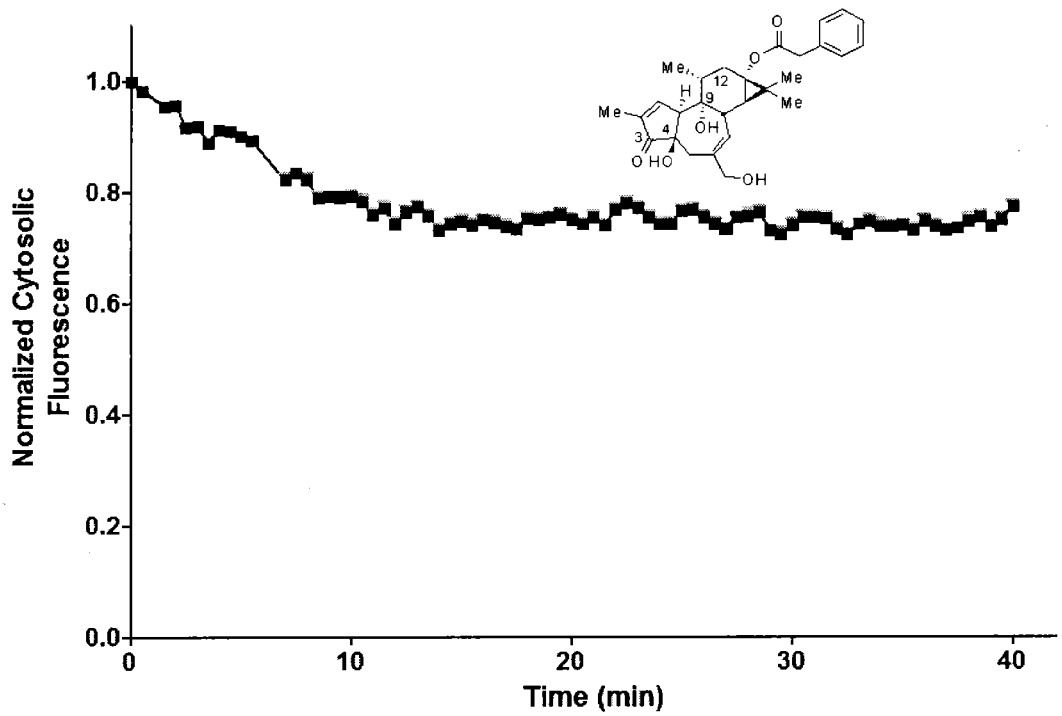
FIGS. 8A-8D show graphs that illustrate PKC-GFP translocation activity for various compounds.
Figure 8B:
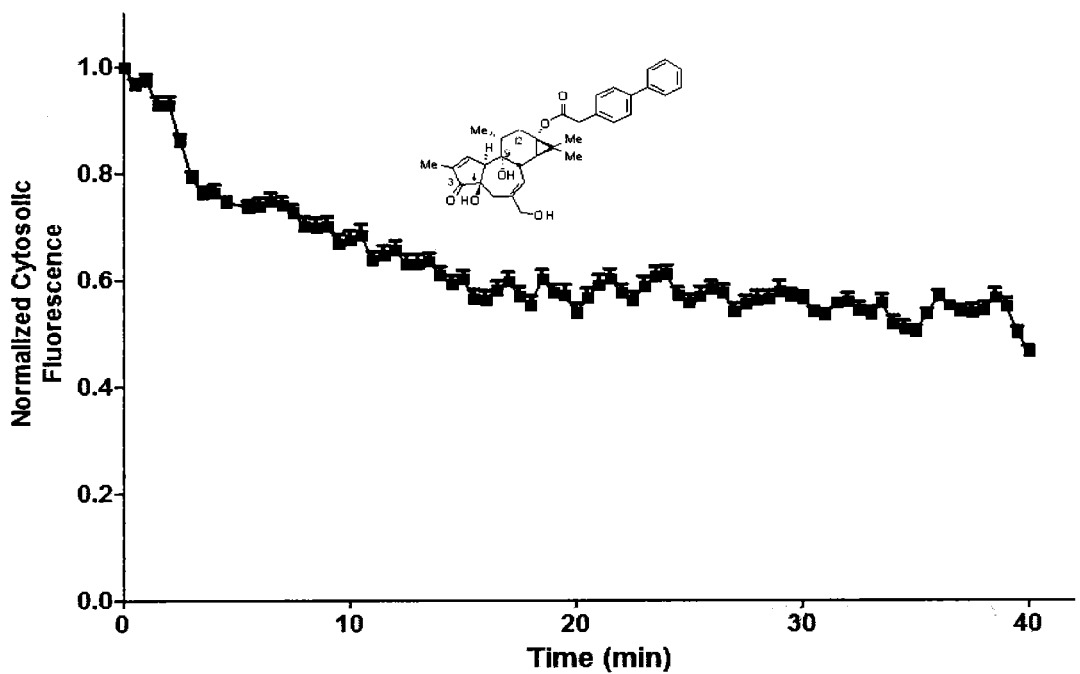
Figure 8C:
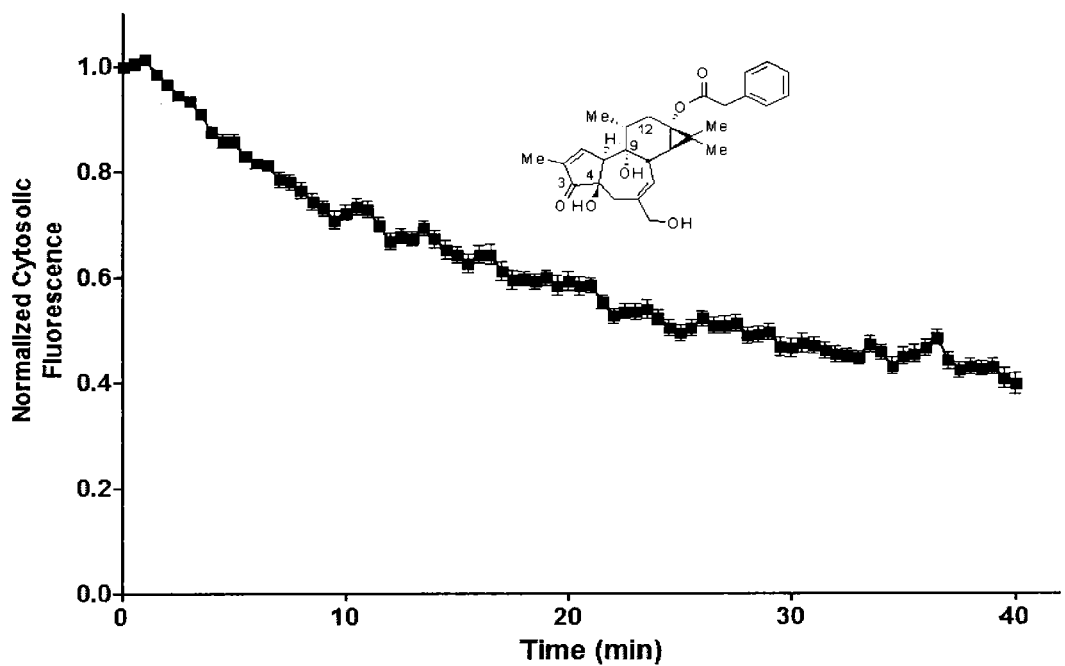
Figure 8D:
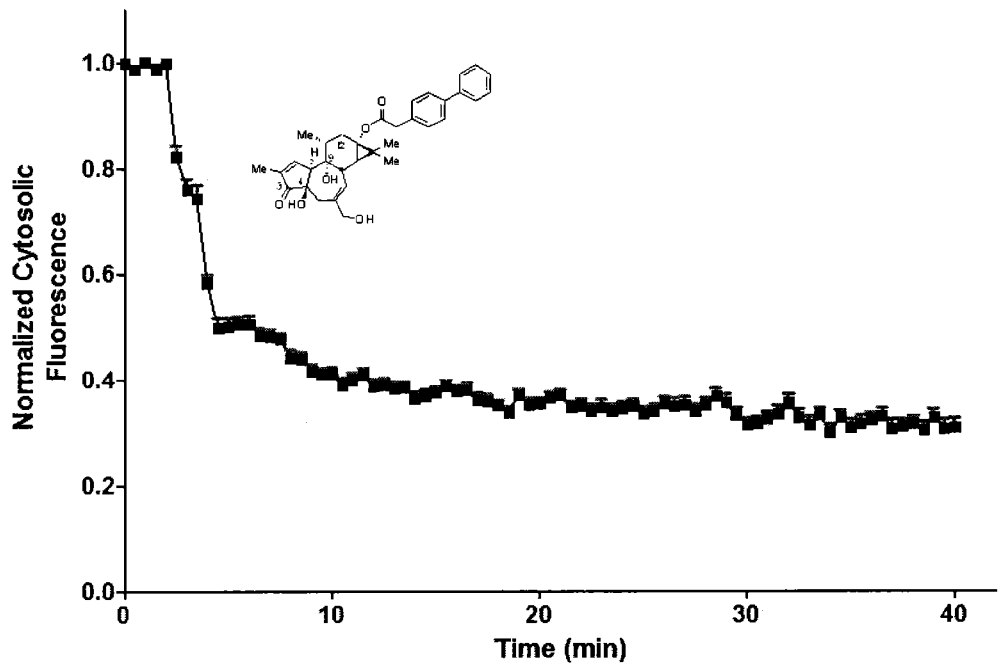

In addition, one may prepare the present compounds as prodrugs. FIGS. 7A to 7C illustrate the synthesis of 12-deoxy phorbol ester prodrugs. Prodrugs of prostratin and the novel compounds disclosed here are advantageous in that many of the present compounds may be, and prostratin is known to be, inflammatory at the site of administration (e.g., injection). Since the present compounds activate PKC, they may be expected to cause inflammation at the site of administration, i.e., injection. By preparing a prodrug that does not have PKC activation activity, the compound may be diffused through the body while it is being activated, lessening the acute inflammatory response and enabling a more rapid administration, such as a bolus injection rather than a prolonged drip.

An alteration in the C20 (R2 substituent in Formula I) is employed to provide a group in place of the C20 hydroxyl or as a substituent of the C20-oxygenation that is required for activity, yet is processed in vivo to produce the C20 hydroxyl. As shown in FIG. 7A, a 2-thiopyridine connected through a disulfide linkage to an alkyl alcohol, is reacted with phosgene or an equivalent thereof, for example, but not limited to, triphosgene to produce the corresponding alkylcarbono chloridate, compound 136. This is linked to the hydroxyl group at C20 of a prostratin or prostratin analog compound 138, in step 2. Then, in step 3, shown in FIG. 7B, the product of step 2 is reacted with AcNH-D-Cys-(DArg)8CONH$_2$ in DMF, for 48 hr to produce in 28% yield compound 140. This compound has been shown to convert to the parent prostratin or prostratin analog within two minutes with full release after 15 minutes. The disulfide group facilitates cleavage of the carbonate structure to yield the C20 alcohol. The method may be generally applicable to carbonates and similar groups where the carbonate comprises instead the general structure —O—C(═O)—O—R, where the O is attached to the C20 carbon and the R may be a variety of alkyl, aryl and heteroaryl groups.

Figure 9:
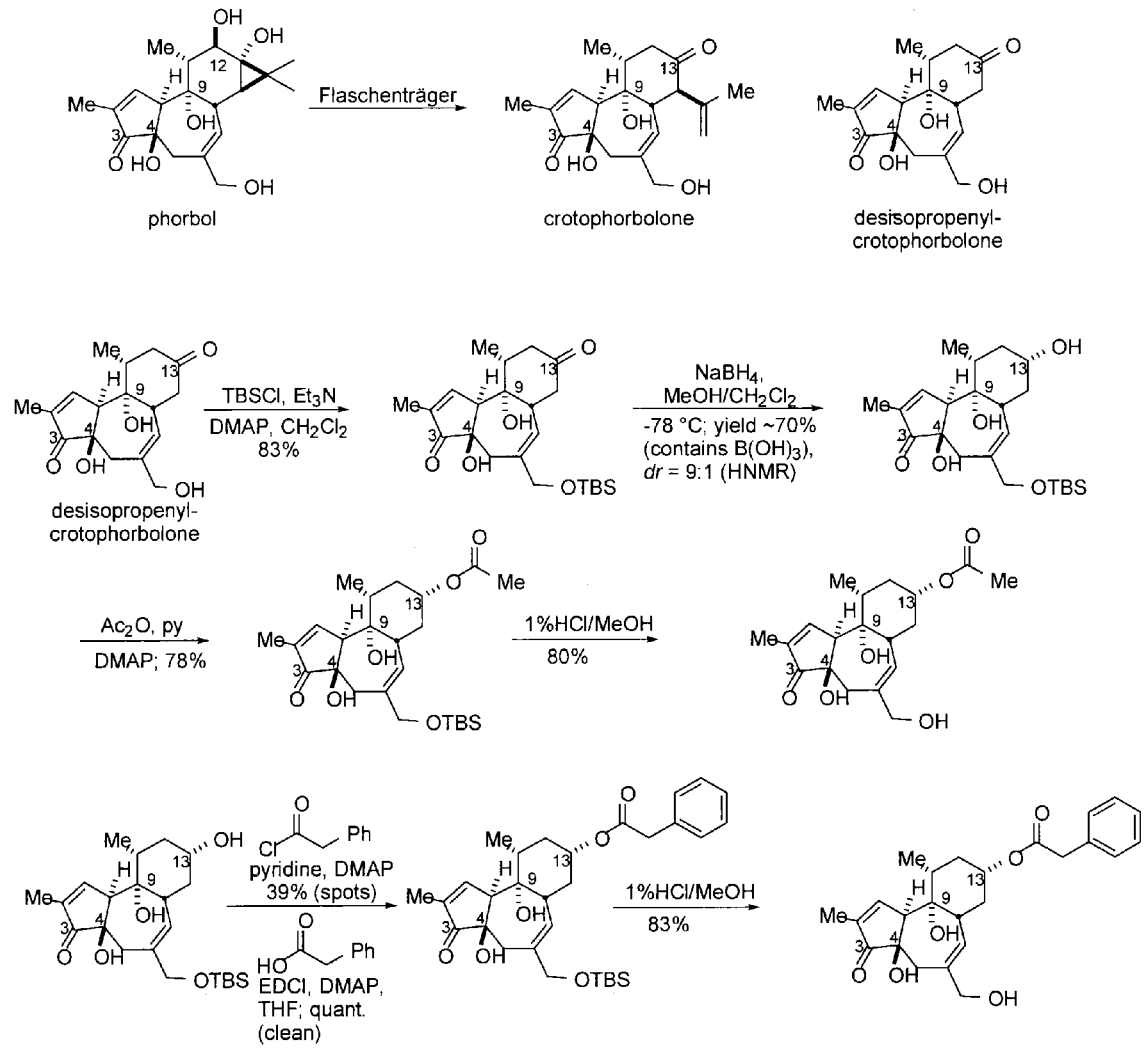
FIG. 9 illustrates an exemplar synthesis for compound represented by Formula IV' and IV".
Figure 9:
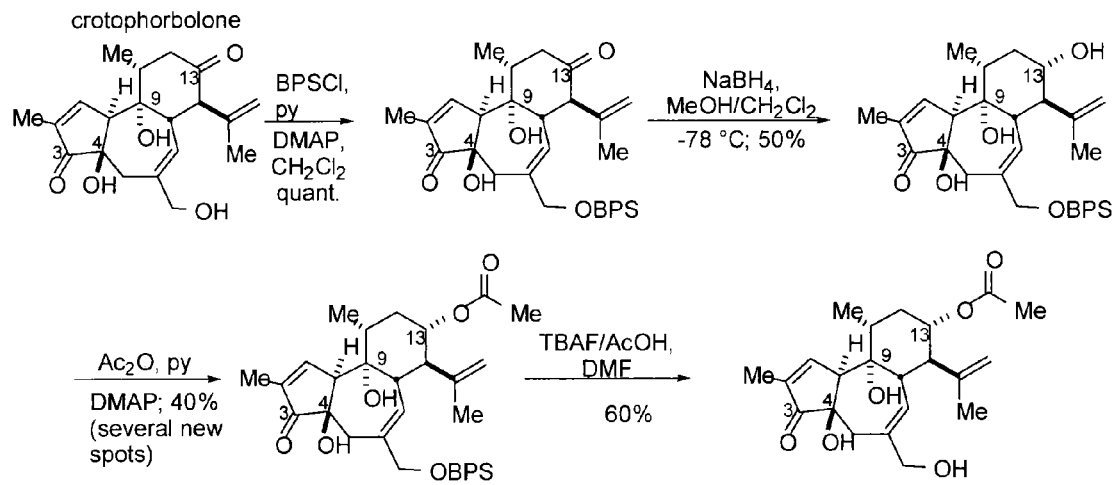

Formulae IV' and IV" can be formed using the synthesis illustrated in FIG. 9. FIG. 9 describes a method of synthesis for analogues, derived from crotophorbolone and desisopropenylcrotophorbolne, lacking the cyclopropane ring. In this method phorbol is converted into crotophorbolone and desisopropenylcrotophorbolone by exposure to acid. Desisopropenylcrotophorbolone was protected as its C20 silyl ether and reduced with sodium borohydride to give the corresponding C13-α-alcohol. The C13 alcohol was acylated in this case with acetic anhydride to give the C13-acetate and then deprotected a C20 to produce a acetate analogue. Another example for this method is the esterification of the C13 alcohol with phenylacetic acid using either the acid chloride or the acid in conjunction with a coupling agent like 1-ethyl-3-[3-(dimethylamino)-propyl]carbo-diimide. Deprotection at C20 gives rise to a phenylacetate analogue. Crotophorbolone is protected as its C20-silyl ether and then reduced with sodium borohydride to give the C13-α-alcohol. The alcohol can be esterified with acetic anhydride to give the corresponding C13-ester followed by deprotection at C20- to give a acetate analogue.

Figure 10:
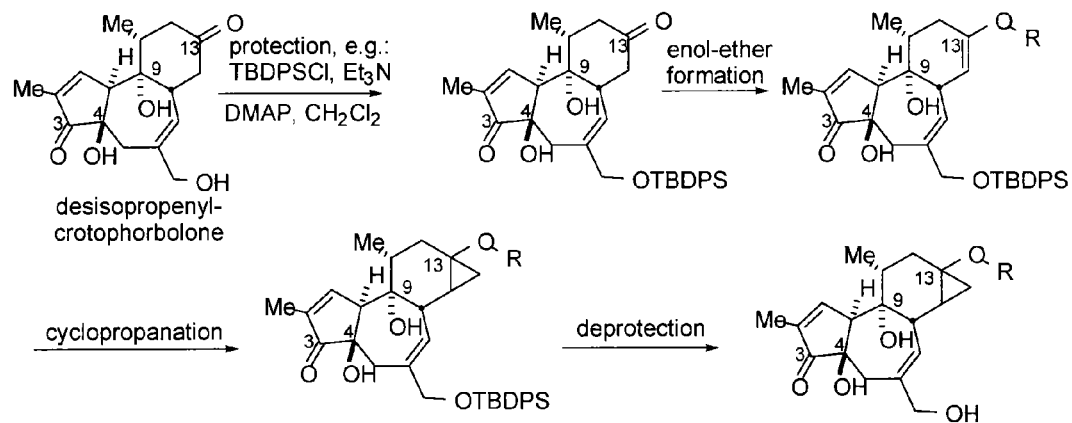
FIG. 10 illustrates an exemplar synthesis for compounds represented by Formula V.

Formula V can be formed using the synthesis illustrated in FIG. 10. FIG. 10 describes a method that could be used for the synthesis of C15-desdimethyl analogs of prostratin. The method uses desisopropenylcrotophorbolone which can be accessed from phorbol as previously taught, e.g., FIG. 9. Desisopropenylcrotophorbolone is protected as a silyl ether at C20 and then converted into an C14, C13-enolether by treatment with e.g., triethylamine and acetic anhydride or pyridine and acetyl chloride. The C13, C14 alkene is converted into a cyclopropane by treatment with e.g., diiodomethane and zinc or diiodomethane and samarium(II) iodide. Deprotection of the silylether at C20 then gives an acetyl analogue.

Figure 11:
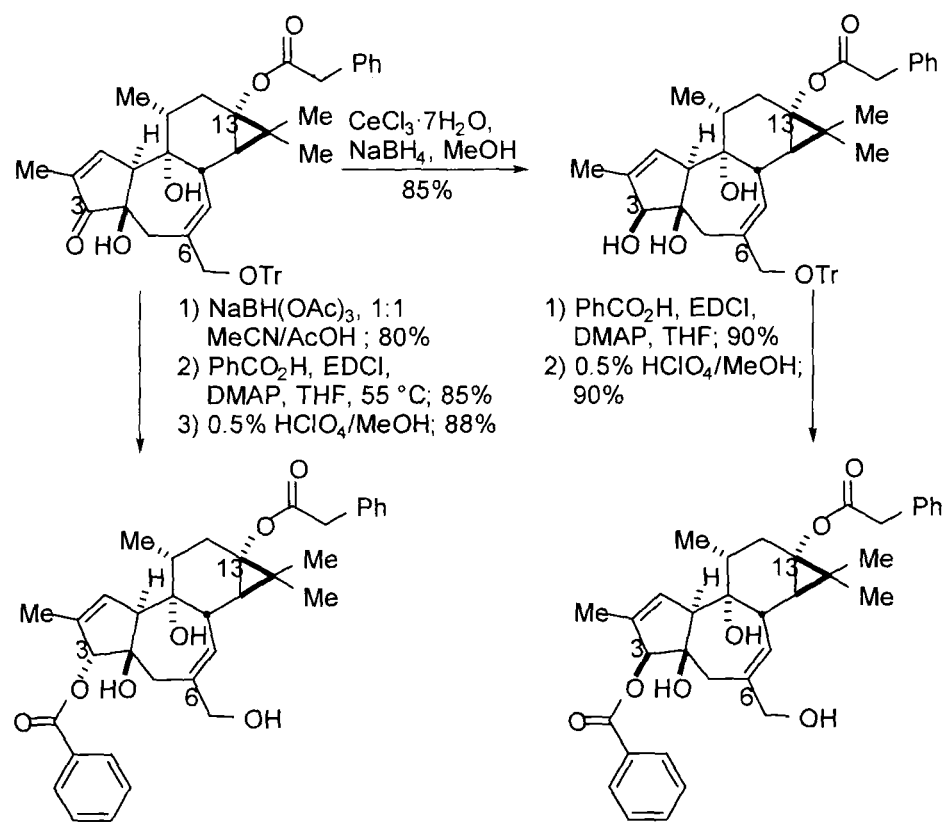
FIG. 11 illustrates an exemplar synthesis for compounds represented by Formula VI' and VI".
Figure 12A:
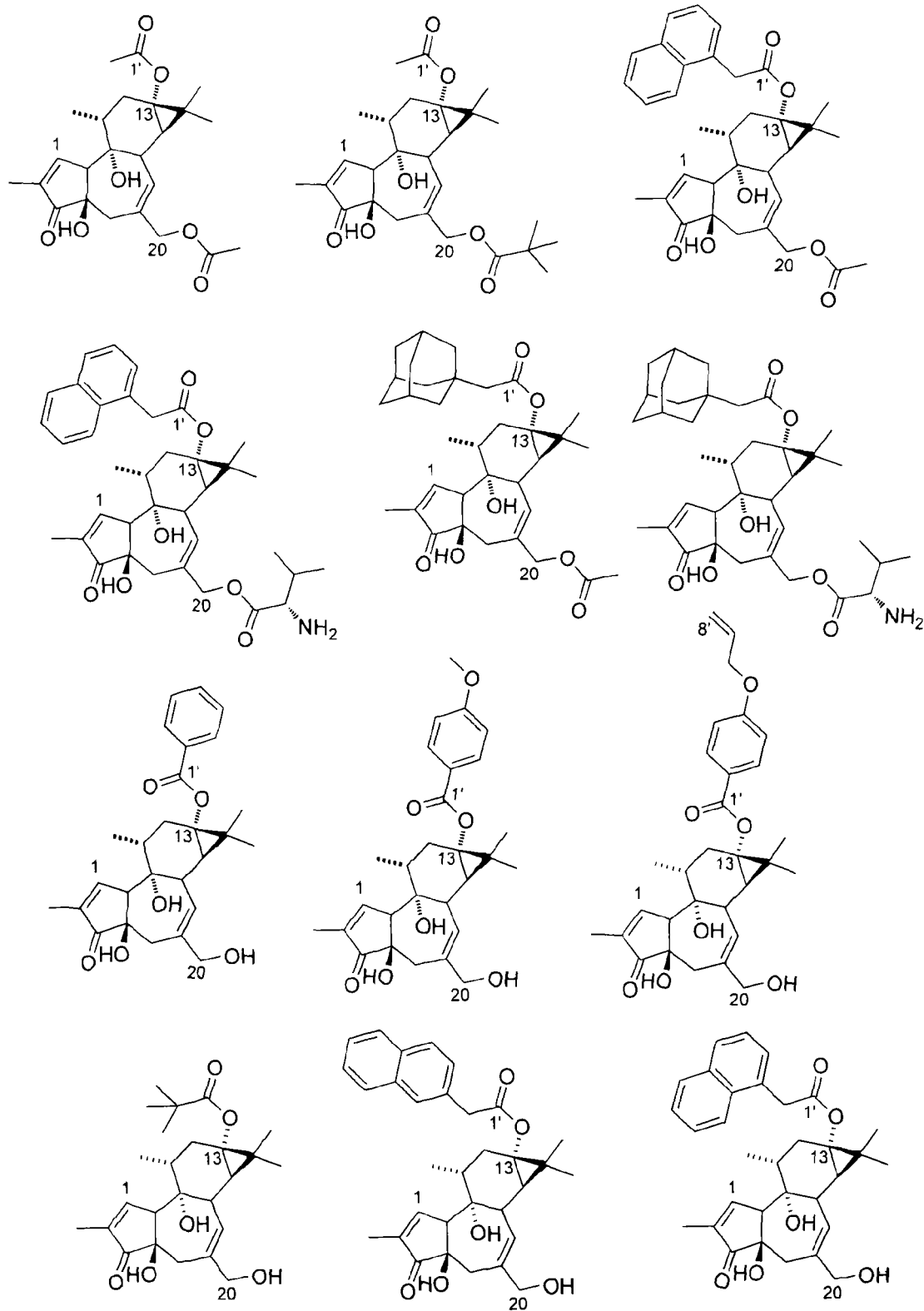
FIGS. 12A to 12E illustrate various specific compounds of the present disclosure.
Figure 12B:
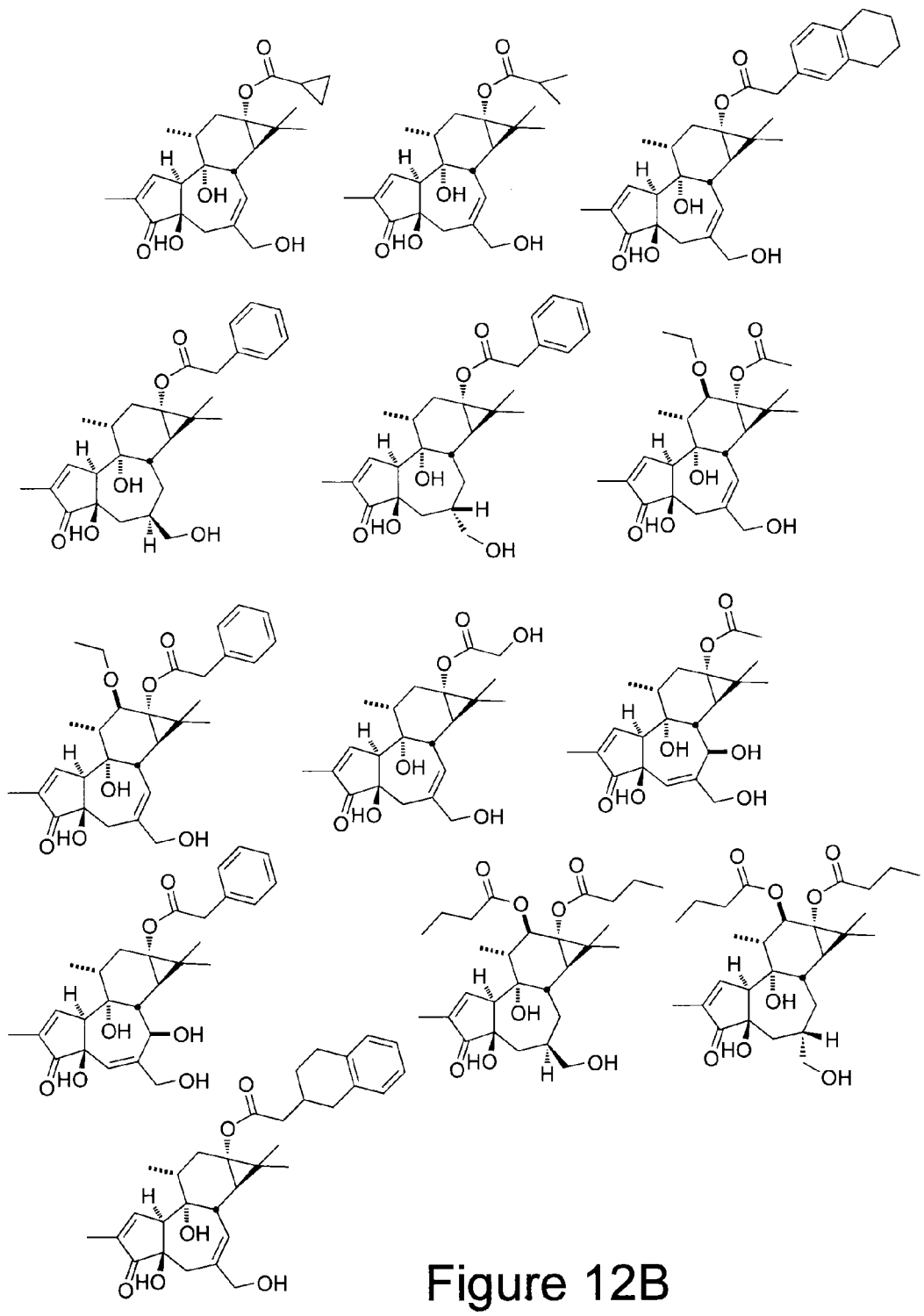
Figure 12C:
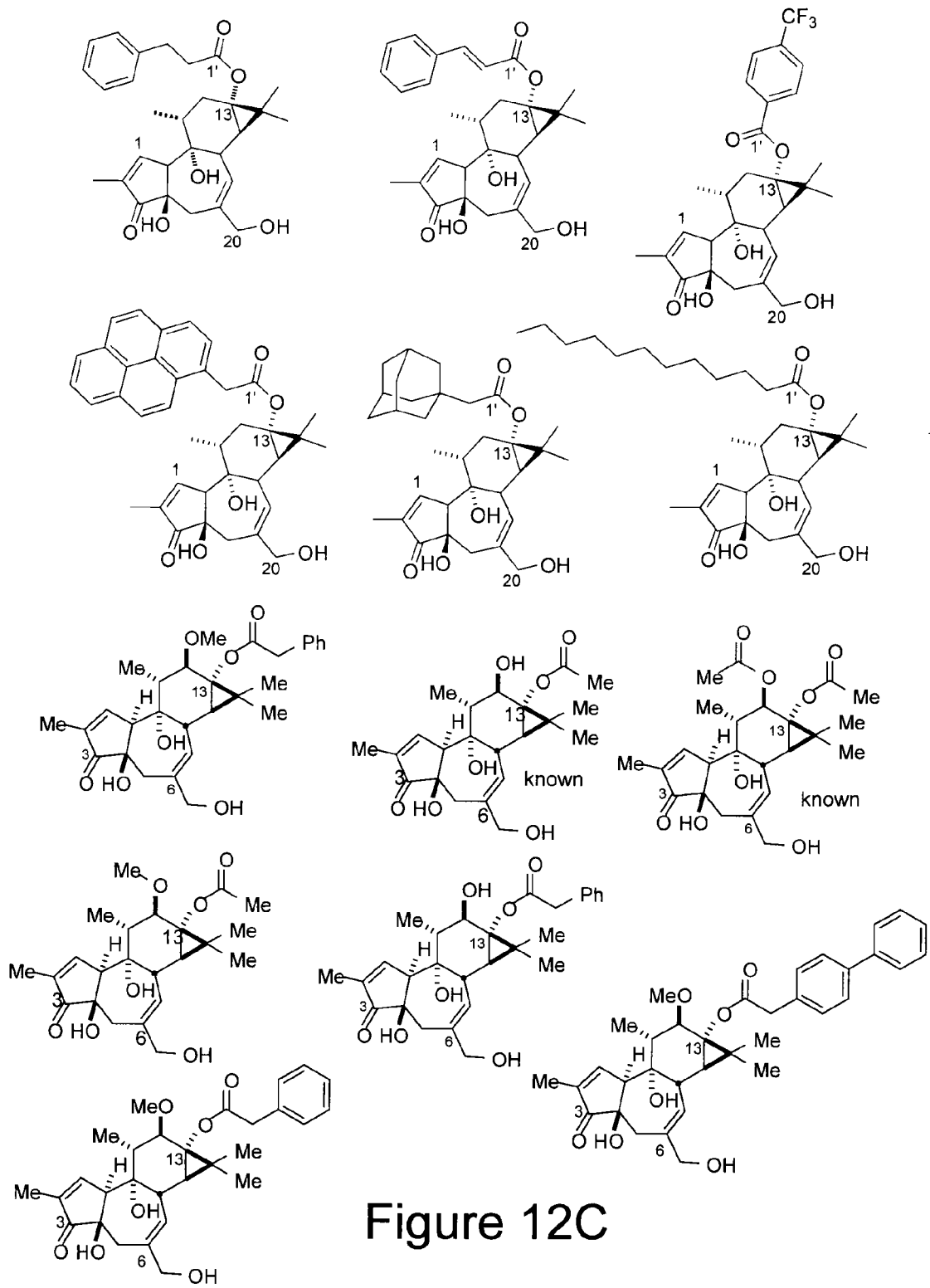
Figure 12D:
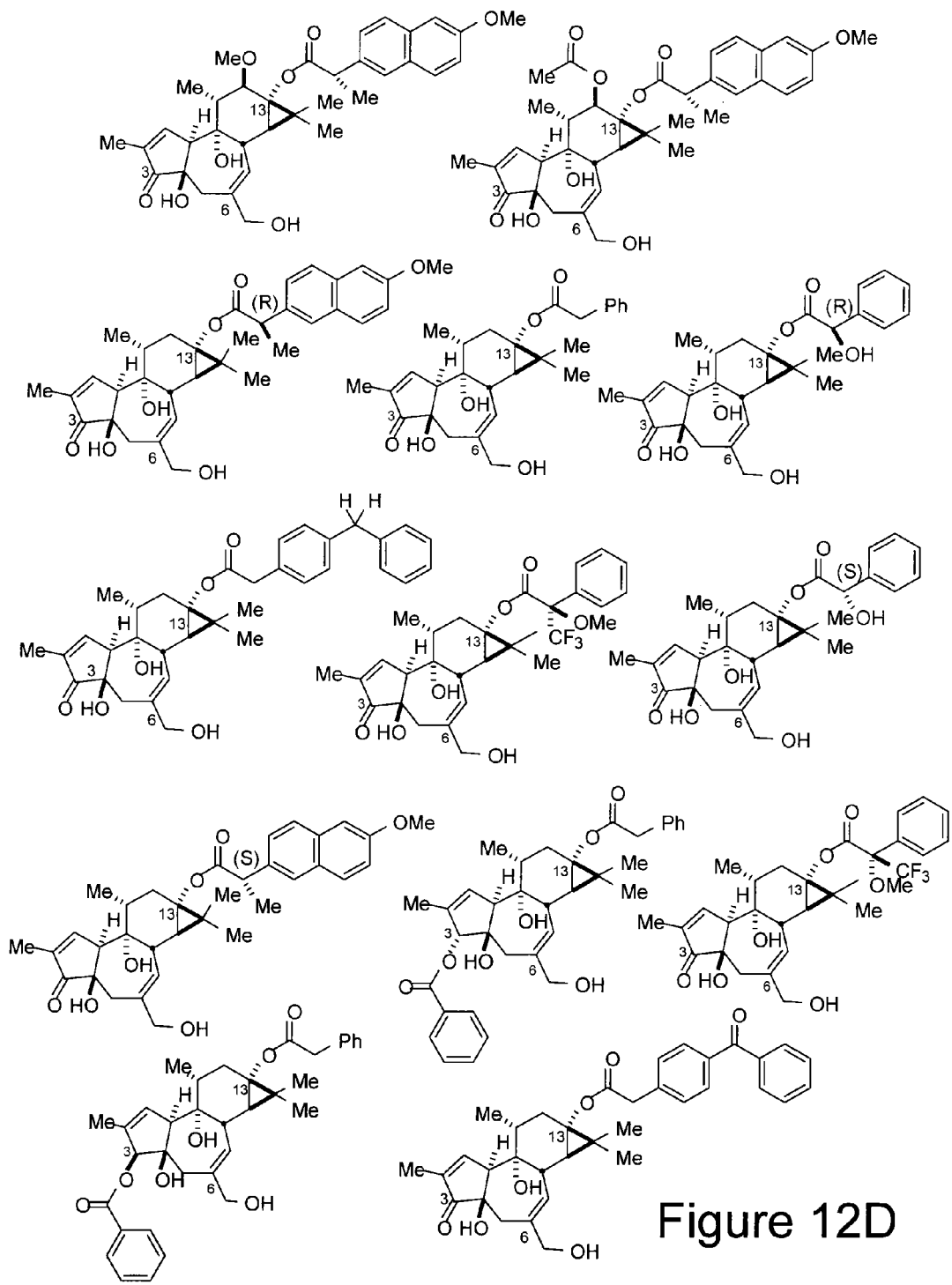
Figure 12E:
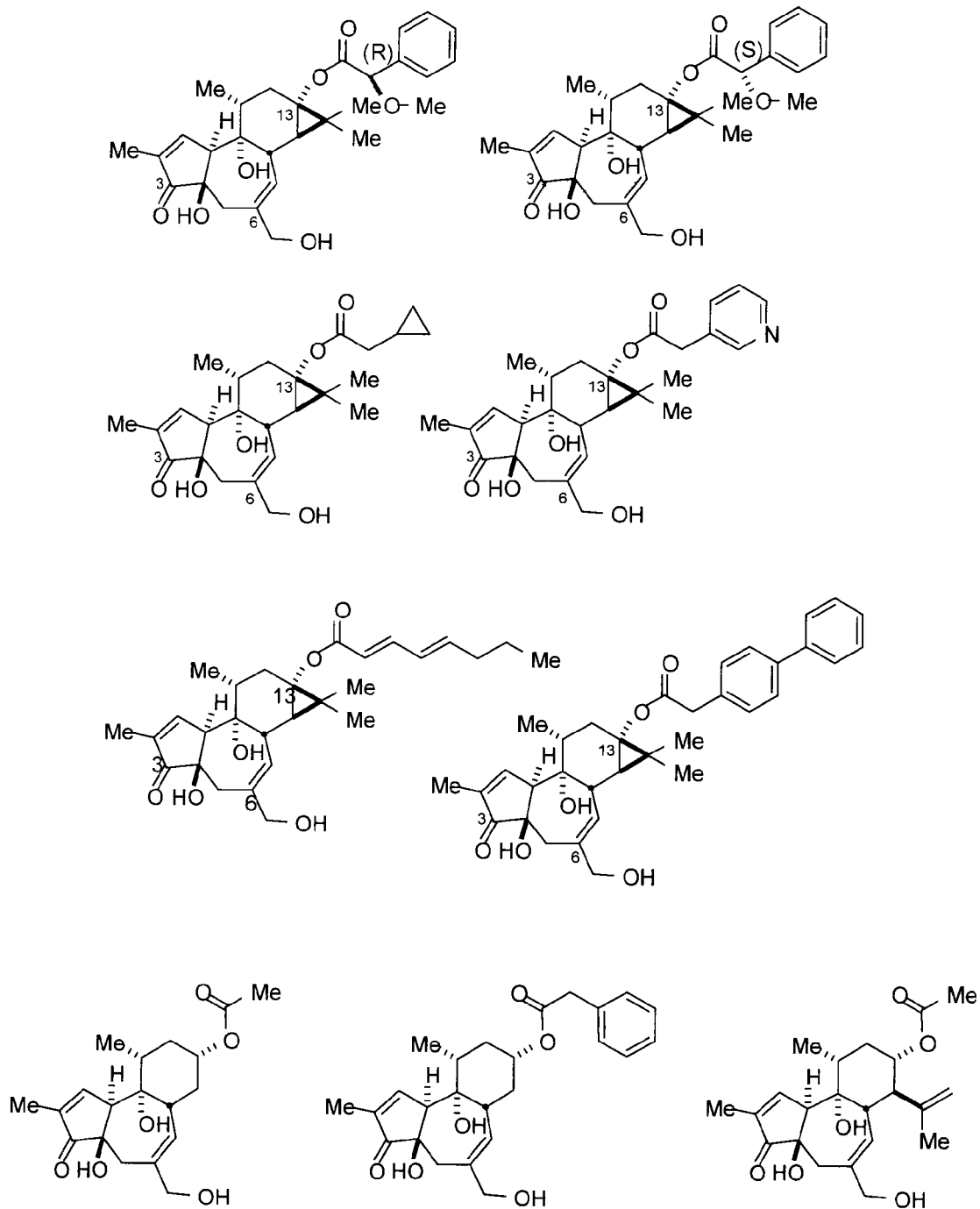

Formulae VI' and VI" can be formed using the synthesis illustrated in FIG. 11. FIG. 11 describes a method of synthesis for C13 and C3 analogs of prostratin. A C20-trityl-C13-ester analogue of prostratin, obtained as taught previously, e.g. FIG. 3, e.g. 13-phenylacetyl-20-trityl prostratin is reduced to the corresponding C3-α-alcohol with e.g., sodium triacetoxyborohydride followed by esterification of the C3-alcohol with e.g. benzoic acid and 1-ethyl-3-[3-(dimethylamino)-propyl] carbodiimide. Deprotection at C20 then provides a 3-α-benzoyl-3-phenylacetyl prostratin analogue. For the C3-β-ester analogues, a C20-trityl-C13-ester analogue of prostratin, obtained as taught previously, e.g., FIG. 3, e.g., 13-phenylacetyl-20-trityl prostratin is reduced to the corresponding C3-β-alcohol with e.g., cerium(III) chloride and sodium borohydride followed by esterification of the C3-alcohol with e.g., benzoic acid and 1-ethyl-3-[3-(dimethylamino)-propyl] carbodiimide. Deprotection at C20 then provides a 3-β-benzoyl-3-phenylacetyl prostratin analogue.

Figure 13:
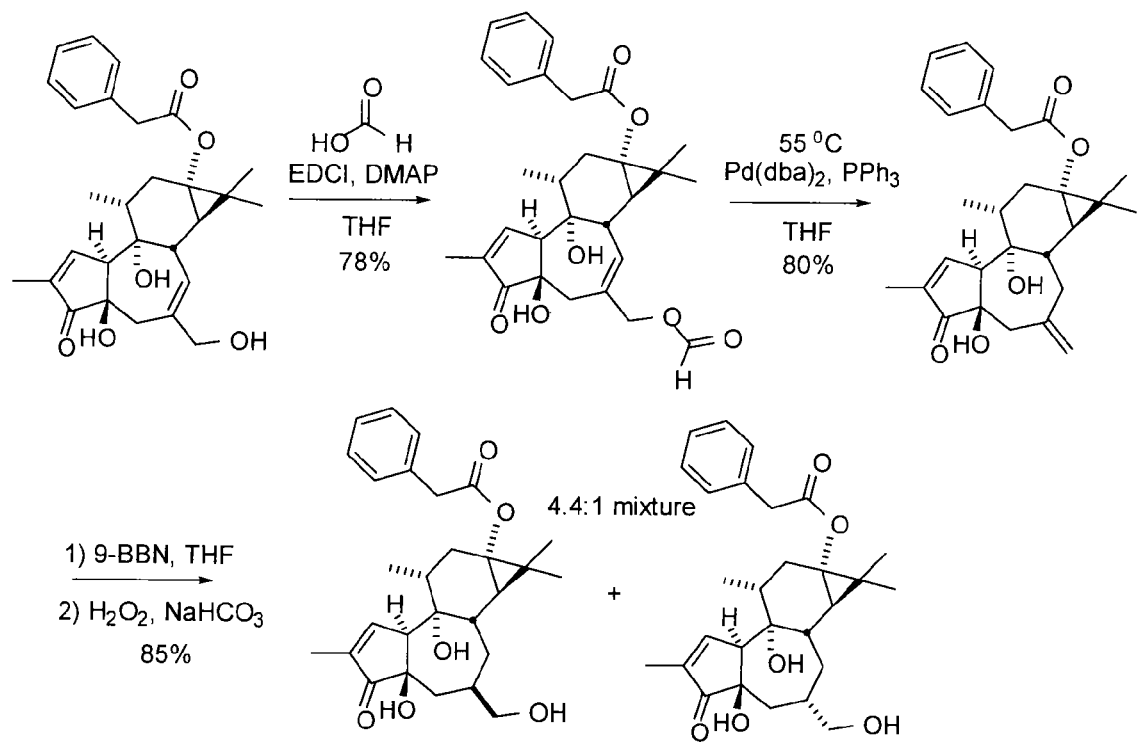
FIG. 13 illustrates an exemplar synthesis for compounds represented by Formula VII' and VII".

Formulae VII' and VII" can be formed using the synthesis illustrated in FIG. 13. FIG. 13 describes a general method of synthesis for prostratin analogues with a saturated C6-C7 bond, e.g., the C6 isomers of 6,7-dihydro-12-deoxy-13-phenylacetyl phorbol. In this method, phorbol is converted to a prostratin analogue, e.g., 12-deoxy-13-phenylacetyl phorbol, as taught in this manuscript. The prostratin analogue is converted into a C20-formate ester through exposure to e.g., formic acid and a coupling agent like 1-ethyl-3-[3-(dimethylamino)-propyl]carbodiimide. Rearrangement in the presence of e.g., $Pd(dba)_2$ is followed by hydroboration and oxidative hydrolysis to give the C6 isomers of 6,7-dihydro-12-deoxy-13-phenylacetyl phorbol.

Pharmaceutical Compositions

Administration of the active compounds and salts described herein can be via any of the accepted modes of administration for therapeutic agents. These methods include oral, parenteral, transdermal, subcutaneous and other systemic modes. In some instances it may be necessary to administer the composition parenterally.

Depending on the intended mode, the compositions may be in the form of solid, semisolid or liquid dosage forms, such as, for example, tablets, suppositories, pills, capsules, powders, liquids, suspensions, skin patch, or the like, preferably in unit dosage forms suitable for single administration of precise dosages. The compositions can include a conventional pharmaceutical excipient and an active compound of the present disclosure or the pharmaceutically acceptable salts thereof (e.g., prostratin, bryostatin, and their analogs) and, in addition, may include other medicinal agents, pharmaceutical agents, carriers, adjuvants, diluents, etc.

Embodiments of the compounds of the present disclosure are typically administered to a patient in the form of a pharmaceutical composition or formulation. Such pharmaceutical compositions can be administered to the patient by any acceptable route of administration including, but not limited to, oral, rectal, vaginal, nasal, inhaled, topical (including transdermal) and parenteral modes of administration.

Accordingly, an embodiment of the present disclosure is directed to a pharmaceutical composition comprising a pharmaceutically-acceptable carrier or excipient and a therapeutically effective amount of a compound of the present disclosure or a pharmaceutically acceptable salt thereof. Optionally, such pharmaceutical compositions may contain other therapeutic and/or formulating agents if desired. When discussing compositions, the "compound of the present disclosure" may also be referred to herein as the "active agent" or "agent". As used herein, the term "compound of the present disclosure" is intended to include a novel compound described in formulae provided herein and in the claims (e.g., prostratin, bryostatin, and their analogs).

The pharmaceutical compositions of the present disclosure typically contain a therapeutically effective amount of a compound of the present disclosure or a pharmaceutically-acceptable salt thereof. Typically, such pharmaceutical compositions can contain about 0.1 to about 95% by weight of the active agent; preferably, about 5 to about 70% by weight; and more preferably about 10 to about 60% by weight of the active agent.

A conventional carrier or excipient can be used in the pharmaceutical compositions of the present disclosure. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this present disclosure are commercially-available. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the present disclosure are preferably packaged in a unit dosage form. The term "unit dosage form" refers to a physically discrete unit suitable for dosing a patient, e.g., each unit containing a predetermined quantity of active agent (e.g., prostratin, bryostatin, and their analogs) calculated to produce the desired therapeutic effect either alone or in combination with one or more additional units. For example, such unit dosage forms can be capsules, tablets, pills, and the like, or unit packages suitable for parenteral administration.

In an embodiment, the pharmaceutical compositions of the present disclosure are suitable for oral administration. Suitable pharmaceutical compositions for oral administration can be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present disclosure as an active ingredient.

When intended for oral administration in a solid dosage form (i.e., as capsules, tablets, pills and the like), the pharmaceutical compositions of the present disclosure can typically include the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and anti-oxidants can also be present in the pharmaceutical compositions of the present disclosure. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like.

Pharmaceutical compositions of the present disclosure may also be formulated to provide slow or controlled release of the active agent using, by way of example, hydroxypropyl methyl cellulose in varying proportions; or other polymer matrices, liposomes and/or microspheres. In addition, the pharmaceutical compositions of the present disclosure may optionally contain opacifying agents and can be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of the present disclosure can also be administered parenterally (e.g., by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations can be rendered sterile by use of a sterile injectable medium, a sterilizing agent, filtration, irradiation, or heat.

Alternatively, the pharmaceutical compositions of the present disclosure are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the present disclosure will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition can be in the form of a capsule or cartridge (made, for example, from gelatin) comprising a compound of the present disclosure and a powder suitable for use in a powder inhaler. Suitable powder bases include, by way of example, lactose or starch.

The compounds of the present disclosure can also be administered transdermally using known transdermal delivery systems and excipients. For example, the active agent can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, can be used in such transdermal compositions if desired.

If desired, the compounds of this present disclosure can be administered in combination with one or more other therapeutic agents. In this embodiment, a compound of this present disclosure is either physically mixed with the other therapeutic agent to form a composition containing both agents; or each agent is present in separate and distinct compositions which are administered to the patient simultaneously or sequentially.

For example, a compound of the present disclosure can be combined with a second therapeutic agent using conventional procedures and equipment to form a composition comprising a compound of the present disclosure (e.g., prostratin, bryostatin, and their analogs) and a second therapeutic agent. Additionally, the therapeutic agents can be combined with a pharmaceutically acceptable carrier to form a pharmaceutical composition comprising a compound of the present disclosure, a second therapeutic agent and a pharmaceutically acceptable carrier. In this embodiment, the components of the composition are typically mixed or blended to create a physical mixture. The physical mixture is then administered in a therapeutically effective amount using any of the routes described herein. Alternatively, the therapeutic agents may remain separate and distinct before administration to the patient. In this embodiment, the agents are not physically mixed together before administration but are administered simultaneously or at separate times as separate compositions. Such compositions can be packaged separately or can be packaged together as a kit. The two therapeutic agents in the kit can be administered by the same route of administration or by different routes of administration. Any therapeutic agent compatible with the compounds of the present disclosure can be used as the second therapeutic agent.

In an embodiment, multiple doses of the agent (e.g., prostratin, bryostatin, and their analogs and/or prodrugs thereof) are contacted (e.g., administered). The frequency of administration of the agent can vary depending on any of a variety of factors, e.g., severity of the symptoms, and the like. For example, in an embodiment, the agent is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in an embodiment, the agent is administered continuously.

The duration of contacted (e.g., administered) of the agent, e.g., the period of time over which the agent is administered, can vary, depending on any of a variety of factors, e.g., patient response, etc. For example, the agent can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art.

In an embodiment of the present disclosure, an effective dosage may be in the range of 0.001-100 mg/kg/day, preferably 0.005-5 mg/kg/day. For an average 70 kg human, this would amount to 0.007-7000 mg per day, or preferably 0.05-350 mg/day. Alternatively, the administration of compounds as described by L. C. Fritz et al. in U.S. Pat. No. 6,200,969 is followed. One of skill in the art with this disclosure can create an effective pharmaceutical formulation.

Methods of Use

Embodiments of the present compounds (e.g., prostratin analogs, bryostatin analogs, and prodrugs of prostratin and prostratin analogs) have been shown to have activity in the following applications: (1) activation of protein kinase C by showing translocation of different isoforms of PKC; (2) growth arrest of proliferating cells; and/or (3) U1 cell line latent virus induction. In particular, embodiments of the compounds can exhibit activity against human immunodeficiency virus (HIV), stimulate transcription of proviral HIV DNA, and/or bind to protein kinase C. Additional details are provided in the Examples.

In general, the compounds of the present disclosure and pharmaceutical compositions thereof can be useful in treating disease caused by HIV, in particular AIDS. The treatment methods typically comprise administering to a subject (e.g., human) infected with such virus a therapeutically effective amount of a compound of the present disclosure in one or more doses, alone or in combination with other agents (e.g., drugs or biologicals). For example, one or more compounds of the present disclosure is provided or administered to a subject infected with HIV in an amount effective to result in the treatment of HIV or AIDS. In an embodiment, one or more compounds of the present disclosure can be used in combination with other HIV/AIDS drugs or biologicals.

The present disclosure also provides methods of prophylactically treating an infection by a HIV virus comprising administering an effective amount of a compound of the present disclosure in one or more doses, alone or in combination with other agents (e.g., drugs or biologicals) to a subject in need thereof.

As mentioned above, compounds of the present disclosure and pharmaceutical compositions can be used in combination of one or more other therapeutic agents for treating viral infection and other diseases. For example, compounds of the present disclosure and pharmaceutical compositions provided herein can be employed in combination with other anti-viral agents to treat viral infection.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

General Methods

Unless otherwise specified, all reactions were carried out in an oven-dried (>110° C.) round-bottom flask equipped with a Teflon™ coated magnetic stir bar and a rubber septum under a positive pressure of argon. Sensitive solvents and reagents were transferred by syringe or stainless steel cannula. Reactions were run at 20° C. unless otherwise stated. The pH was controlled by the reaction conditions and not checked or adjusted unless otherwise.

Unless otherwise specified, reaction temperatures refer to the external temperatures of the bath in which the reaction vessel was partially immersed. The term "0° C." refers to an ice water bath.

The terms "removal of the solvent in vacuo" and "concentration" refer to evaporation of solvent using a Buchi rotary evaporator equipped with a vacuum pump. Residual solvents were removed from nonvolatile samples using a vacuum line held at 0.1-1.0 mm Hg.

Reagents and Solvents

The starting material compounds, solvents, reagents, etc. described herein are available from commercial sources or are easily prepared from literature references by one of skill in the art. See Chem Sources USA, published annually by Directories Publications, Inc. of Boca Raton, Fla. Also see The Aldrich Chemical Company Catalogue, Milwaukee, Wis. The starting materials are used as obtained unless otherwise noted. Dichloromethane and toluene were passed through an alumina drying-column. Pyridine and diisopropylmethane were distilled from calcium hydride under nitrogen. Denatured chloroform was passed through a pad of basic alumina and stored over anhydrous potassium.

Chromatography

Analytical thin-layer chromatography (TLC) was performed by using glass or aluminum-backed silica plates coated with a 0.25 mm thickness of silica gel 60 F254 (Merck), visualized with an ultraviolet light, followed by exposure to p-anisaldehyde solution, potassium permanganate solution, or ceric ammonium molybdate solution and heating.

The term "flash column chromatography" refers to column chromatography using Merck silica gel 60 (230-400 mesh) as described by Still et al., "Rapid chromatographic technique for preparative separations with moderate resolution," J. Org. Chem., 43, 2923-2925 (1978). The eluent composition is indicated following the description of purification (percentage of the more polar solvent in the less polar solvent). The size of the column, the amount of silica gel loaded and the volume of eluent required for packing and elution were chosen based on the method described by Still.

Physical and Spectroscopic Data

Optical rotations were measured on a JASCO DIP-360 digital polarimeter using solutions in indicated solvents. All values are reported in the following format: [ ]D (temperature of measurement)=specific rotation (concentration of the solution reported in units of 10 mg sample per 1 mL solvent, solvent used).

Varian 300 spectrometer 300 MHz for $^1$H and 75 MHz for $^{13}$C, Varian 400 spectrometer 400 MHz for $^1$H and 100 MHz for $^{13}$C or on a Varian 500 spectrometer 500 MHz for $^1$H and 125 MHz for $^{13}$C. $^1$H chemical shifts are reported in parts per million (ppm) using residual CHCl3 ($\delta$ 7.27) as the internal standard, coupling constants are reported in Hertz (Hz). Proton ($^1$H) NMR information is tabulated in the following format: multiplicity, number of protons, coupling constant, and structural assignments (in the format of "carbon-numbering-H" (the natural product numbering system is used)). Multiplicities are reported as follows: s=singlet, d=doublet, t=triplet, q=quartet, sept=septet, dd=doublet of doublets, td=triplet of doublets, ddd=doublet of doublet of doublets, m=multiplet. Proton decoupled $^{13}$C NMR spectra are reported in ppm relative to residual CHCl$_3$ ($\delta$ 7.23) unless noted otherwise.

Infrared spectra were recorded on a Perkin-Elmer Spectrum BX Fourier Transform Spectrometer using neat material on a NaCl plate. All values are reported in wavenumbers (cm$^{-1}$) and are externally referenced to polystyrene film (1601 cm$^{-1}$). High-resolution mass spectra (HRMS) were recorded at the NIH regional mass spectrometry facility at the University of California, San Francisco, or at the Vincent Coates Foundation Mass Spectrometry Laboratory at Stanford University.

Example 1

Synthesis of Prostratin and C13 Prostratin Analogs via a C20-protected C13 OH Intermediate Prostratin and C13 prostratin analogs were prepared as illustrated in FIG. 1.

A. Synthesis of C20-deoxy-C12-trityl phorbol ("C20-trityl Prostratinol")

Isolation of Phorbol from Croton Oil.

To a three-necked round-bottom flask equipped with reflux condenser, mechanical stirrer and a heating pad under an atmosphere of dry nitrogen at 23° C. were added MeOH (450 mL) and Ba(OH)$_2$.H$_2$O (11 g). The mixture was heated at reflux for 2 h and then cooled to room temperature. The reflux condenser was exchanged for plug and croton oil (100 g) was added using a graduated cylinder. After stirring for 14 h, the mixture was filtered through a plug of sand using a flitted funnel. The filtrate was concentrated under reduced pressure. The remainder was diluted with water (300 mL) and extracted with Et$_2$O (2×200 mL) and an additional portion of Et$_2$O (200 mL) which was allowed to separate from the aqueous layer. The acidity of the aqueous phase was adjusted to pH 5 using H$_2$SO$_4$ (1 M) as judged with pH paper. A saturated solution of Na$_2$SO$_4$ (8 mL) was added, and the mixture was stored at 4° C. for 14 h. The mixture was filtered through a layered plug of sand (top) and celite (bottom) using a fritted funnel and the acidity of the filtrate adjusted to pH 7 using NaOH (1 M) as judged with pH paper. The mixture was concentrated under reduced pressure. The brown residue was taken up in EtOH (150 mL). The mixture was filtered through a layered plug of sand and celite, and the filtrate was concentrated under reduced pressure. The residue was diluted with CHCl$_3$ (150 mL) and silica gel was added. The mixture was carefully concentrated under reduced pressure and the brown residue was directly loaded onto a packed silica gel column (6×25 cm). Phorbol was obtained by elution using a solvent gradient of 5% to 15% MeOH/CHCl$_3$. The eluant was collected in 30 mL fractions and the product containing fractions were combined and concentrated under reduced pressure to yield phorbol (1.6 g).

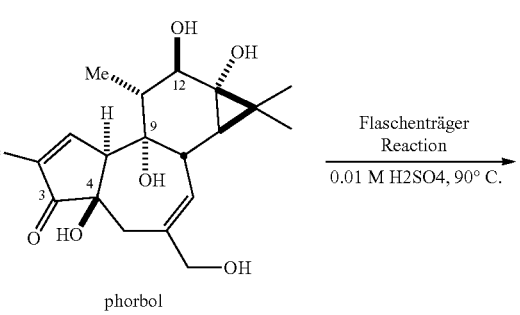

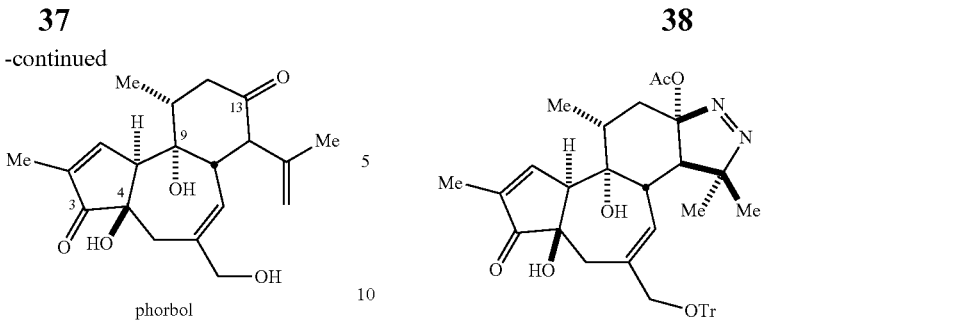

phorbol

Step 1: Preparation of crotophorbolone

To a 50 mL round-bottom flask containing a stirbar and phorbol (1.76 g, 4.82 mmol, 1.0 eq) at ambient temperature (23° C.) was added sulfuric acid (0.01 M aqueous $H_2SO_4$ solution: 16 mL, 0.3 M with respect to phorbol). The flask was equipped with a reflux condenser, the system flushed with a stream of dry nitrogen, and the cloudy, slightly yellow mixture heated to 90° C. After 1 h, the reaction vessel was cooled to room temperature (23° C.), the aqueous solution extracted with EtOAc, and the organic phase washed with brine. The organic phase was dried over $Na_2SO_4$, filtered, concentrated under reduced pressure, and purified by flash chromatography on a 4.5×18 cm silica gel column eluting with a solvent gradient from 75% to 90% EtOAc/petrol ether followed by elution with 100% EtOAc. The eluant was collected in 75 mL portions, and the crotophorbolone containing fractions were combined and concentrated to give crotophorbolone (654 mg).

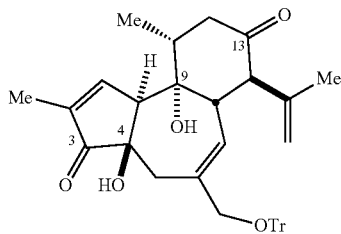

Step 2: Preparation of $C_{20}$-trityl crotophorbolone

To a 100 mL round-bottom flask containing a stirbar and crotophorbolone (480 mg, 1.39 mmol, 1.0 eq) at ambient temperature (23° C.) was added pyridine (14.0 mL, 0.10 M). After dissolution of crotophorbolone, trityl chloride (1.16 g, 4.16 mmol, 3.0 eq) was added. After completion of the reaction, the reaction mixture was diluted with EtOAc, and the resulting mixture washed with water (30 mL), a saturated aqueous $NaHCO_3$ solution and brine. The organic phase was dried over $Na_2SO_4$, filtered and concentrated under reduced pressure; the residue was placed under high vacuum and then purified by flash chromatography on a 3.5×21 cm silica gel column eluting with a solvent gradient from 25% to 40% EtOAc/petrol ether. The eluant was collected in 23 mL portions and the product containing fractions were combined and concentrated. The resulting residue was placed under high vacuum to give $C_{20}$-trityl crotophorbolone (813 mg) as a white solid.

Step 3: Preparation of the $C_{13}$-acetoxy pyrazoline

To a 100 mL round-bottom flask containing a stirbar and $C_{20}$-trityl crotophorbolone (114 mg, 0.194 mmol, 1.0 eq) at ambient temperature (23° C.) was added MeOH (11.4 mL, 0.17 M). After dissolution of the solid, $N_2H_4 \cdot n(H_2O)$ (94 μL, 1.94 mmol, 10.0 eq) and AcOH (55 μl, 0.968 mmol, 5.0 eq) were added. After about 2 hours, EtOAc (19 mL, 100 mL EtOAc/1 mol of starting material) and activated, basic $Al_2O_3$ (2.9 g, 15 g $Al_2O_3$/1 mol of starting material) were added, and the resulting mixture was stirred for 15 min. The mixture was filtered through a plug of sand (0.5 cm), Celite® (2 cm), sand (0.5 cm) layered in a fitted funnel (3×7 cm) and then washed with EtOAc. The filtrate was concentrated under reduced pressure.

The residue was transferred using EtOAc into a thick-walled vial (3×15 cm) and concentrated under reduced pressure; the residue was placed under high-vacuum. The flask was capped with a rubber septum and flushed with argon. Toluene (6.7 mL, 0.029 M) and $iPr_2Net$, (668 μL, 0.29 M) were added to the flask, and using a cannula, a gentle stream of argon was passed through the mixture for 15 min. The rubber septum was carefully exchanged for a threaded Teflon plug and the sealed reaction vessel was placed into an oil bath preheated to 140° C. After 16.5 h, the slightly turbid, yellowish mixture was cooled to room temperature and the threaded Teflon plug quickly exchanged for a rubber septum, and the flask was purged with argon.

$CH_2Cl_2$ (5.0 mL) was added, and the mixture was immediately cooled to −78° C. A clear and colorless to slightly yellow solution of $Pb(OAc)_4$ (172 mg, 0.387 mmol, 2.0 eq) $CH_2Cl_2$ (3.0 mL, 7.8 M concerning $Pb(OAc)_4$) prepared ahead of time was added, and after 15 min, the mixture was warmed to ambient temperature (23° C.). After 20 min, the mixture was diluted with EtOAc and then washed with a saturated aqueous solution of $NaHCO_3$, water and brine. The organic phase was dried over $Na_2SO_4$, filtered and concentrated under reduced pressure. The residue was purified by flash chromatography on a 2×20 cm silica gel column eluting with a solvent gradient from 20% to 40% EtOAc/petrol ether. The eluant was collected in 10 mL portions, and the product containing fractions were combined and concentrated to give the $C_{13}$-acetoxy pyrazoline (55.0 mg, 0.0832 mmol, 43%). Analytical Data for the $C_{13}$-acetoxy pyrazoline: TLC $R_f$=0.47 (50% EtOAc/Pentane), one purple spot in p-anisaldehyde (visible under UV lamp); $[\alpha]_D^{23.5}$=+60.7° (c 1.00, $CH_2Cl_2$); $^1$H NMR (500 MHz, $CDCl_3$): δ 7.52 (t, J=1.8 Hz, 1H), 7.40-7.43 (m, 5H), 7.26-7.31 (m, 5H), 7.22-7.25 (m, 5H), 5.62 (d, J=3.4 Hz, 1H), 3.50 (s, 2H), 3.28 (dd, 1H, J=4.9 Hz, 12.1 Hz), 2.95 (s, 1H), 2.47-2.53 (m, 2H), 2.36 (d, 1H), 2.18 (d, 1H, J=19.3 Hz), 2.14 (d, 1H, J=16.1 Hz), 2.13 (s, 3H), 2.09 (s, 1H), 2.07 (s, 1H), 1.80 (dd, 3H, J=1.4 Hz, 2.8 Hz), 1.68 (s, 3H), 1.52 (dd, 1H, 8.9 Hz, 14.5 Hz), 1.34 (s, 3H), 1.23 (d, 3H, J=7.3 Hz) ppm; $^{13}$C NMR (125 MHz, CDCl$_3$): δ 208.41, 168.80, 157.07, 144.02, 138.42, 136.97, 128.64 (6C), 127.94 (6C), 127.20 (3C), 125.89 (3C), 119.40, 92.94, 87.03, 77.85, 73.76, 68.72, 57.33, 45.10, 40.20, 39.36, 35.93, 31.66, 27.89, 22.57, 22.09, 18.13, 10.46 ppm; FT-IR (thin film): ν 3411, 2972, 2933, 1746, 1705, 1650, 1596, 1448, 1236, 1030, 910, 732 cm$^{-1}$; HRMS: Calcd.: 683.3097 (for C$_{41}$H$_{44}$N$_2$O$_6$Na). found: 683.3093.

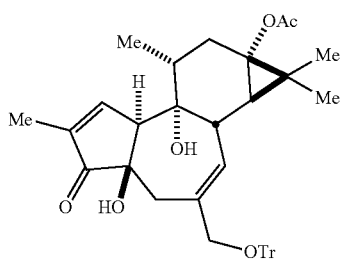

Step 4: Preparation of C$_{20}$-Trityl Prostratin

A gentle stream of argon was introduced into a 20 mL scintillation vial (flint glass) with the C$_{13}$-acetoxy-prostratin pyrazoline (36 mg, 0.055 mmol, 1.0 eq) and EtOAc (9.0 mL, 0.006 M) for 10 min. The flask was sealed with a plastic cap and placed into a Rayonett and exposed to 350 nm radiation for 30 min. The flask was removed from the Rayonett, the contents allowed to cool to room temperature (23° C.), and the solution concentrated under reduced pressure. The residue was purified by flash chromatography on a 2.×20 cm silica gel column eluting with a solvent gradient of 20% (200 mL) and 40% EtOAc/petrol ether (200 mL), and the eluant was collected in 10 mL fractions. The product containing fractions (12 to 20) were combined and concentrated to give C$_{20}$-trityl prostratin (22 mg, 35, mmol, 64%) as a white solid. Analytical Data: R$_f$ 0.82 (50% EtOAc/pentane); [α]$_D^{20}$ +43.9 (c=0.915, CHCl$_3$); 500 MHz $^1$H NMR (CDCl$_3$) δ 7.59 (s, 1H), 7.43-7.26 (m, 6H), 7.30-7.26 (m, 6H), 7.24-7.20 (m, 3H), 5.62 (d, J=4.1 Hz, 1H), 5.24 (bs, 1H), 3.51 (s, 2H), 3.27 (s, 1H), 2.93 (dd, J=5.3, 5.3 Hz, 1H), 2.51 (d, J=19.0 Hz, 1H), 2.39 (d, J=18.9 Hz, 1H), 2.11-2.04 (m, 2H), 2.06 (s, 3H), 1.94 (ddq, J=11.3, 6.9, 6.6 Hz, 1H), 1.77 (dd, J=2.9, 1.2 Hz, 3H), 1.57 (dd, J=14.6, 11.3, 1H), 1.19 (s, 3H), 1.07 (s, 3H), 0.88 (d, J=6.5 Hz, 3H), 0.82 (d, J=5.3 Hz, 1H); 100 MHz $^{13}$C NMR (CDCl$_3$) δ 209.5, 173.4, 161.6, 144.2 (3C), 137.7, 132.8, 130.9, 128.9 (6C), 128.0 (6C), 127.2 (3C), 87.0, 76.0, 74.1, 69.6, 63.9, 55.9, 39.6, 39.4, 36.5, 32.6, 32.1, 23.5, 22.9, 21.5, 18.8, 15.6, 10.4; 100 MHz DEPT (CDCl$_3$) δ CH$_3$: 23.5, 21.5, 18.8, 15.6, 10.4. CH$_2$: 69.6, 39.4, 32.1. CH: 161.6, 130.9, 128.9 (6C), 128.0 (6C), 127.2 (3C), 55.9, 39.6, 36.5, 32.6. C: 209.5, 173.4, 144.2 (3C), 137.7, 132.8, 87.0, 76.0, 74.1, 63.9, 32.6; IR (NaCl, thin film/CHCl$_3$) 3405 (bs), 3059, 2925, 2873, 1723, 1713, 1692, 1630, 1493, 1449, 1380, 1369, 1328, 1258, 1248, 1219, 1178, 1155, 1134, 1080, 1054, 1031, 1018, 982, 946, 899, 884, 754, 705, 667 cm$^{-1}$.

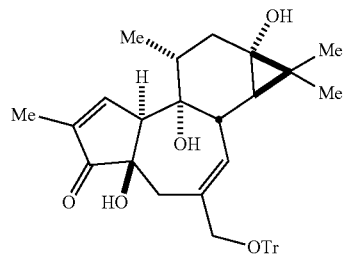

Step 5: Preparation of C$_{12}$-deoxy-C$_{20}$-trityl phorbol

To a 20 mL vial with a stirbar containing C$_{20}$-trityl prostratin (29.0 mg, 0.0458 mmol, 1.0 eq) and MeOH (7.6 mL, 0.006 M) at ambient temperature (23° C.) was added Ba(OH)$_2$·8H$_2$O (145 mg, 0.458 mmol, 10.0 eq). After completed reaction, the mixture was diluted with CH$_2$Cl$_2$, and washed with pH 7 sodium potassium phosphate buffer, water, and brine. The organic phase was then dried over Na$_2$SO$_4$, filtered and concentrated under reduced pressure. The residue was purified by flash chromatography on a 2×20 cm silica gel column eluting with a solvent gradient from 30% to 50% EtOAc/petrol ether. The eluant was collected in 30 mL portions, and the product containing fractions were combined and concentrated to give C$_{12}$-deoxy-C$_{20}$-trityl phorbol (24.0 mg, 0.0406 mmol, 89%). Analytical Data: R$_f$ 0.38 (50% EtOAc/pentane); [α]$_D^{20}$ +40.1 (c=1.120, CHCl$_3$); 500 MHz $^1$H NMR (CDCl$_3$) δ 7.55 (s, 1H), 7.45-7.42 (m, 6H), 7.31-7.28 (m, 6H), 7.26-7.22 (m, 3H), 5.89 (d, J 3.9 , 1H), 3.57 (d, J=11.8 Hz, 1H), 3.54 (d, J=11.8 Hz, 1H), 3.09 (s, 1H), 2.80 (dd, J=5.5 Hz, 1H), 2.50 (d, J=19.0 Hz, 1H), 2.35 (d, J=19.0 Hz, 1H), 2.24 (bs, 1H), 2.15 (bs, 1H), 2.03 (dd, J=14.3, 7.3 Hz, 1H), 1.98 (m, 1H), 1.79 (s, 3H), 1.60 (dd, J=14.1, 9.1 Hz, 1H), 1.26 (s, 3H), 0.99 (s, 3H), 0.95 (d, J=6.6 Hz, 3H), 0.64 (d, J=6.5 Hz, 1H), one C—OH not observed; 125 MHz $^{13}$C NMR (CDCl$_3$) δ 209.4, 160.5, 144.3 (3C), 137.8, 134.1, 130.9, 128.9 (6C), 128.0 (6C), 127.2 (3C), 92.3, 87.1, 74.0, 69.6, 59.4, 56.7, 39.6, 39.3, 36.7, 36.0, 33.5, 24.6, 22.5, 19.3, 16.3, 10.4; 125 MHz DEPT (CDCl$_3$) δ CH$_3$: 22.5, 19.3, 16.4, 10.4. CH$_2$: 69.6, 39.3, 36.0. CH: 160.5, 130.3, 128.9 (6), 128.0 (6), 127.2 (3), 56.7, 39.4, 36.7, 33.5. C: 209.5, 144.3 (3C), 137.8, 134.1 92.3, 87.1, 74.0, 59.4, 24.6; IR (NaCl, thin film/CHCl$_3$) 3400 (bs), 2919, 2868, 1690, 1625, 1597, 1488, 1447, 1374, 1325, 1300, 1217, 1186, 1147, 1054, 1028, 1000, 943, 922, 897, 754, 703 cm$^{-1}$.

B. Synthesis of C13-Analogs of Prostratin

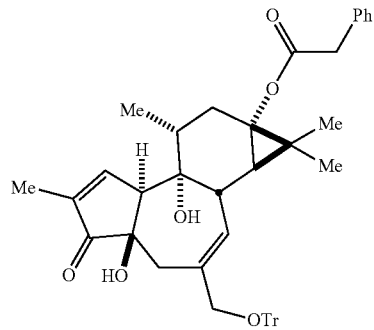

Step 6: Preparation of $C_{12}$-deoxy-$C_{13}$-(phenylacetyl)-$C_{20}$-trityl phorbol ("$C_{20}$-Trityl Prostratinol"

To a 5 mL vial containing $C_{12}$-deoxy-$C_{20}$-trityl phorbol (16 mg, 0.0271 mmol, 1.0 eq) and THF (271 µL, 0.1 M) at ambient temperature (23° C.) were added 1-ethyl-3-(3'-dimethylaminopropyl)-carbodiimide hydro chloride (13.0 mg, 0.0677 mmol, 2.5 eq), phenylacetic acid (4.4 mg, 0.033 mmol, 1.2 eq) and DMAP (1 crystal~1 mg). After completion of the reaction, the mixture was diluted with EtOAc and a saturated aqueous NH$_4$Cl solution. The mixture was stirred for 10 min and diluted with EtOAc, washed with water and brine, and the organic phase was then dried over Na$_2$SO$_4$, filtered and concentrated under reduced pressure. The residue was purified by flash chromatography on a 2×20 cm silica gel column eluting with 25% EtOAc/petrol ether. The eluant was collected in 10 mL portions, and the product containing fractions were combined and concentrated to give $C_{12}$-deoxy-$C_{13}$-(phenylacetyl)-$C_{20}$-trityl phorbol (18.3 mg, 0.0258 mmol, 95%). Analytical Data: $R_f$ 0.90 (50% EtOAc/pentane); $[\alpha]_D^{20}$ +10.0 (c=1.45, CHCl$_3$); 500 MHz $^1$H NMR (CDCl$_3$) δ 7.58 (s, 1H), 7.44-7.42 (m, 6H), 7.35-7.28 (m, 11H), 7.24-7.22 (m, 3H), 5.59 (d, J=4.0 Hz, 1H), 5.21 (bs, 1H), 3.63 (d, J=14.9 Hz, 1H), 3.60 (d, J=14.8 Hz, 1H), 3.51 (s, 2H), 3.27 (s, 1H), 2.92 (dd, J=4.9, 4.9 Hz, 1H), 2.52 (d, J=19.1 Hz), 2.40 (d, J=18.9 Hz), 2.09-2.04 (m, 1H), 1.98-1.93 (m, 1H), 1.77 (m, 3H), 1.64 (bs, 1H), 1.56 (dd, J=14.6, 11.3 Hz, 1H), 1.06 (s, 3H), 1.05 (s, 3H), 0.87 (d, J=6.5 Hz, 3H), 0.75 (d, J=5.3 Hz, 1H); 125 MHz $^{13}$C NMR (CDCl$_3$) δ 209.4, 173.6, 161.6, 144.2 (3), 137.6, 133.5, 132.8, 130.9, 129.6 (2), 128.9 (6), 128.8 (2), 128.0 (6), 127.5, 127.2 (3), 87.0, 76.0, 74.1, 69.6, 64.3, 55.9, 41.9, 39.6, 39.4, 36.5, 32.6, 32.0, 23.3, 23.2, 18.7, 15.6, 10.4; 125 MHz DEPT (CDCl$_3$) δ CH$_3$: 23.3, 18.7, 14.6, 10.4. CH$_2$: 69.6, 41.6, 39.4, 32.0. CH: 161.6, 130.9, 129.6 (2), 128.9 (6), 128.8 (2), 128.0 (6), 127.5, 127.2 (3), 55.9, 39.5, 36.5, 32.6. C: 209.4, 173.6, 144.2 (3), 137.6, 133.5, 132.8, 87.0, 76.0, 74.1, 64.3, 23.2; IR (NaCl, thin film/CHCl$_3$) 3410, 3054, 3028, 2925, 2868, 1961, 1710, 1625, 1597, 1488, 1447, 1377, 1328, 1269, 1245, 1217, 1157, 1132, 1077, 1044, 1031, 1008, 982, 946, 897, 884, 752, 705, 667, 628 cm$^{-1}$.

B. Synthesis of DPP, Prostratin and C13 Prostratin Analogs

1. Synthesis of DPP

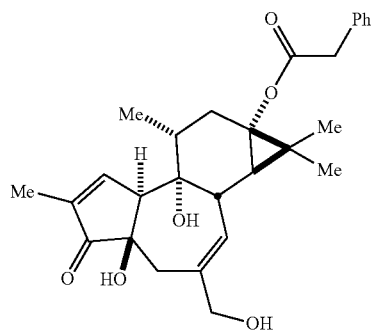

Step 7: Preparation of $C_{12}$-deoxy-$C_{13}$-(phenylacetyl) phorbol ("DPP")

To a 5 mL vial containing $C_{12}$-deoxy-$C_{13}$-(phenylacetyl)-$C_{20}$-trityl phorbol (5.3 mg, 7.5 µmol, 1.0 eq) and MeOH (750 µL, 0.01 M) at ambient temperature (23° C.) was added HClO$_4$ (60% in water; 7.5 µL, 1 mL of HClO$_4$/1 mmol of substrate). After 15 min, the solution was diluted with a saturated aqueous NaHCO$_3$ solution. The mixture was stirred for 5 min and diluted with EtOAc, then washed with water and brine, and the organic phase was dried over Na$_2$SO$_4$, filtered and concentrated under reduced pressure. The residue was purified by flash chromatography on a 0.5×7 cm silica gel column eluting with a solvent gradient from 1% to 5% MeOH/CH$_2$Cl$_2$. The eluant was collected in 3 mL portions, and the product containing fractions were combined and concentrated to give $C_{12}$-deoxy-$C_{13}$-(phenylacetyl) phorbol (3.2 mg, 6.9 µmol, 92%). Analytical Data: $R_f$ 0.49 (50% EtOAc/pentane); $[\alpha]_D^{20}$ +29.9 (c=0.30, CHCl$_3$); 400 MHz $^1$H NMR (CDCl$_3$) δ 7.57 (s, 1H), 7.35-7.26 (m, 5H), 5.64 (d, J=5.5 Hz, 1H), 5.39 (bs, 1H), 4.02 (d, J=12.8 Hz, 1H), 3.96 (d, J=12.8 Hz, 1H), 3.63 (d, J=5.2 Hz, 1H), 3.59 (d, J=4.8 Hz, 1H), 3.25 (s, 1H), 2.98 (dd, J=4.9, 4.9 Hz, 1H), 2.52 (d, J=18.9 Hz, 1H), 2.44 (d, J=18.9 Hz, 1H), 2.99 (bs, 1H), 2.06 (dd, J=14.7, 6.7 Hz, 1H), 2.00-1.91 (m, 1H), 1.76 (d, J=2.5 Hz, 3H), 1.69 (dd, J=14.6, 11.0 Hz, 1H), 1.04 (s, 6H), 0.86 (d, J=6.1 Hz, 3H), 0.76 (d, J=5.6 Hz, 1H), C20-OH not observed; 100 MHz $^{13}$C NMR (CDCl$_3$) δ 209.4, 173.8, 161.5, 140.1, 133.4, 133.1, 130.4, 129.5 (2), 128.9 (2), 127.5, 76.2, 73.9, 68.5, 64.2, 55.9, 41.9, 39.3, 38.8, 36.5, 32.7, 31.9, 23.3, 23.2, 18.8, 15.6, 10.3; IR (NaCl, thin film/CHCl$_3$) 3390, 2976, 2925, 2863, 1702, 1625, 1602, 1493, 1454, 1377, 1330, 1266, 1245, 1219, 1160, 1129, 1093, 1075, 1041, 1008, 946, 917, 881, 752, 698, 664 cm$^{-1}$.

2. Synthesis of Prostratin and C13 Prostratin Analogs from $C_{12}$-deoxy-$C_{20}$-trityl phorbol Preparation of Prostratin To a 5 mL vial with $C_{12}$-deoxy-$C_{13}$-acetyl-$C_{20}$-trityl phorbol (19 mg, 30 mmol, 1.0 eq) and MeOH (3 mL, 0.01 M) at 23° C. was added HClO$_4$ (60% in H$_2$O; 30 mL, 1 mL per 1 mmol substrate). After 20 min, the solution was diluted with EtOAc (40 mL). The organic phase was washed with a saturated aqueous NaHCO$_3$ solution (2×10 mL), water (10 mL) and brine (5 mL). The organic phase was dried over Na$_2$SO$_4$, filtered, concentrated under reduced pressure, and purified by flash chromatography on a 2×20 cm silica gel column eluting with a solvent mixture of 6% MeOH/CH$_2$Cl$_2$ (200 mL), and the eluant was collected in 10 mL fractions. The product containing fraction (6-10) were collected and concentrated to give prostratin (1.9 mg, 5.9 mmol, 93%) as a white solid. Analytical Data: $[\alpha]_D^{20}$ +40.6° (c=1.000 g/100 mL, CHCl$_3$); $R_f$ 0.52 (5% MeOH/CH$_2$Cl$_2$); 400 MHz $^1$H NMR (CDCl$_3$) δ

7.58 (s, 1H), 5.58 (d, J=4.3 Hz, 1H), 5.42 (bs, 1H), 4.05 (d, J=12.8 Hz, 1H), 3.98 (d, J=12.8 Hz, 1H), 3.26 (s, 1H), 3.01 (dd, J=5.2, 5.2 Hz, 1H), 2.55 (d, J=19.5 Hz, 1H), 2.50 (s), 2.46 (d, J=19.5 Hz, 1H), 2.08 (dd, J=14.6, 6.7 Hz, 1H), 2.07 (s, 3H), 1.98 (ddq, J=11.0, 6.9, 6.7 Hz, 1H), 1.77 (dd, J=3.1 1.2 Hz, 3H), 1.74 (bs, 1H), 1.57 (dd, J=14.3, 11.3 Hz, 1H), 1.19 (s, 3H), 1.07 (s, 3H), 0.88 (d, J=6.4 Hz, 3H), 0.85 (d, J=5.3 Hz, 1H), one C—OH not observed; 100 MHz $^{13}$C NMR (CDCl$_3$) δ 209.5, 173.5, 161.5, 140.1, 133.0, 130.4, 76.2, 74.0, 68.5, 63.8, 55.9, 39.3, 38.8, 36.5, 32.6, 32.0, 23.4, 22.9, 21.5, 18.8, 15.5, 10.3; 100 MHz DEPT (CDCl$_3$) δ CH$_3$: 23.4, 21.5, 18.8, 15.5, 10.3. CH$_2$: 68.5, 38.8, 32.0. CH: 161.5, 130.4, 55.9, 39.3, 36.5, 32.6. C: 209.5, 173.5, 140.1, 133.0, 76.2, 74.0, 63.8, 22.9; IR (NaCl, thin film/CHCl$_3$) 3385 (br), 2981, 2950, 2919, 2873, 1750, 1622, 1454, 1421, 1374, 1328, 1263, 1248, 1178, 1132, 1077, 1049, 1010, 948, 915, 884, 804, 747, 667 cm$^{-1}$.

Hz, 1H), 2.39 (d, J=18.9 Hz, 1H), 2.10-2.05 (m, 1H), 2.10-2.05 (m, 1H), 2.01-1.93 (m, 1H), 1.78 (s, 3H), 1.58 (dd, J=14.6, 10.9 Hz, 1H), 1.10 (s, 3H), 1.07 (s, 3H), 0.87 (d, J=6.7 Hz, 3H), 0.78 (d, J=4.8 Hz, 1H); 100 MHz $^{13}$C NMR (CDCl$_3$) δ 209.4, 173.6, 161.6, 144.2 (3), 140.9, 140.4, 137.7, 132.8, 132.5, 130.8, 130.0 (3), 129.0 (2), 128.9 (6), 128.0 (6), 127.5 (3), 127.3 (2), 127.2 (2), 87.0, 76.0, 74.0, 69.6, 64.4, 55.9, 41.5, 39.6, 39.4, 36.6, 32.6, 32.0, 23.4, 23.2, 18.8, 15.6, 10.4; 100 MHz DEPT (CDCl$_3$) δ CH$_3$: 161.6, 130.8, 130.0 (3), 129.0 (2), 128.9 (6), 128.0 (6), 127.5 (3), 127.3 (2), 127.2 (2), 55.9, 39.5, 36.5, 32.6. CH$_2$: 69.6, 41.5, 39.4, 32.0. CH: 23.4, 18.7, 15.6, 10.4. C: 209.4, 173.6, 144.2 (3) 140.9, 140.4, 137.7, 132.8, 132.587.0, 76.0, 74.0, 64.4, 23.2; IR (NaCl, thin film/CHCl$_3$) 3416 (bs), 3054, 3023, 2950, 2919, 1868, 1956, 1907, 1708, 1622, 1594, 1519, 1483, 1449, 1413, 1374, 1328, 1274, 1243, 1219, 1152, 1134, 1080, 1046, 1005, 979, 943, 891, 863, 824, 754, 695, 661, 630 cm$^{-1}$.

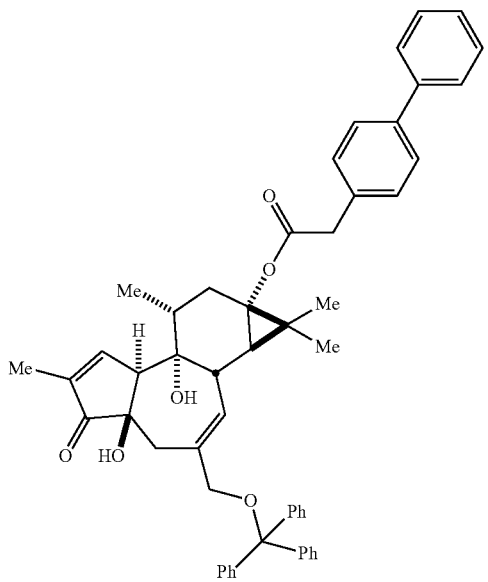

Preparation of $C_{12}$-Deoxy-$C_{13}$-p-Biphenylacetyl-$C_{20}$-Triphenylmethoxy Phorbol To a 5 mL vial with $C_{12}$-deoxy-$C_{20}$-trityl phorbol (4.9 mg, 8.3 mmol, 1.0 eq) and THF (83 μL) at 23° C. were added 1-ethyl-3-(3'-dimethylaminopropyl)-carbodiimide hydro chloride (4.0 mg, 0.0207 mmol, 2.5 eq), biphenylacetic acid (2 mg, 0.001 mmol, 1.2 eq) and DMAP (1 crystal~1 mg). After completion of the reaction, the mixture was diluted with EtOAc and a saturated aqueous NH$_4$Cl solution. The mixture was stirred for 10 min and diluted with EtOAc, washed with water and brine, and the organic phase was then dried over Na$_2$SO$_4$, filtered and concentrated under reduced pressure. The residue was purified by flash chromatography on a 2×20 cm silica gel column eluting with 25% EtOAc/petrol ether. The eluant was collected in 10 mL portions, and the product containing fractions were combined and concentrated to give $C_{12}$-deoxy-$C_{13}$-p-biphenylacetyl-$C_{20}$-triphenylmethoxy phorbol (5.8 mg, 0.074 mmol, 89%). Analytical Data: R$_f$ 0.87 (50% EtOAc/pentane); [α]$_D$° +21.5 (c=0.800, CHCl$_3$); 400 MHz $^1$H NMR (CDCl$_3$) δ 7.61-7.56 (m, 5H, C$_1$—H), 7.47-7.42 (m, 8H), 7.38-7.35 (m, 3H), 7.31-7.27 (m, 6H), 7.24-7.20 (m, 3H), 5.60 (d, J=4.3 Hz, 1H), 5.21 (bs, 1H), 3.66 (s, 2H), 3.51 (s, 2H), 3.27 (s, 1H), 2.93 (m, 1H), 2.52 (d, J=18.7

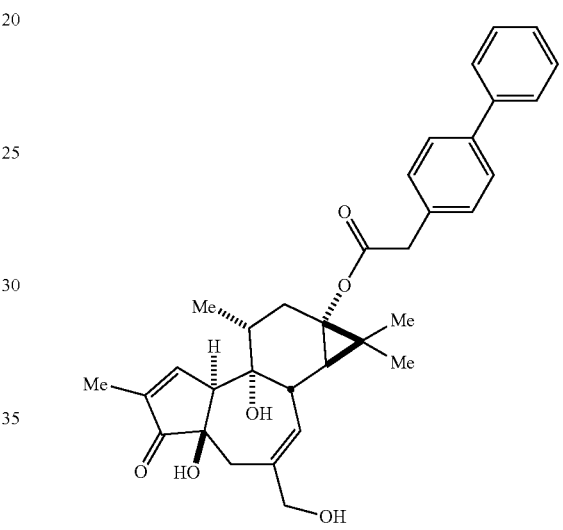

Preparation of $C_{12}$-Deoxy-$C_{13}$-p-Biphenylacetyl Phorbol

To a 5 mL vial with $C_{12}$-deoxy-$C_{13}$-p-biphenylacetyl-$C_{20}$-trityl phorbol (4.8 mg, 6.1 mmol, 1.0 eq) and MeOH (612 mL, 0.01 M) at 23° C. was added HClO$_4$ (60% in H$_2$O; 6 mL, 1 mL per 1 mmol substrate). After 20 min, the solution was diluted with EtOAc (20 mL) The organic phase was washed with a saturated aqueous NaHCO$_3$ solution (2×5 mL), water (5 mL) and brine (2 mL) The organic phase was dried over Na$_2$SO$_4$, filtered, concentrated under reduced pressure, and purified by flash chromatography on a 0.5×6 cm silica gel column eluting with a solvent gradient of 1% (15 mL) and 5% MeOH/CH$_2$Cl$_2$ (10 mL), and the eluant was collected in 3 mL fractions. The product containing fractions (3 to 6) were combined and concentrated to give $C_{12}$-deoxy-$C_{13}$-p-biphenylacetyl phorbol (3.2 mg, 5.9 mmol, 96%) as a clear colorless film. Analytical Data: R$_f$ 0.89 (10% MeOH/CH$_2$Cl$_2$); [α]$_D^{20}$ +26.5 (c=0.320, CHCl$_3$); 400 MHz $^1$H NMR (CDCl$_3$) δ 7.60-7.55 (m, 5H), 7.47-7.43 (m, 2H), 7.37-7.34 (m, 3H), 5.65 (d, J=4.9 Hz, 1H), 5.39 (s, 1H), 4.03 (d, J=12.8 Hz, 1H), 3.97 (d, J=12.7 Hz, 1H), 3.66 (s, 2H), 3.26 (s, 1H), 3.00 (s, 1H), 2.52 (d, J=18.9 Hz, 1H), 2.45 (d, J=18.9 Hz, 1H), 2.32 (s, 1H), 2.08 (dd, J=14.6, 6.7 Hz, 1H), 1.97 (dqd, J=12.8, 6.7, 6.1 Hz, 1H), 1.77 (m, 3H), 1.58 (dd, J=14.6, 11.6 Hz, 1H), 1.08 (s, 3H), 1.05 (s, 3H), 0.88 (d, J=6.1 Hz, 3H), 0.80 (d, J=4.8 Hz, 1H), one C—OH not observed; 100 MHz $^{13}$C NMR (CDCl$_3$) δ 209.4, 173.8, 161.5, 140.8, 140.5, 140.1, 133.1, 132.4, 130.4, 130.0 (2C), 129.0 (2C), 127.6 (3C), 127.3 (2C), 76.2, 73.9, 68.5, 64.3, 56.0, 41.5, 39.3, 38.8, 36.5, 32.7, 32.0, 23.4, 23.2, 18.8, 15.6, 10.3; 100 MHz DEPT (CDCl$_3$) δ CH$_3$: 23.3, 18.8, 15.6, 10.3. CH$_2$: 68.5, 41.5, 38.8, 31.9. CH: 161.5, 130.4, 130.0 (2C), 129.0 (2C), 127.6 (3C), 127.3 (2C), 55.9, 39.3, 36.5, 32.7. C: 209.4, 173.8, 140.8, 140.5, 140.1, 133.1, 132.4, 76.2, 73.9, 64.3, 23.2; IR (NaCl, thin film/CHCl$_3$) 3385 (bs), 2992, 2930, 2868, 1708, 1625, 1488, 1460, 1449, 1405, 1374, 1328, 1271, 1245, 1163, 1132, 1075, 1041, 1010, 940, 886, 757, 705 cm$^{-1}$.

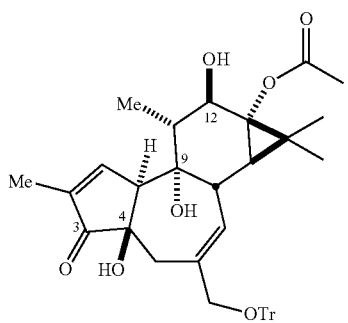

Preparation of C$_{13}$-Acetyl-C$_{20}$-Trityl Phorbol

To a 5 mL vial with C$_{20}$-trityl phorbol (52 mg, 86 mmol, 1.0 eq) and THF (857 mL, 0.1 M) at 23° C. was added DMAP (1 mg, 8.6 mmol, 0.1 eq), EDCI (41 mg, 0.21 mmol, 2.5 eq) and acetic acid (4.9 mL, 86 mmol, 1.0 eq). After 3 h, additional EDCI (20 mg, 0.10 mmol, 1.2 eq) and acetic acid (1 mL, 17 mmol, 0.2 eq) were added. After 1.5 h, the mixture was diluted with EtOAc (1 mL) and a saturated aqueous NH$_4$Cl solution (500 mL). After 5 min, the organic phase was diluted with EtOAc (50 mL), washed with a saturated aqueous NaHCO$_3$ solution (2×10 mL), water (10 mL) and brine (5 mL). The organic phase was dried over Na$_2$SO$_4$, filtered, concentrated under reduced pressure, and purified by flash chromatography on a 2×20 cm silica gel column eluting with a solvent gradient of 25% (100 mL), 35% (100 mL), 40% (100 mL) and 50% EtOAc/petrol ether (100 mL) and the eluant was collected in 30 mL fractions. The product containing fractions (8-10) were collected and concentrated to give C$_{13}$-acetyl-C$_{20}$-trityl phorbol (42 mg, 65 mmol, 76%) as a white foam. Analytical Data: R$_f$ 0.34 (5% MeOH/CH$_2$Cl$_2$); [α]$_D^{20}$ +58.7 (c=0.300, CHCl$_3$); 500 MHz $^1$H NMR (CDCl$_3$) δ 7.56 (s, 1H), 7.44-7.42 (m, 6H), 7.31-7.28 (m, 6H), 7.25-7.22 (m, 3H), 5.61 (d, J=4.3 Hz, 1H), 4.01 (dd, J=9.8, 3.2 Hz, 1H), 3.57 (d, J=13.4 Hz, 1H), 3.54 (d, J=13.8 Hz, 1H), 3.12 (dd, J=5.3, 5.3 Hz, 1H), 3.06 (s, 1H), 2.59 (s, 1H), 2.49 (d, J=19.8 Hz, 1H), 2.37 (d, J=19.8 Hz, 1H), 2.13 (s, 3H), 2.00 (dq, J=9.9, 6.5 Hz, 1H), 1.78 (dd, J=2.6, 1.1 Hz, 3H), 1.65 (s, 1H), 1.26 (s, 3H), 1.23 (s, 3H), 1.05 (d, J=6.5 Hz, 3H), 1.02 (d, J=5.5 Hz, 1H), one C—OH not observed; 125 MHz $^{13}$C NMR (CDCl$_3$) δ 209.0, 174.4, 160.5, 144.2 (3), 139.0, 133.1, 129.1, 128.9 (6C), 128.0 (6C), 127.2 (3C), 87.2, 78.4, 77.6, 73.7, 69.1, 68.5, 57.0, 45.1, 39.4, 39.2, 35.5, 26.9, 23.9, 21.3, 17.1, 15.3, 10.4; 125 MHz DEPT (CDCl$_3$) δ CH$_3$: 23.9, 21.3, 17.1, 15.3, 10.4. CH$_2$: 69.1, 39.2. CH: 160.5, 129.1, 128.9 (6C), 128.0 (6C), 127.2 (3C), 77.6, 57.0, 45.1, 39.4, 35.5. C: 209.0, 174.4, 144.2 (3C), 139.0, 133.1, 87.2, 78.4, 73.7, 68.5, 26.9; IR (NaCl, thin film/CHCl$_3$) 3421 (bs), 3054, 2976, 2925, 2873, 1956, 1715, 1700, 1628, 1594, 1491, 1442, 1372, 1320, 1258, 1181, 1132, 1080, 1052, 1031, 1000, 984, 946, 922, 899, 863 cm$^{-1}$.

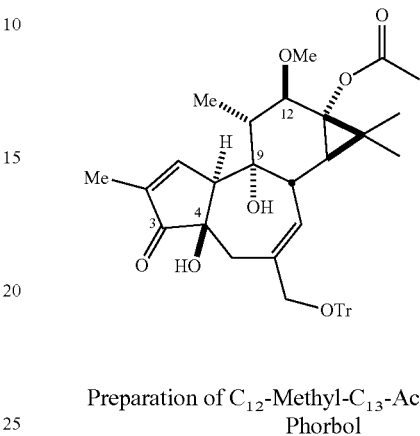

Preparation of C$_{12}$-Methyl-C$_{13}$-Acetyl-C$_{20}$-Trityl Phorbol

To a 5 mL vial with C$_{13}$-acetyl-C$_{20}$-trityl phorbol (12.4 mg, 0.191 mmol, 1.0 eq), 2,6-di-tert-butyl-4-methyl pyridine (15.7 mg, 0.0765 mmol, 4.0 eq) and CH$_2$Cl$_2$ (191 μL, 0.1 M) at 23° C. was added methyl trifluoromethane sulfonate (4.3 μL, 6.3 mg, 0.0383 mmol, 2.0 eq). After 24 h additional trifluoromethane sulfonate (10.0 μL, 14.5 mg, 0.088 mmol, 4.6 eq) and 2,6-di-tert-butyl-4-methylpyridine (20 mg, 0.0974 mmol, 8.9 eq) were added. After 24 h additional trifluoromethane sulfonate (20.0 μL, 29 mg, 0.176 mmol, 9.2 eq) and 2,6-di-tert-butyl-4-methylpyridine (40 mg, 0.1948 mmol, 17.8 eq) were added. After 48 h diethylamine (100 μL) was added. After 2 h the mixture was diluted with EtOAc (50 mL), washed with a saturated aqueous NaHCO$_3$ solution (2×10 mL), water (10 mL) and brine (5 mL). The product was purified on a preparative TLC (20 cm×20 cm×250 μm) using a solvent mixture of 25% EtOAc and pentanes providing the product as a colorless film (8.9 mg, 0.0134 mmol, 70%). Analytical Data: R$_f$ 0.83 (50% EtOAc/pentane); [α]$_D^{20}$ +50.0 (c=1.00, CHCl$_3$); 500 MHz $^1$H NMR (CDCl$_3$) δ 7.59 (s, 1H), 7.44-7.42 (m, 6H), 7.31-7.28 (m, 6H), 7.24-7.22 (m, 3H), 5.65 (d, J=4.5 Hz, 1H), 5.49 (s, 1H), 3.51 (m, 3H), 3.42 (s, 3H), 3.21 (m, 1H), 3.10 (m, 1H), 2.49 (d, J=18.8 Hz, 1H), 2.39 (d, J=16.1 Hz, 1H), 2.12 (s, 3H), 1.98 (m, 1H), 1.77 (d, J=1.6 Hz, 3H), 1.29 (s, 3H), 1.18 (s, 3H), 1.03 (d, J=6.4 Hz, 3H), 1.00 (d, J=5.3 Hz, 1H), C4-OH not observed; 125 MHz $^{13}$C NMR (CDCl$_3$) δ 209.2, 173.5, 161.2, 144.2 (3), 138.2, 132.7, 129.9, 128.9 (6), 128.0 (6), 127.2 (3), 87.1, 85.8, 77.8, 73.9, 69.3, 66.3, 58.0, 56.3, 44.6, 39.5, 39.3, 36.1, 25.8, 24.1, 21.6, 16.8, 15.6, 10.4; 100 MHz DEPT (CDCl$_3$) δ CH$_3$: 58.0, 24.1, 21.6, 16.8, 15.6, 10.4. CH$_2$: 69.3, 39.3, 10.4. CH: 161.2, 129.9, 128.9 (6), 128.0 (6), 127.2 (3), 85.8, 56.3, 44.5, 39.5, 36.1. C: 209.2, 173.5, 144.2 (3), 138.2, 132.7 87.1, 77.8, 73.9, 66.3, 25.8; IR (NaCl, thin film/CHCl$_3$) 3405 (bs), 3054, 2976, 2919, 2873, 1721, 1708, 1628, 1594, 1483, 1447, 1374, 1328, 1258, 1235, 1219, 1186, 1150, 1132, 1085, 1049, 1031, 1000, 956, 933, 894, 860, 757, 703, 664 cm$^{-1}$.

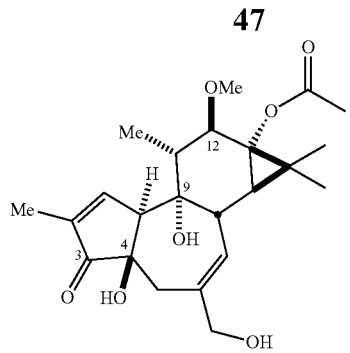

Preparation of $C_{12}$-Methyl-$C_{13}$-Acetyl Phorbol

To a 5 mL vial with $C_{12}$-methoxy-$C_{13}$-acetyl-$C_{20}$-trityl phorbol (6.0 mg, 9.05 mmol, 1.0 eq) and MeOH (905 mL, 0.01 M) at 23° C. was added $HClO_4$ (60% in $H_2O$; 9 μL, 1 mL per 1 mmol substrate). After 20 min, the solution was diluted with EtOAc (20 mL). The organic phase was washed with a saturated aqueous $NaHCO_3$ solution (2×5 mL), water (5 mL) and brine (2 mL). The organic phase was dried over $Na_2SO_4$, filtered, concentrated under reduced pressure, and purified by flash chromatography on a 0.5×6 cm silica gel column eluting with a solvent gradient of 2% (40 mL) and the eluant was collected in 4 mL fractions. The product containing fractions were combined and concentrated to give $C_{12}$-methoxy-$C_{13}$-acetyl phorbol (3.2 mg, 5.9 mmol, 96%) as a clear colorless film. Analytical Data: $R_f$ 0.26 (5% $MeOH/CH_2Cl_2$); $[\alpha]_D^{20}$ +76.5 (c=0.57, $CHCl_3$); 500 MHz $^1H$ NMR ($CDCl_3$) δ 7.58 (s, 1H), 5.66 (d, J=4.8 Hz, 1H), 5.57 (s, 1H), 4.03 (d, J=12.4 Hz, 1H), 3.98 (d, J=12.9 Hz, 1H), 3.50 (d, J=9.5 Hz, 1H), 3.42 (s, 3H), 3.18-3.15 (m, 2H), 2.74 (s, 1H), 2.51 (d, J=18.9 Hz, 1H), 2.45 (d, J=19.0 Hz, 1H), 2.11 (s, 3H), 2.02-1.96 (m, 1H), 1.77-1.76 (m, 3H), 1.27 (s, 3H), 1.16 (s, 3H), 1.03-0.99 (m, 4H), C20-OH not observed; 125 MHz $^{13}C$ NMR ($CDCl_3$) δ 209.2, 173.1, 161.0, 140.6, 133.0, 129.5, 85.8, 78.0, 73.7, 68.3, 66.2, 58.0, 56.3, 44.5, 39.3, 38.8, 36.1, 25.9, 24.0, 21.6, 16.8, 15.6, 10.3; 125 MHz DEPT ($CDCl_3$) δ $CH_3$: 58.0, 24.0, 21.6, 16.8, 15.6, 10.3. $CH_2$: 68.3, 38.8. CH: 161.0, 129.4, 85.8, 56.3, 44.5, 39.3, 36.1. C: 209.2, 173.6, 140.6, 133.0, 78.0, 73.7, 66.2, 25.9; IR (NaCl, thin film/$CHCl_3$) 3381, 2980, 2921, 2881, 1720, 1704, 1631, 1457, 1372, 1326, 1257, 1237, 1135, 1089, 1050, 1007, 958, 928, 912, 889, 856 $cm^{-1}$ Example 2

Synthesis of a 12-deoxy phorbol ester prodrug

Referring now to FIG. 7A, compounds 136-140 were prepared as follows:

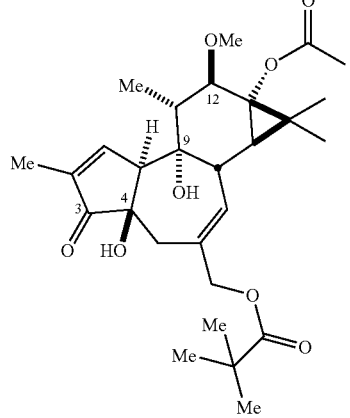

To a solution of prostratin (5.0 mg, 0.013 mmol) in dichloromethane was added pivalic acid (3 μL, 0.026 mmol), DMAP (1 mg), and 1-ethyl-3-(3-dimethylaminopropyl) carbodiimide hydrochloride (5.5 mg, 0.026 mmol). The reaction mixture was stirred for 24 hours at room temperature, at which point additional pivalic acid (3 μL, 0.026 mmol), DMAP (catalytic), and 1-ethyl-3-(3-dimethylaminopropyl) carbodiimide hydrochloride (5.5 mg, 0.026 mmol) was added. The reaction mixture was stirred a further 24 hours, then diluted with ethyl acetate and washed one time with a saturated aqueous solution of ammonium chloride, one time with a saturated solution of sodium bicarbonate, and one time with a saturated solution of brine. The organic layer was dried over anhydrous sodium sulfate, filtered and the solvent was removed in vacuo. The product was purified by normal phase flash chromatography, followed by reverse phase HPLC, to give 2.5 mg product (40% yield). TLC $R_f$=0.29 (30% ethylacetate in petroleum ether), blue spot by p-anisaldehyde stain, visible by UV lamp. Analytical data: $[\alpha]_D^{23.6}$=+49.6° (c 0.25, $CDCl_3$); $^1H$ NMR (500 MHz, $CDCl_3$): δ=7.60 (s, 1H), 5.70 (d, 1H, J=3.8 Hz), 5.38 (brs, 1H), 4.47 (d, 1H, J=13.6), 4.44 (d, 11-1, J=13.3), 3.28 (s, 1H), 2.95 (t, 1H, J=5.5 Hz), 2.49 (d, 1H, J=19.1 Hz), 2.40 (d, 1H, J=18.8 Hz), 2.07 (s, 3H), 2.03 (s, 1H), 2.09-2.04 (m, 4H), 2.00-1.93 (m, 1H), 1.78 (dd, 3H, J=2.9, J=1.34), 1.60-1.55 (m, 1H), 1.19 (s, 3H), 1.17 (s, 9H), 1.07 (s, 3H), 0.88 (d, 3H, J=6.5 Hz), 0.82 (d, 1H, J=5.3 Hz) ppm; $^{13}C$ NMR (125 MHz, $CDCl_3$): δ=208.9, 178.2, 173.2, 161.2, 135.3, 133.3, 132.7, 77.2, 75.7, 73.7, 69.4, 63.5, 55.7, 39.5, 38.8, 38.7, 36.3, 32.2, 31.7, 27.2, 23.2, 22.7, 21.3, 15.3, 10.1 ppm; FT-IR (thin film): v=3411, 2959, 2918, 2968, 2361, 2253, 1722, 1625, 1475, 1457, 1377, 1328, 1261, 1152, 732 cm 1.

C20-carbonate 5 linker-prostratin 138

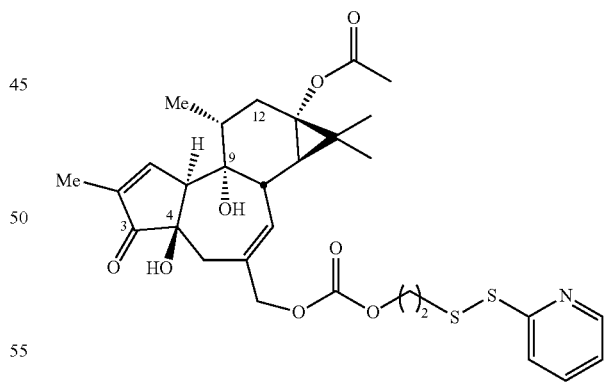

To a solution of 2-(pyridin-2-yldisulfanyl)ethanol (4.2 mg, 0.022 mmol) in THF (0.25 mL) was added phosgene (35.6 mL of a 20% solution in PhMe). The solution was stirred for 5 minutes and the solvent was removed under $N_2$. The residue was dissolved in DCM (220 mL) and added dropwise to a solution of prostratin 1 (8 mg, 0.02 mmol) and pyridine (3.3 mL, 0.04 mmol) at 0° C. The reaction mixture was stirred for 24 hours and then quenched by the addition of aqueous $NH_4Cl$ (0.5 mL). The aqueous phase was separated and extracted with DCM (3×5 mL). The combined organic extracts were dried over $Na_2SO_4$ and concentrated in vacuo. The crude reaction mixture was purified by flash column chromatography (10% EtOAc/hexane increasing to 50% EtOAc/hexane) to give the product as a colorless oil (3.5 mg, 28%). Analytical data: $[\alpha]_D^{25}$ +44.1 (c 0.33, $CHCl_3$); $^1H$ NMR (500 MHz, $CDCl_3$) $\delta_H$ 8.50 (1H, app dq, J=5.0, 1.0 Hz), 7.72 (1H, dt, J=6.5, 1.0 Hz), 7.68 (1H, ddd, J=9.0, 7.0, 2.0 Hz), 7.63-7.60 (1H, m), 7.13 (1H, ddd, J=7.2, 4.8, 1.2 Hz), 5.81-5.77 (1H, m), 5.40 (1H, br s), 4.54 (2H, s), 4.46-4.37 (2H, m), 3.28 (1H, s), 3.12-3.03 (3H, m), 2.59 (1H, d, J=18.5 Hz), 2.40 (1H, d, J=19.0 Hz), 2.12-2.05 (4H, m), 2.03-1.93 (1H, m), 1.80 (3H, dd, J=2.5, 1.0 Hz), 1.58 (1H, dd, signal part obscured), 1.21 (3H, s), 1.10 (3H, s), 0.90 (3H, d, J=6.5 Hz), 0.86 (1H, d, J=5.0 Hz); $^{13}C$ NMR (125 MHz, $CDCl_3$) $\delta_C$ 209.1, 173.4, 161.4, 159.7, 154.8, 150.0, 137.4, 135.4, 134.4, 133.2, 121.2, 120.1, 76.2, 73.8, 65.8, 63.8, 56.0, 39.7, 39.4, 37.2, 36.6, 32.5, 32.0, 23.5, 23.0, 21.5, 18.8, 15.6, 10.4; IR v 3402, 2922, 1714, 1575, 1447, 1418, 1378, 1329, 1259, 1082, 944, 883, 792, 760, 667 $cm^{-1}$; HRMS ($ES^+$) found: $[M+Na]^+$ 626.1875. $C_{30}H_{37}NO_8S_2$ requires $[M+Na]^+$ 626.1858.

C20-R8-prostratin 140

Example 3

Testing of Compounds for PKC Binding Activity

The PKC binding constant (Ki) was determined through a competitive binding assay using a procedure adapted from Wender et al. (*Org. Lett.* 2008, 10, 15, 3331-3334; See also Lewin et al., ($[^3H]$phorbol 12,13-dibutyrate Binding Assay for Protein Kinase C and Related Proteins, Chapter 12 in Protein Kinase C Protocols, pp 129-156) using ($[^3H]$phorbol 12,13-dibutyrate ($[^3H]$PDBu) as a probe. Parameters were adjusted for individual compounds. In a typical assay, a mixture of PKC isozymes, prepared by the method of Mochly-Rosen (See Mochley-Rosen et al., Domain Structure and Phosphorylation of Protein Kinase C. *J. Biol. Chem.* 1987, 262, 2291-2297), or alternately specific PKC-isozymes, were combined with Tris-HCl, KCl, $CaCl_2$, bovine serum albumin, water and phosphatidyl serine. The PKC mixture was added to serial dilutions of the respective analog; in addition, the PKC mixture was added to a solution of a compound with known PKC binding affinity and a solution containing no sample for reference. After addition of $[^3H]$PDBu, these samples were incubated, filtered through filters previously wetted with polyethyleneamine and the filters washed with Tris buffer.

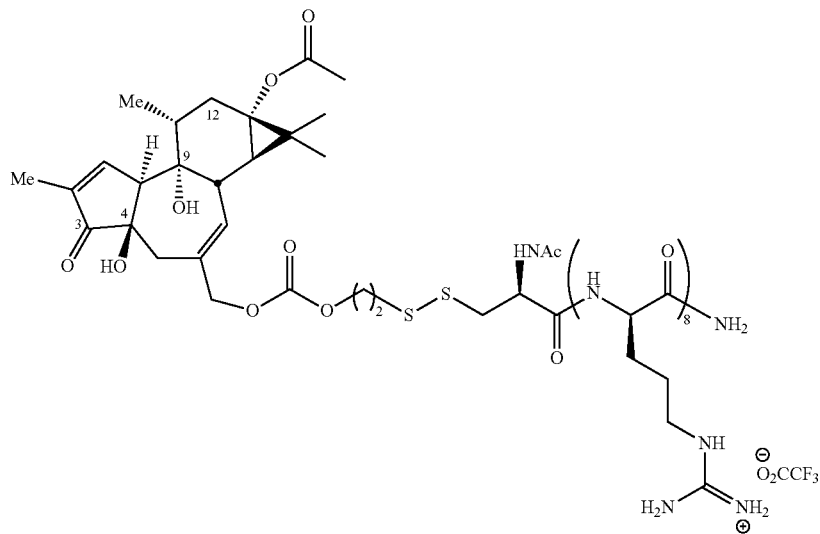

To a solution of the pyridyldithio linker (3 mg, 4.97 μmol) in DMF (200 μL) was added acylated D-cysteine D-octaarginine (14 mg, 5.97 μmol). The solution was stirred for 48 hours, at which point the reaction was complete as judged by HPLC and MALDI. The DMF was removed under vacuum. The crude reaction mixture was purified by semi-prep HPLC (5% MeCN/water increasing to 90% MeCN/water) and lyophilized to give prostratin-octaarginine transporter-construct as a white amorphous solid (2.7 mg, 0.0014 mmol 28%). Analytical data: $^1H$ NMR (500 MHz, MeOD) $\delta_H$ 7.59-7.57 (1H, m), 5.79-5.75 (1H, m), 4.59 (2H, s), 4.54-4.50 (2H, m), 4.42-4.22 (9H, m), 3.28-3.20 (16H, br), 3.15 (1H, m), 3.11 (1H, m), 3.07-2.97 (4H, m), 2.55 (1H, d, J=18.5 Hz), 2.43 (1H, d, J=19.0 Hz), 2.14 (1H, dd, J=14.0, 7.0 Hz), 2.08 (3H, s), 2.07 (3H, s) 2.06-2.02 (1H, m), 1.98-1.63 (32H, br), 1.80 (3H, dd, J=3.0, 1.5 Hz), 1.59 (1H, dd, J=14.5, 11.0 Hz), 1.21 (3H, s), 1.09 (3H, s), 0.95-0.90 (4H, m), 51 N—H and 2 O—H protons not observed.

The filters were then placed into scintillation vials which were then filled with Universol scintillation fluid. The filters were immediately counted in a scintillation counter (Beckman LS 6000SC). Counts per minute were averaged among three trials at each concentration. The data was then plotted using Prism by GraphPad Software and an IC50 (the concentration of analog required to displace half of the specific PDBu binding to PKC) was calculated. The IC50 then allowed determination of the Ki for the analog from the equation:

$$Ki = IC50/(1+[PDBu])/Kd \text{ of } PDBu)$$

The Kd of $[^3H]$PDBu was determined under identical conditions to be 1.17 nM.

Ki data are a measure of direct binding of the analogues to the protein PKC. EC50 data are a measure of survival of cancer cells when exposed to an analogue and therefore an effect and/or indirect measure of binding of analogues to the protein PKC.

The results of this assay are reported in Table 1a and 1b (of in Example 3) below.

TABLE 1a

| Analog | Ki (nM) |
|---|---|
| 22 | 1.6 |
| $C_{12}$-Methyl-$C_{13}$-Acetyl Phorbol | 3.0 (PKC βI) |

TABLE 1b

| Analog | $EC_{50}$ (nM) |
|---|---|
| 24 | 0.02 |
| 22 | 0.03 +/− 0.01 |
| 20 | 0.03 |
| $C_{12}$-Methyl-$C_{13}$-Acetyl Phorbol | 700 ± 200 |

Example 4

K562 Efficacy Studies

A cell efficacy assay (See Mossmann, Rapid colorimetric assay for cellular growth and survival: Application to proliferation and cytotoxicity assays. *J. Immunological Methods* 1983, 65, 55-63) was used to determine the EC50 for growth inhibition for K562 human leukemia cells. Parameters were adjusted for individual compounds; in a typical assay, the human leukemia cell line K562 in log phase growth were plated in a 96-well plate (final assay concentration~100,000 cells/mL). Analog was added via 10 or 20 triplicate serial dilutions (11 or 21 total concentrations) by 3× starting from 10 µM (final assay concentration). The cells were incubated at 37° C. for 48 h and worked up using standard MTT ((3-(4,5-Dimthylthiazol-yl)-2,5-diphenyltetrazolium bromide) protocols. Each compound was tested three times, and the error is reported as SEM.

The results of these studies are reported in Table 1 above.

Example 5

GFP Translocation Activity

Assay parameters were adjusted for individual compounds. In a typical assay, Chinese Hamster Ovary Cells (CHO K1) were cultured in F12 Kaighn's Growth Medium (Invitrogen Life Technologies Gibco) containing 10% fetal bovine serum with 50 units/ml penicillin, 50 µL/ml streptomycin and 4 mM glutamine (Gibco) and were transfected (See Teruel, M. N.; Meyer, T. Electroporation-induced formation of individual calcium entry sites in the cell body and processes of adherent cells. *Biophys. J*, 1997, 73, 1785-1796) with DNA encoding C-terminal GFP-tagged full-length PKC β1, β2, γ, δ, or ε using Lipofectamine™ 2000 (Invitrogen) according to manufacturer protocol. After incubation at 37° C. in an atmosphere of 5% $CO_2$ cells were plated onto sterile glass coverslips.

Images were exported as 12 bit files and analyzed using Metamorph data analysis software (Universal Imaging) (See FIGS. 8A to 8D). To monitor the translocation of the respective PKCisozyme-GFP, a small region of interest was selected in the cytosol of each cell and fluorescence intensity values graphed against time following background subtraction and normalization.

Translocation data are a measure of PKC protein action in response to binding of analogues to the protein PKC and therefore a measurement of an effect the analogues exert.

Example 6

Viral Activation of U1 Promonocytic Cells Infected with HIV Proviruses

Assay Parameters were adjusted for individual compounds; in a typical assay, U1 promonocytic cells containing two integrated HIV proviruses with mutations in the tat gene in both viral genomes with low levels of viral expression unless the cells are stimulated. Upon addition of activating molecules such as prostratin and prostratin analogs, the latent provirus is induced to express and viral particles are produced and released into the culture supernatant. After 48 hours of incubation with compound, we harvest the supernatant and assess the amount of virus present by using an ELISA specific for HIV p24 (the core protein of the HIV virion).

Viral Activation is direct measure of the effect the analogues have on the activation of virus; however, this is the result of a cellular signaling cascade triggered by binding of the analogues to the protein PKC.

The results of this assay are shown in Table 2 (in Example 6) below.

TABLE 2

| Compound | Dilution giving Maximum p24 Concentration in Supernatent |
|---|---|
| Prostratin | 1:100,000 |
| DPP | 1:10,000 |
| 20 | 1:100 |
| 22 | 1:100 |
| 24 | 1:100 |

Example 7

Despite their structural differences, both prostratin and bryostatin 1 share a common pharmacophore for protein kinase C (See *Proc. Natl. Acad. Sci. USA* 1988, 85, 7197-201, which is incorporated herein by reference). As a result, given the PKC affinity of bryostatin 1 for the C1 domain of PKC (1.35 nM) (See *J. Am. Chem. Soc.* 1982, 104, 6846-8, which is incorporated herein by reference) as well as its ability to induce viral expression in chronically infected promonocytic U1 and T-lymphocytic ACH-2 cells in vitro (See, *J. Virol.* 1990, 64, 4306-12 and *Proc. Natl. Acad. Sci. USA* 1993, 90, 4674-4676, both of which are incorporated herein by reference), agents of this structural class are proposed to have therapeutic potential analogous to prostratin for the treatment of HIV/AIDS. The ability of bryostatin to induce viral expression from both U1 and ACH-2 cell lines is inhibited by the PKC inhibitor Gö 6976 (See, *Chem. Asian. J.* 2010, 5, 704-54, which is incorporated herein by reference), suggesting the importance of cellular PKC activation in bryostatin's mode of action.

A number of analogs of bryostatin 1 with comparable or superior affinities for PKC have been reported (See, *Chem. Asian. J.* 2010, 5, 704-54). In addition to PKC binding, several lead analogs (labeled picolog, C13 olefin, and C13 Z enoate as shown below) were investigated in the U1 latency model. The syntheses of these analogs have been reported previously by Wender et. al. (See, *J. Am. Chem. Soc.* 2002, 124, 13648-13649 and J. Am. Chem. Soc. 2008, 130, 6658-6659, both of which are incorporated herein by reference).

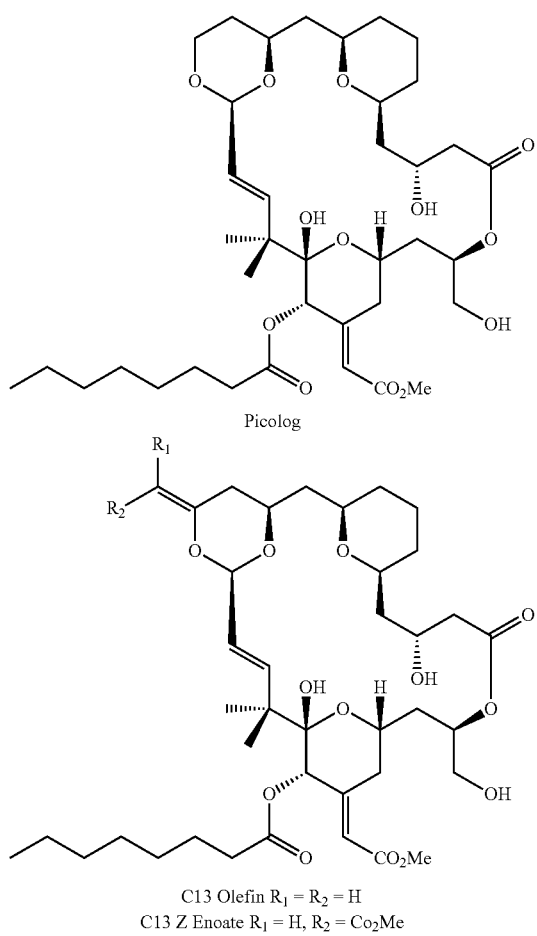

Picolog

C13 Olefin R$_1$ = R$_2$ = H
C13 Z Enoate R$_1$ = H, R$_2$ = Co$_2$Me

Structures of picolog, C13 olefin, and C13 Z enoate analogs investigated in the U1 latency model.

The PKC binding affinities (measure in a rat brain PKC isoform mixture), minimum concentrations required to induce U1 viral expression (as measured by p24 levels), and concentrations corresponding to the maximum observed p24 levels are shown in Table 1 below (data generated in collaboration with J. Zack et. al. at UCLA). Bryostatin 1 as well as the synthetic analogs are all more potent PKC ligands. Additionally, these agents induce U1 viral expression at lower concentrations (up to 3 orders of magnitude), and lower concentrations are required to achieve maximum p24 levels. Relative to bryostatin 1, the synthetic analogs display comparable or superior PKC binding affinities and abilities to induce viral expression in the U1 cell line.

TABLE 1

PKC K$_i$ values, minimum concentrations required for U1 viral expression, and concentrations at maximum p24 levels for prostratin, bryostatin 1, picolog, the C13 olefin analog, and the C13 Z enoate analogs.

| Compound ID | PKC K$_i$ (nM) | Minimum Concentration for Viral Expression (nM) | Concentration at Maximum p24 Level (nM) |
|---|---|---|---|
| Prostratin | 50 | 1000 | 10000 |
| Bryostatin 1 | 1.35 | 1 | 1 |
| Picolog | 3.1 | 10 | 1000 |

TABLE 1-continued

PKC K$_i$ values, minimum concentrations required for U1 viral expression, and concentrations at maximum p24 levels for prostratin, bryostatin 1, picolog, the C13 olefin analog, and the C13 Z enoate analogs.

| Compound ID | PKC K$_i$ (nM) | Minimum Concentration for Viral Expression (nM) | Concentration at Maximum p24 Level (nM) |
|---|---|---|---|
| C13 Olefin | 1.63 | 1 | 1000 |
| C13 Z Enoate | 0.9 | 0.1-1 | 100 |

In addition to the U1 data, the compounds from Table 1 above were tested for their effects on surface markers in primary quiescent CD+ T cells (data generated by J. Zack et. al. at UCLA). Two markers measured were CD69, which is an activation marker induced by prostratin, and CD4, whose downregulation has been linked to the ability of prostratin to prevent the spread of HIV infection. Bryostatin 1 also downregulates CD4 cell surface receptors in peripheral blood T lymphocytes (See, *Cell Regul.* 1991, 2, 95-103 and *Int. J. Immunopharmacol.*, 1990, 12, 481-490, both of which are incorporated herein by reference). This effect is abrogated by co-incubation with the PKC inhibitor staurosporine. The minimum concentrations required for CD69 induction and CD4 decrease are shown in Table 2 below. Again, both bryostatin 1 and the synthetic analogs are more potent than prostratin in these capacities. Also, the synthetic analogs are all potent for CD69 induction and CD4 decrease, with the C13 Z enoate having comparable activity to bryostatin 1.

TABLE 2

Minimum concentration for CD69 induction and CD4 decrease in primary quiescent CD4+ T cells treated with prostratin, bryostatin 1, picolog, the C13 olefin analog, and the C13 Z enoate analog.

| Compound ID | Minimum Concentration for CD69 Induction (nM) | Minimum Concentration for CD4 Decrease (nM) |
|---|---|---|
| Prostratin | 1000 | 10000 |
| Bryostatin 1 | 1 | N/A |
| Picolog | 100 | 1000 |
| C13 Olefin | 10 | 100 |
| C13 Z Enoate | 1 | 100 |

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

While only a few embodiments of the present disclosure have been shown and described herein, it will become apparent to those skilled in the art that various modifications and changes can be made in the present disclosure without departing from the spirit and scope of the present disclosure. All

We claim at least the following:

1. A compound according to the formula:

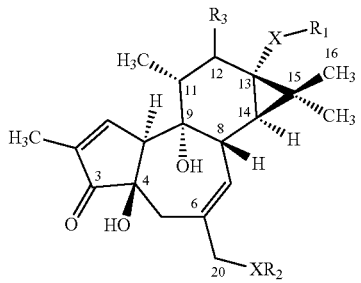

wherein X in each instance is independently selected from: O, S, and N;
- wherein $R_1$ is a mono- or di-substituent, depending on X, selected from: H, substituted or unsubstituted alkyl, substituted or unsubstituted aryl, substituted or unsubstituted cycloalkyl, substituted or unsubstituted cycloalkenyl, substituted or unsubstituted heteroaryl, substituted or unsubstituted biaryl, substituted or unsubstituted fused aryl, substituted or unsubstituted alkenyl, or substituted or unsubstituted alkynyl;
- wherein R2 is a mono- or di-substituent, depending on X, and is H; and
- wherein R3 is a mono- or di-substituent selected from: H, substituted or unsubstituted alkyl, substituted or unsubstituted aryl, substituted or unsubstituted cycloalkyl, substituted or unsubstituted cycloalkenyl, substituted or unsubstituted aryl, substituted or unsubstituted biaryl, substituted or unsubstituted fused aryl, substituted or unsubstituted alkenyl, and substituted or unsubstituted alkynyl, alkoxy, acetoxy, phenyloxy, alkylthio, phenylthio, halogen, alkylamino, or diphenylamino,
- wherein when X in $XR_1$ is O, then R1 is —C(=O)$CH_2$-FMA, or —C(=O)CH($CH_3$)-FMA, where FMA is selected from the group consisting of: an unsubstituted heteroaryl, substituted or unsubstituted fused aryl, substituted or unsubstituted cycloalkyl, and substituted or unsubstituted biaryl, or $R_1$ is —C(=O)-FMA, then FMA is selected from the group consisting of: a substituted or unsubstituted heteroaryl, substituted or unsubstituted fused aryl, substituted cycloalkyl, and substituted or unsubstituted biaryl.

2. The compound according to claim 1, where X is O.

3. The compound according to claim 1, where the compound has a protein kinase C stimulatory activity.

4. The composition of claim 1, wherein one of the X groups is selected from: S and N, and wherein the other of the X groups is selected from: O, S, and N.

5. A compound according to Formula II described below:

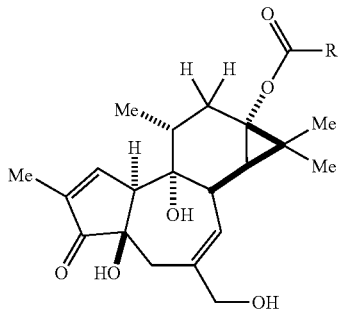

Formula II wherein R is selected from the group consisting of: substituted cycloalkyl, substituted or unsubstituted heteroaryl, substituted or unsubstituted biaryl, and substituted or unsubstituted fused aryl.

6. The compound of claim 1, wherein when X in $XR_1$ is O, then $R_1$ is —C(=O)CH($CH_3$)-FMA, where FMA is selected from the group consisting of: heteroaryl, substituted or unsubstituted fused aryl, substituted or unsubstituted cycloalkyl, and substituted or unsubstituted biaryl.

7. The compound of claim 1, where R3 is selected from: substituted or unsubstituted alkyl, substituted or unsubstituted aryl, substituted or unsubstituted cycloalkyl, substituted or unsubstituted cycloalkenyl, substituted or unsubstituted aryl, substituted or unsubstituted biaryl, substituted or unsubstituted fused aryl, substituted or unsubstituted alkenyl, and substituted or unsubstituted alkynyl, alkoxy, acetoxy, phenyloxy, alkylthio, phenylthio, halogen, alkylamino, or diphenylamino.

* * * * *